(12) United States Patent
Frauenrath et al.

(10) Patent No.: US 12,024,613 B2
(45) Date of Patent: Jul. 2, 2024

(54) COMPOSITION CONTAINING A POLYMER AND AN ADDITIVE

(71) Applicant: École Polytechnique Fédérale De Lausanne (EPFL)—Technology Transfer Office (TTO), Lausanne (CH)

(72) Inventors: Holger Frauenrath, Epalinges (CH); Daniel Görl, Denges (CH); Christopher Plummer, Echandens (CH)

(73) Assignee: École Polytechnique Fédérale De Lausanne (EPFL)—Technology Transfer Office (TTO), Lausanne (CH)

( * ) Notice: Subject to any disclaimer, the term of this patent is extended or adjusted under 35 U.S.C. 154(b) by 986 days.

(21) Appl. No.: 16/763,689

(22) PCT Filed: Nov. 14, 2018

(86) PCT No.: PCT/EP2018/081272
§ 371 (c)(1),
(2) Date: May 13, 2020

(87) PCT Pub. No.: WO2019/096870
PCT Pub. Date: May 23, 2019

(65) Prior Publication Data
US 2020/0299484 A1    Sep. 24, 2020

(30) Foreign Application Priority Data
Nov. 14, 2017    (WO) ................ PCT/EP2017/079133

(51) Int. Cl.
C08K 5/20 (2006.01)
C07K 5/062 (2006.01)
C08F 8/30 (2006.01)
C08F 236/14 (2006.01)
C08G 77/388 (2006.01)

(52) U.S. Cl.
CPC ............ C08K 5/20 (2013.01); C07K 5/06026 (2013.01); C08F 8/30 (2013.01); C08F 236/14 (2013.01); C08G 77/388 (2013.01); *C08F 2810/20* (2013.01)

(58) Field of Classification Search
CPC ..... C08K 5/20; C07K 5/06026; C08F 236/14; C08F 2810/20; C08F 8/30; C08G 77/388
See application file for complete search history.

(56) References Cited

U.S. PATENT DOCUMENTS

| | | |
|---|---|---|
| 4,927,897 A | 5/1990 | Kawata et al. |
| 4,954,428 A | 9/1990 | Lewis et al. |
| 10,787,576 B2 | 9/2020 | Frauenrath et al. |
| 2004/0048999 A1 | 3/2004 | Herzig et al. |
| 2006/0223947 A1 | 10/2006 | Olesik et al. |
| 2018/0171152 A1 | 6/2018 | Frauenrath et al. |
| 2019/0048202 A1 | 2/2019 | Frauenrath et al. |

FOREIGN PATENT DOCUMENTS

| | | | |
|---|---|---|---|
| JP | 09249717 A | 9/1997 | |
| JP | 2004099890 | 4/2004 | |
| JP | 2004149614 | 5/2004 | |
| WO | 2014/080043 | 5/2014 | |
| WO | WO-2014080043 A1 * | 5/2014 | ............... C08H 1/00 |
| WO | 2016174266 | 11/2016 | |
| WO | 2016189047 | 12/2016 | |

OTHER PUBLICATIONS

Cornwell, Daniel J. et al., "Expanding the scope of gels—combining polymers with low-molecular-weight gelators to yield modified self-assembling smart materials with high-tech applications", Mater. Horiz., vol. 2, No. 3, Jan. 30, 2015, pp. 279-293.
Croisier, Emmanuel et al., "A toolbox of oligopeptide-modified polymers for tailored elastomers", Nature Communications, vol. 5, No. 1, Sep. 8, 2014, p. 2 and p. 4.
International Preliminary Report on Patentability for PCT/EP2018/081272 dated May 19, 2020.
Jahnke, Eike et al., "Molecular Level Control over Hierarchical Structure Formation and Polymerization of Oligopeptide-Polymer Conjugates", Advanced Materials, vol. 20, No. 3, Jan. 9, 2008, pp. 409-414.
Hoheisel, Tobias N. et al., "A Convenient Negishi Protocol for the Synthesis of Glycosylated Oligo(ethynylene)s", Organic Letters, vol. 10, No. 20, Oct. 16, 2008, pp. 4525-4528.
International Preliminary Report on Patentability for PCT/EP2016/059773 dated Nov. 9, 2017.
International Preliminary Report on Patentability for PCT/EP2016/061828 dated Nov. 28, 2017.
International Search Report for PCT/EP2016/059773 dated Dec. 5, 2016.

(Continued)

*Primary Examiner* — Robert D Harlan
(74) *Attorney, Agent, or Firm* — Honigman LLP; Andrew N. Weber; Jonathan P. O'Brien

(57) ABSTRACT

The invention describes a composition containing a) a functionalized polymer (10) that comprises at least one polymer segment (13) and at least two polymer aggregating segments (11,12) capable of forming non-covalent bonds based on a supramolecular interaction, b) an aggregating additive (20) that comprises at least one additive aggregating segment (21) capable of forming non-covalent bonds based on the same supramolecular interaction as the polymer aggregating segments (11,12), wherein the polymer aggregating segments (11,12) and the additive aggregating segment (21) are ditopic, wherein the polymer aggregating segments (11,12) and the additive aggregating segment (21) are designed such that they can form aggregates (31) that contain polymer aggregating segments (11,12) and additive aggregating segments (21), and wherein the aggregating additive (20) has a molecular weight of from 50 g/mol to 2000 g/mol. The invention also describes a method for the preparation of the composition according to the invention, the use of an aggregating additive (20) with a functionalized polymer (10), and the use of the composition according to the invention.

17 Claims, 6 Drawing Sheets

(56) References Cited

OTHER PUBLICATIONS

Figure 1:
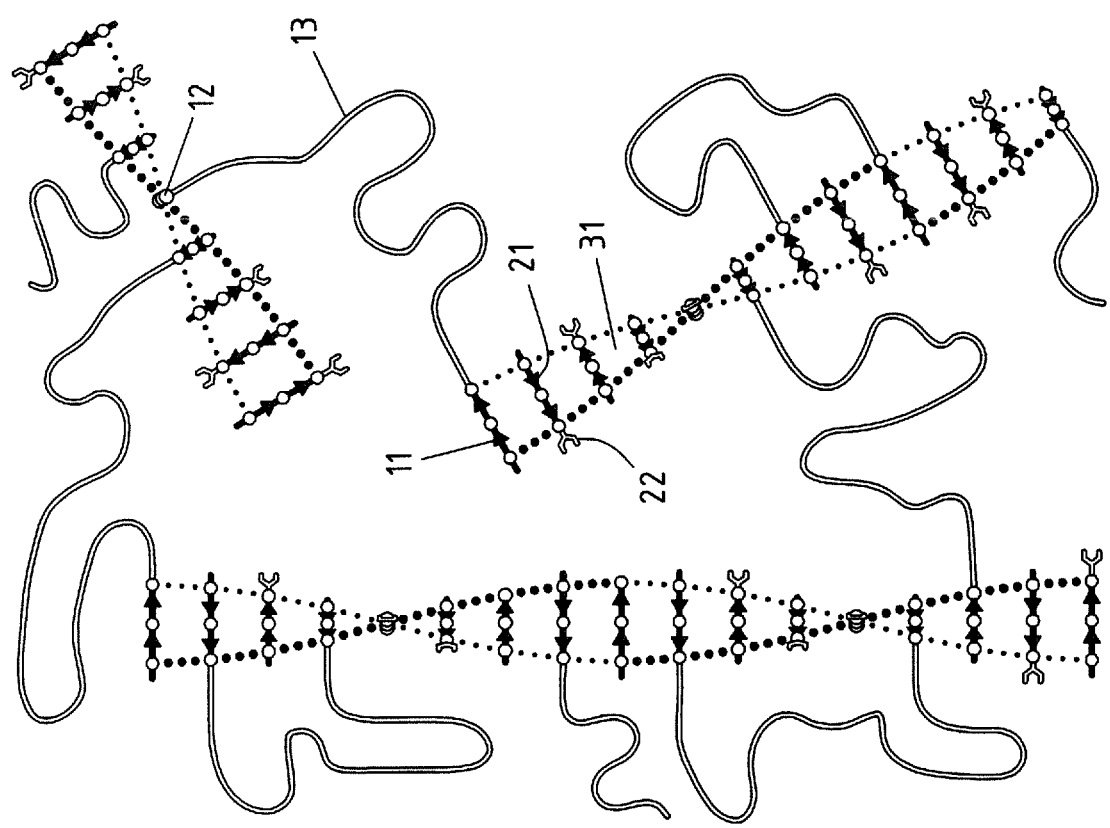
Figure 1:
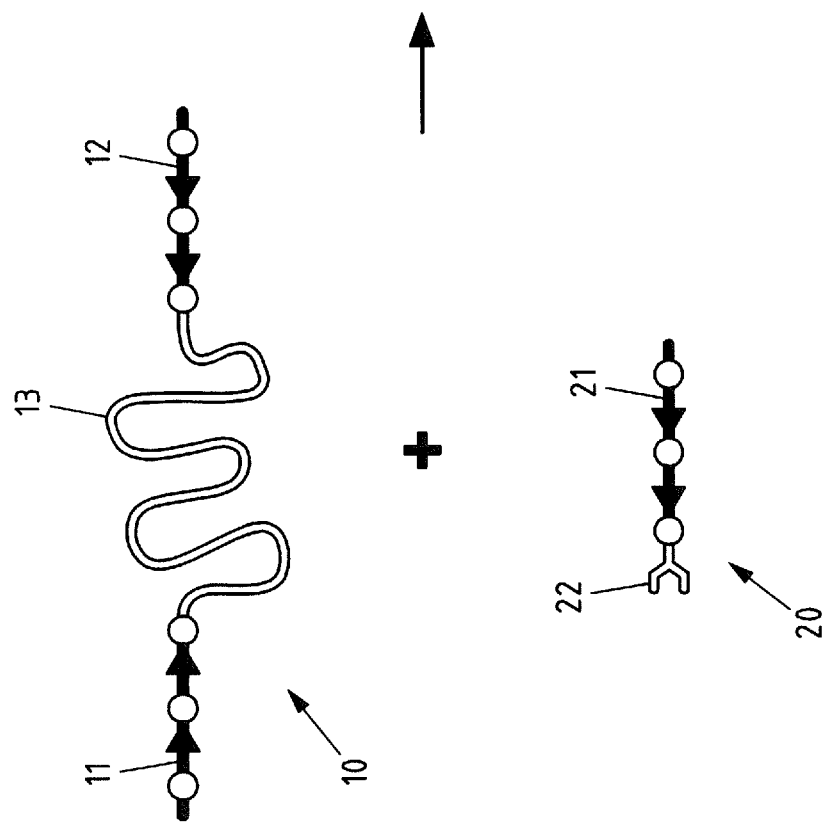

International Search Report for PCT/EP2016/061828 dated Sep. 2, 2016.
Schrettl, Stephen et al., "Facile synthesis of oligoyne amphiphiles and their rotaxanes", Chemical Science, vol. 6, No. 1, Jan. 1, 2015, pp. 564-574.
Schrettl, Stephen et al., "Functional carbon nanosheets prepared from hexayne amphiphile monolayers at room temperature", Nature Chemistry, vol. 6, No. 6, May 4, 2014, pp. 468-476.
Schrettl, Stephen et al., "Functional carbon nanosheets prepared from hexayne amphiphile monolayers at room temperature", Nature Chemistry, vol. 6, No. 6, May 4, 2014, pp. 468-476, Supplementary Information.
Written Opinion of the International Searching Authority for PCT/EP2016/059773 dated Dec. 5, 2016.
Written Opinion of the International Searching Authority for PCT/EP2016/061828 dated Sep. 2, 2016.
International Search Report for PCT/EP2018/081272 dated Feb. 11, 2019.
Written Opinion of the International Searching Authority for PCT/EP2018/081272 dated Feb. 11, 2019.

\* cited by examiner

COMPOSITION CONTAINING A POLYMER AND AN ADDITIVE

FIELD OF THE INVENTION

The invention relates to a composition containing a polymer comprising at least one polymer segment and at least two segments capable of forming non-covalent bonds based on a supramolecular interaction, and an additive comprising at least one segment capable of forming non-covalent bonds based on the same supramolecular interaction as the at least two segments of the polymer. The invention also relates to the methods of preparation of the composition and the use of an additive comprising at least one segment capable of forming non-covalent bonds based on a supramolecular interaction with a polymer comprising at least one polymer segment and at least two segments capable of forming non-covalent bonds based on the same supramolecular interaction as the additive. The composition can be used to provide thermoplastic elastomers and thermoplastic polymer materials with improved toughness and/or temperature range of operation.

BACKGROUND OF THE INVENTION

Applications of Thermoplastic Elastomers

The automotive and transport industries account for 70-75% of global rubber production, and the global rubber industry is currently expanding rapidly into other sectors such as the electronics industry and, notably, the medical sector, where there is a particularly high growth potential for high performance elastomers. At the same time, the rubber industry is increasingly looking to engineered thermoplastic elastomers (TPEs) as a substitute for conventional thermoset rubbers. TPEs offer improved recyclability, which is often imposed on the end-user by legislation, especially in the automotive industry, but also better processability with reduced cycle times, and significantly improved design flexibility, with processing options that allow straightforward manufacture of even the most complex multimaterials parts. However, existing TPE solutions are unable to fulfil the stringent performance requirements in many applications, particularly in the automotive industry, owing to either their insufficient thermal stability and creep resistance, or their inferior elasticity and shape recovery.

TPEs typically consist of a continuous rubbery phase combined with rigid domains that act as physical crosslinks. Such materials behave as elastomers in that they show quasi-instantaneous shape recovery on loading and unloading at the operating temperature, T. However, unlike conventional vulcanized rubber elastomers, they do not contain a continuous network of covalent crosslinks, and may therefore be melt-processed at temperatures exceeding the glass transition temperature, $T_g$, or melting temperature, $T_m$, of the rigid domains [J. G. Drobny, *Handbook of Thermoplastic Elastomers*, 2nd edition, Elsevier 2014]. TPEs are most commonly based on triblock copolymers or segmented copolymers comprising one or more long "soft" segments of a polymer with $T_g$<T, and a minimum of two "hard" segments of either an amorphous polymer with $T_g$>T or a semicrystalline polymer with $T_m$>T. Microphase segregation of these segments in the bulk leads to a dispersion of discontinuous rigid domains in a continuous matrix of the soft polymer, which exhibits rubber elasticity.

The most important class of TPEs for industrial applications are styrene block copolymers (SBCs, 35-38% market share, e.g. Kraton™), in which physical crosslinking occurs via glassy styrene-rich inclusions. These include poly(styrene-butadiene-styrene) (SBS), poly(styrene-isoprene-styrene) (SIS), poly(styrene-isobutylene-styrene) (SIBS), or poly(styrene-(ethylene-co-butylene)-styrene) (SEBS). Further important classes of TPEs are olefinic thermoplastic elastomers (TPOs, 13-16% market share) based on rubbery semicrystalline polyolefin copolymers with very low degrees of crystallinity, thermoplastic vulcanizates (TPVs, 14-17% market share), in which the rubbery phase is chemically crosslinked, but forms discrete inclusions in a continuous thermoplastic matrix (e.g. isotactic poly(propylene)-vulcanized ethylene-propylene-diene-monomer (EPDM) blends, and thermoplastic silicone vulcanizates with polyamide matrices), copolyester elastomers (COPEs, e.g. Hytrel™, 8-11% market share), thermoplastic polyurethane elastomers (TPUs, 19-22% market share), and polyamide elastomers (PAEs, e.g. Vestamid™ and Pebax™, around 1% market share) [J. G. Drobny, *Handbook of Thermoplastic Elastomers*, 2nd edition, Elsevier 2014; J. Markarian, *Plastics Additives & Compounding*, September/October 2008].

The applications of TPEs and their limitations are determined by the softening temperature, $T_s$, i.e., the temperature above which the rigid domains are no longer effective as physical crosslinks, as well as their resilience (the ability of a material to recover its original shape after deformation) and stability at high loads and/or temperatures (creep resistance, compression set), and their elasticity (low hysteresis). All of these key properties are strongly dependent on the thermomechanical properties of the rigid phase. Indeed, a major challenge currently faced by the industry is the development of TPEs that combine a high softening temperature, $T_s$ ($\geq 150°$ C.), with a high degree of elasticity. This is driven by an increasing demand for high temperature elastomers e.g. for under-hood applications in the automotive industry, which most commodity vulcanized rubbers fail to meet, owing to their poor high temperature stability, which is typically limited by their chemical stability. Exceptions include EPDM, which has an operating temperature of up to about 150° C., acrylic rubbers, silicone-based high temperature vulcanizates (HTVs), whose maximum operating temperatures are as high as 300° C., and fluorocarbon, fluorosilicone and perfluorocarbon rubbers. Of these, EPDM is most widely used in automotive applications such as brake seals and radiator gaskets, but it performs poorly in contact with petroleum oils, lubricants and fuel. Conversely, acrylic rubbers show poor properties in contact with moisture, acids and bases. The main disadvantage of silicone-based HTVs is their high price, typically 7 to 10 times that of commodity vulcanizates. They also show limited resistance to strong acids & bases, alcohols and fuel, and have modest mechanical properties, in particular, low tensile strength compared with commodity vulcanizates. High temperature fluorocarbon, fluorosilicone and perfluorocarbon rubbers also suffer from moderate mechanical properties, and they are between 30 and 1000 times more expensive than commodity vulcanizates.

At present, the low $T_g$ or $T_m$ of the rigid domains in the commonly employed SBCs, TPOs, and TPVs renders them unsuitable for use at temperatures above 90-100° C. [H. Ohtaki, F. Shimizu, G. W. Coates, G. H. Fredrickson, Mitsubishi Chemical Corporation, Cornell University US 20150057415, "Thermoplastic Elastomer Composition and Process for Manufacturing the Same"]. By contrast, the softening temperatures, $T_g$, of heat resistant TPVs, COPEs and PAEs may exceed 200° C. However, such materials typically show a far more restricted range of softness/hardness than vulcanizates, and, in the case of COPEs, a very low elastic limit of around 10-15% [A. K. Bhowmick, H. L. Stephens, *Handbook of Elastomers*, Marcel Dekker 2001].

The high temperature resistance of PAEs, as well as many of the outstanding properties of TPUs are due to stabilization of their rigid domains by hydrogen-bonding. TPUs are comparatively cheap (about twice as expensive as natural rubber but longer lasting) and have significant performance advantages compared with other elastomers, e.g., resistance to weathering, ozone and hydrocarbons, excellent abrasion resistance, toughness, tearing resistance and strength [C. Prisacariu, *Polyurethane Elastomers: From Morphology to Mechanical Aspects*, Springer 2011]. Nevertheless, although the applications of TPUs now range from heavy-duty transmission belts to prosthetic fingers, their use in tires has remained limited to slow-moving vehicles in controlled environments, such as electric indoor forklift trucks, and temporary components, such as run-flat inserts. This is because achieving a high load-bearing capacity and low rolling resistance in TPUs requires a high rigid domain content, which increases their relative hardness and hence reduces their cushioning ability, traction, and grip. Moreover, TPUs tend to perform poorly at high speeds owing to heat generation and consequent instabilities, such as meltdown under braking [A. K. Bhowmick, H. L. Stephens, *Handbook of Elastomers*, Marcel Dekker 2001; C. Prisacariu, *Polyurethane Elastomers: From Morphology to Mechanical Aspects*, Springer 2011; Weblinks: http://www.thombert.com/website/white papers/PolyurethaneRubberTires.pdf, http://tomdwyercom/2011/uncategorized/will-polyurethane-replace-rubber-for-tires]. In practice, the upper continuous use temperatures of commercial TPUs seldom exceed about 120° C. owing to incomplete phase separation and the disordered nature of the rigid domains [C. Prisacariu, *Polyurethane Elastomers: From Morphology to Mechanical Aspects*, Springer 2011; M. Szycher, *Handbook of Polyurethanes*, 2nd edition, CRC Press 2012; M. F. Sonnenschein, W. Koonce, *Polyurethanes, in Encyclopedia of Polymer Science and Technology*, Wiley 2011; H. Ulrich, *Polyurethanes, in Encyclopedia of Polymer Science and Technology*, Wiley 2001; G. Oertel, *Polyurethane Handbook*, Hanser 1985; F. L. G. Malet, in *Handbook of Condensation Thermoplastic Elastomers*, S. Fairkov, ed., Wiley 2005].

The most common PAEs are segmented block copolymers of polyamide 12 (PA12) and polyether (e.g. Vestamid™ [Weblink: http://www.vestamid.com/product/vestamid/en/Pages/default.aspx]), whose melting points are well below the melting point of pure PA12 of about 170° C. However, PA6-based PAEs are commercially available with maximum service temperatures in excess of 200° C. (Pebax™ and Nyrim™), and those of segmented PAEs containing aromatic or semiaromatic polyamide segments may be even higher than this, provided they are able to form ordered lamellar crystals with well-defined melting points that remain high in spite of the diluting effect of the matrix [Weblinks: http://www.extrememeterials-arkema.com/en/product-families/pebax-elastomer-family/https://www.brueggemann.com/english/nyrim.html]. Certain PAEs consequently retain many of their useful physical properties at temperatures of up to 300° C. [J. G. Drobny, *Handbook of Thermoplastic Elastomers*, 2nd edition, Elsevier 2014; F. L. G. Malet, in *Handbook of Condensation Thermoplastic Elastomers*, S. Fairkov, ed., Wiley 2005; M. C. E. J. Niesten, J. Feijen, R. J. Gaymans, *Polymer* 2000, 41, 8487-8500; P. Latko, A. Boczkowska, in *Flexible and Stretchable Electronic Composites*, K. Ponnamma et al. eds., Springer 2016].

They are hence among the most promising competitors to silicone-based HTVs. However, their range of hardness/softness is far smaller than that of the HTVs and indeed it is debatable whether many PAEs can be considered to be true elastomers based on their mechanical behavior. Moreover, the mechanical properties of PAEs cannot be tailored to specific purposes, in particular, it is not possible to achieve good elastomeric properties and high melting points simultaneously. Silicone-based HTVs on the other hand suffer from the fact that they are difficult and, therefore, expensive to process. Moreover, silicone-based HTVs can only be used in a limited number of environments. Finally, the mechanical properties of silicone-based HTVs are only modest. This is because the high degrees of crystallinity necessary to ensure resistance to high temperatures in these materials are incompatible with desirable properties in elastomers, such as resilience, low tensile moduli, and low hysteresis.

The applications of PAEs currently include sporting and leisure goods, automotive parts, hydraulic and pneumatic equipment, wire and cable jacketing and tubing, and medical applications. PAEs still only represent around 1% of the total TPE market. However, global consumption over the next few years is expected to increase significantly, driven principally by the sporting goods, electronics (dielectric elastomers, compliant nanocomposite electrodes, humidity sensors, touch-pads, etc.), and automotive industries, in spite of their high price compared both with thermoset rubbers and other TPEs and thanks to their high service temperature and resistance to oils, aging and abrasion, as well as their excellent dielectric strength [P. Latko, A. Boczkowska, in *Flexible and Stretchable Electronic Composites*, K. Ponnamma et al. eds., Springer 2016]. PAEs and PAE-based composites are also of interest for filtration, owing to their high permeability and polar gas selectivity, and their suitability for fabricating thin membranes [S. Armstrong, B. Freeman, A. Hiltner, E. Baer, *Polymer* 2012, 53, 1383-1392.].

While typical TPEs based on COPEs, TPUs, or PAEs show high stability and creep resistance, but suffer from inferior elasticity and hysteresis-free shape recovery, materials based on polymers with distinct hydrogen-bonded self-assembling end groups, such as oligopeptides, oligoamides, oligourethanes, or oligoureas have so far received very little attention in the related scientific and patent literature. TPEs with terminal oligopeptide segments of less than 20 amino acids in length have been disclosed in a patent application filed by the University of Akron (EP2841505) [L. Jia, J. Scavuzzo, J. Kennedy, University of Akron, EP2841505, "Thermoplastic Elastomers Containing an Oligopeptide Hard Component"], with claims about specific temperatures such as glass transitions or melting temperatures. The University of Akron has also patented an elastomer with grafted oligoamide units (WO2015138871) [L. Jia, J. Scavuzzo, J. Kennedy, University of Akron, WO2015138871, "Supramolecular Elastomer Networks Containing Grafted Oligoamide Hard Components"]. Finally, Goodyear has described the use of a functionalized elastomer comprising grafted oligoamides or oligopeptides (EP2639246) [R. Mruk, R. F. Roskamp, A. Hermann, R. W. Zentel, The Goodyear Tire & Rubber Company, EP2639246, "Functionalized Elastomer and Tire Comprising Such an Elastomer"]. This document claims the use of the material in tires in order to improve their tear behavior. In all of these cases, however, the hydrogen-bonding interactions between the oligoamide or oligopeptide segments merely supplement a covalent network obtained by vulcanization, supposedly because purely supramolecular elastomers have shown insufficient mechanical strength at large strains.

Thermoplastic Polymers with Improved Operating Temperature Range and Long-Term Stability High temperature stability is also an important issue for many amorphous or semicrystalline commodity thermoplastics, which are unable to compete with more expensive engineering polymers in applications such as under-bonnet automotive parts that are subject to sustained and/or transient exposure to elevated temperatures. The low glass transition temperatures $T_g$ and melting temperatures $T_m$, typical of commodity polyolefins such as poly(ethylene) ($T_m \approx 140°$ C.) and poly(propylene) ($T_m \approx 160°$ C.) render them particularly susceptible to long-term embrittlement under low-level loading conditions, such as those encountered in water and gas pipes under internal pressure, and many amorphous glassy polymers, such as atactic poly (styrene) ($T_g \approx 100°$ C.) or poly(methyl methacrylate) (PMMA) ($T_g \geq 85°$ C., depending on tacticity), show significant degradation in tensile strength as the temperature approaches the glass transition temperature. Increasing the molar mass, long chain branching, and light crosslinking are known to improve long term performance and temperature stability of such materials by stabilizing the entanglement network [C. J. G. Plummer, Adv. Polym. Sci. 2004, 169, 75-119; Y. L. Huang, N. Brown, J. Polym. Sci. Polym. Phys. Ed. 1991, 29, 129-137; B. Langer, A. Berthold, W. Grellmann, H. F. Enderle, Mater. Testing 2012, 54, 578-583; 49; H.-H. Kausch, R. Gensler, C. Grein, C. J. G. Plummer, P. Scaramuzzino, J. Macromol. Sci. Phys. B 1999, 38, 803-815; R. A. C. Deblieck, D. J. M. van Beek, K. Remerie, I. M. Ward, Polymer 2011, 52, 2979-2990; F. Nilsson, X. Lan, T. Gkourmpis, M. S. Hedenqvist, U. W. Gedde, Polymer 2012, 53, 3594-3601]. However, as with thermoplastic elastomers, significant improvements in performance are often achieved at the expense of processability and recyclability owing to the concomitant increases in melt viscosity [T. C. B. McLeish, Curr. Opinion. Solid State Mater. Sci. 1997, 2, 678-682], and in the case of semicrystalline polymers, too high a molar mass may lead to reduced crystallinity with adverse consequences for strength and stiffness [M. G. Andersson, J. Hynynen, M. R. Andersson, P.-O. Hagstrand, T. Gkourmpis, C. Müller, J. Polym. Sci. Polym. Phys. 2016, 55, 146-156]. An extreme example is provided by ultra-high molecular weight poly(ethylene), which has outstanding abrasion resistance, but cannot be processed using conventional techniques such as extrusion of thermoplastics. An alternative means of reducing high temperature creep or limiting long term embrittlement in polyolefins might be to introduce highly localized physical crosslinks that are stable at significantly higher temperatures than the bulk melting point. They should hence strongly hinder forced disentanglement in the solid state, which is thought to be at the origin of long term embrittlement [T. C. B. McLeish, C. J. G. Plummer, A. M. Donald, Polymer 1989, 30, 1651-1655; L. L. Berger, E. J. Kramer, Macromolecules 1987, 20, 1980-1985; C. J. G. Plummer, A. Goldberg, A. Ghanem, Polymer 2001, 42, 9551-9564].

In the case of poly(styrene), and other commodity amorphous glassy polymers, it has been shown that promoting strain-induced crystallization through controlled tacticity may promote stability in the temperature range immediately below $T_g$ [C. J. G. Plummer, H.-H. Kausch, Polymer 1993, 43, 1972-1974]. However, although crystallizable isotactic and syndiotactic grades of poly(styrene) are available, they are more expensive, and difficult to process owing to their high melting temperatures. Another major problem with commercial general-purpose poly(styrene) is that it shows very limited elasticity above $T_g$ owing to their low entanglement densities. This severely limits not only their dimensional stability when they are subjected to transient exposure to temperatures above $T_g$, but also their processability, leading to poor results in film blowing, for example, and problems with non-uniform cell morphologies and excessive open pore content during foaming.

Poor melt strength is a recurrent problem not only with widely used amorphous polymers such as poly(styrene) and poly(methyl methacrylate), but also many semicrystalline polymers, including polyolefins such as poly(ethylene) and poly(propylene), and polyesters, for example, whose processing temperatures are generally well above $T_g$, i.e., well above the temperature range corresponding to the rubbery plateau. Poor melt strength may impact not only film blowing and foaming, but also a wide variety of other processes involving extrusion or thermoforming. Again, modification to the chain architecture and molar mass distribution, often via reactive processing in the presence of additives (peroxides, epoxies etc.), have been widely investigated as a means to improve processability in such polymers, along with blending or filler addition, copolymerization with moieties containing polar or ionic functional groups, and processing at temperatures immediately below $T_m$ [S. Japon, Y. Leterrier, J. A. E. Månson, Polym. Eng. Sci. 2000, 40, 1942-1952; D. M. Bigg, Polym. Eng. Sci. 1988, 28, 830-841; M. Drewniak et al., U.S. Pat. No. 6,770,697 B2, "High melt-strength polyolefin composites and methods for making and using same"; B. J. Scheve, U.S. Pat. No. 4,916,198 A, "High melt strength, propylene polymer, process for making it, and use thereof"; C.-J. Johansson, EP0737219 B1, "Processable poly(lactide)s"; C.-F. Hsu et al., U.S. Pat. No. 6,797,737 B1, "Crosslinked foam of ethylene vinyl acetate copolymer and acid copolymer"]. The use of localized physical crosslinks that are stable above $T_g$ or $T_m$ of the bulk polymer in these systems has never been investigated before.

Materials Based on Supramolecular Networks

The field of hydrogen-bonded supramolecular polymers and networks has gained considerable importance in recent years as a means to obtain thermoplastic elastomers with excellent mechanical properties at ambient temperature, but a sharp melting transition, and a low viscosity and excellent processing characteristics at moderately high temperatures [A. W. Bosman, R. P. Sijbesma, E. W. Meijer, Mater. Today 2004, 7, 34-39; B. J. B. Folmer, R. P. Sijbesma, R. M. Versteegen, J. A. J. van der Rijt, E. W. Meijer, Adv. Mater. 2000, 12, 874-878; R. P. Sijbesma, F. H. Beijer, L. Brunsveld, B. J. B. Folmer, J. H. K. K. Hirschberg, R. F. M. Lange, J. K. L. Lowe, E. W. Meijer, Science 1997, 278, 1601-1604]. The supramolecular polymers and networks described in the literature are typically composed of soft, low molecular weight linear telechelic polymers, functionalized with monodisperse end groups that reversibly dimerize via multivalent non-covalent interactions [S. Seiffert, J. Sprakel, Chem. Soc. Rev. 2012, 41, 909-930]. Multivalent self-complementary hydrogen-bonded ligands such as 2-ureido-4[1H]-pyrimidone, UPy, have proven to be particularly useful supramolecular motifs [0. J. G. M. Goor, S. I. S. Hendrikse, P. Y. W. Dankers, E. W. Meijer, Chem. Soc. Rev. 2017, DOI: 10.1039/C7CS00564D]. Below the dissociation temperature of the hydrogen-bonded dimers, the mechanical properties of the resulting supramolecular polymers reflect those of the corresponding high molecular weight polymers, but their melt viscosity is far lower. For instance, Meijer et al. reported poly(ethylene/butylene)

($M_w$ 3'500) with UPy end groups to give shape-persistent elastomers with a rubbery plateau and a room temperature plateau modulus G'≈1 MPa, and a low viscosity melt at temperatures above 90° C. [B. J. B. Folmer, R. P. Sijbesma, R. M. Versteegen, J. A. J. van der Rijt, E. W. Meijer, *Adv. Mater.* 2000, 12, 874-878].

Another useful supramolecular motif is the benzenetricarboxylic acid triamide (BTA) function. The intermolecular hydrogen bonding between the BTA groups have rendered them suitable for the realization of supramolecular polymers [S. Cantekin, T. F. A. de Greef, A. R. A. Palmans, *Chem. Soc. Rev.* 2012, 41, 6125-6137]. These types of polymers find increasing attention for the creation of advanced and complex soft matter systems. BTA groups have also been used as end groups for amorphous or semicrystalline telechelic polymers. In the case of hydrophobic polymers, phase segregation between the polymer and the BTA units readily occurred due to the preferential self-assembly of the latter into helical stacks, which gave rise to melting transitions as high as 200° C. for comparably low molecular weight base polymers ($M_n$≈4000) [T. Mes, M. M. J. Smulders, A. R. A. Palmans, E. W. Meijer, *Macromolecules* 2010, 43, 1981-1991]. The strong tendency of BTA units to self-assemble in bulk materials is further illustrated by their incorporation into the side chains of polyacrylates resulting in the stabilization of coiled chain conformations [T. Mes, R. van der Weegen, A. R. A. Palmans, E. W. Meijer, *Angew. Chem. Int. Ed.* 2011, 50, 5085-5089; N. Hosono, M. A. J. Gillissen, Y. Li, S. S. Sheiko, A. R. A. Palmans, E. W. Meijer, *J. Am. Chem. Soc.* 2013, 135, 501-510; N. Hosono, A. M. Kushner, J. Chung, A. R. A. Palmans, Z. Guan, E. W. Meijer, *J. Am. Chem. Soc.* 2015, 137, 6880-6888]. However, the mechanical properties of bulk materials, such as thermoplastic elastomers based on the BTA motif, have never been reported, with the exception of a hydrogel based on a BTA-based poly(ethylene oxide) [C. M. A. Leenders, T. Mes, M. B. Baker, M. M. E. Koenigs, P. Besenius, A. R. A. Palmans, E. W. Meijer, *Mater. Horiz.* 2014, 1, 116-120], and their thermal properties have remained unexplored. Moreover, low molecular weight BTA derivatives and related compounds have found a commercial application as nucleating agents, which serve to increase the crystallization temperature and improve the transparency of isotactic poly(propylene) at low additive content [M. Blomenhofer, S. Ganzleben, D. Hanft, H.-W. Schmidt, M. Kristiansen, P. Smith, K. Stoll, D. Mäder, K. Hoffmann, *Macromolecules* 2005, 38, 3688-3695; F. Abraham, S. Ganzleben, D. Hanft, P. Smith, H.-W. Schmidt, *Macrmol. Chem. Phys.* 2010, 211, 171-181]. However, the use of BTA as low-molecular-weight additives with specific interactions with polymer end and side groups has never been reported.

Supramolecular elastomers with higher moduli and/or higher transition temperatures may be obtained from multifunctional, branched or star-shaped polymers. Unlike classical TPEs based on block copolymers, the specific, non-covalent binding often gives elastomeric networks with sharp melting transitions, and even allows for dynamic network reorganization under equilibrium conditions. This may in turn lead to self-healing properties, reinforced elastomers, or thermoresponsive materials [B. J. B. Folmer, R. P. Sijbesma, R. M. Versteegen, J. A. J. van der Rijt, E. W. Meijer, *Adv. Mater.* 2000, 12, 874-878; R. F. M. Lange, M. Van Gurp, E. W. Meijer, *J. Polym. Sci., Part A: Polym. Chem.* 1999, 37, 3657-3670; S. Sivakova, D. A. Bohnsack, M. E. Mackay, P. Suwanmala, S. J. Rowan, *J. Am. Chem. Soc.* 2005, 127, 18202-18211; P. Cordier, F. Tournilhac, C. Soulie-Ziakovic, L. Leibler, *Nature* 2008, 451, 977-980; Y. Chen, A. M. Kushner, G. A. Williams, Z. Guan, *Nature Chem.* 2012, 4, 467-472]. Thus, polymer networks based on trifunctional poly(propylene oxide-co-ethylene oxide) ($M_w$ 6000) with UPy end groups show an elastomeric response with a pronounced rubbery plateau and a plateau modulus G'≈1 MPa. Similar properties have also been reported for networks based on poly(tetrahydrofuran) ($M_n$ 2000) with adenine end groups. In addition to the dimerization of these nucleobases by hydrogen-bonding, the dimers in this case also crystallized to give anisotropic "hard" domains owing to π-π stacking, which were postulated to contribute to both the modulus (G' ≈1 MPa) and the melting point (80° C.) [S. Sivakova, D. A. Bohnsack, M. E. Mackay, P. Suwanmala, S. J. Rowan, *J. Am. Chem. Soc.* 2005, 127, 18202-18211].

Supramolecular networks and elastomers based on end-functionalized linear or star-shaped poly(isobutylene) have received particular attention due to their low glass transition temperature and the hydrophobic, chemically inert nature of the poly(isobutylene) matrix, which results in significantly enhanced aggregation of hydrogen-bonded end groups. For example, Creton et al. investigated a low molecular weight poly (isobutylene) ($M_n$ 1'700) functionalized with bisurea ligands [J. Courtois, I. Baroudi, N. Nouvel, E. Degrandi, S. Pensec, G. Ducouret, C. Chaneac, L. Bouteiller, C. Creton, *Adv. Funct. Mater.* 2010, 20, 1803-1811]. The room temperature rheological properties of the resulting supramolecular polymer were those of a soft elastomer with a plateau modulus G' ≈0.1 MPa and a melting transition at 80° C. Similar materials properties have also been reported for analogous supramolecular materials based on poly(isobutylene) [F. Herbst, K. Schroter, I. Gunkel, S. Groger, T. Thurn-Albrecht, J. Balbach, W. H. Binder, *Macromolecules* 2010, 43, 10006-10016; F. Herbst, S. Seiffert, W. H. Binder, *Polym. Chem.* 2012, 3, 3084-3092; K. Hackethal, F. Herbst, W. H. Binder, *J. Polym. Sci., Part A: Polym. Chem.* 2012, 50, 4494-4506].

The common denominator of all of these previously described supramolecular elastomers is that they are based on networks that have been formed by linear or star-shaped polymers that have end groups carrying ligands capable of forming dimers, trimers, or small oligomers by means of supramolecular interactions. As a result, these ligands establish "point-to-point" connections between two, three, or perhaps a few polymer chains. In all of these cases, it is worth noting that the use of additives that are based on the same complementary supramolecular motifs inevitably results in competitive interactions that lead to a breakage of network points in supramolecular polymer networks and hence a weakening of the resulting elastomers [X. J. Loh, J. del Barrio, P. P. C. Toh, T.-C. Lee, D. Jiao, U. Rauwald, E. A. Appel, O. A. Sherman, *Biomacromolecules* 2012, 13, 84-91]. A positive effect of such additives on the thermal and mechanical stability of supramolecular elastomers has never been reported.

There are examples of materials based on poly(ε-caprolactone) with a central core comprising two urea functions that can self-assemble into ribbon-like structures through bifurcate H-bonding. The addition of low molecular weight additives based on the same core was found to enhance the formation of the supramolecular ribbons resulting in a stiffer material with a Young's modulus doubled at 7 wt % content of the additive [E. Wisse, L. E. Govaert, H. E. H. Meijer, E. W. Meijer, *Macromolecules* 2006, 39, 7425-7432; E. Wisse, A. J. H. Spiering, F. Pfeifer, G. Portale, H. W. Siesler, E. W. Meijer, *Macromolecules* 2009, 42, 524-530]. A concomitant effect of the presence of additives on the melting temperatures could not be observed, which can be attributed to the absence of network formation in this monofunctional system.

In summary, supramolecular polymers networks based on hydrogen-bond ligands give rise to TPEs with sharp melting transitions, and often excellent elastic behavior at room temperature and at small strains. However, their shear moduli G' typically do not exceed 1 MPa and, most importantly, softening temperatures, $T_s$, which are dependent on the melting or disaggregation temperatures of the hydrogen-bonded ligands, are typically below 100° C., so that their maximum operating temperatures are insufficient for many technological applications. The materials described above do not even allow for modifications of their thermomechanical properties by use of additives based on complementary supramolecular interactions, as these would result in a breakage of the network points due to competitive intermolecular interactions. The development of novel TPEs that combine high moduli, high operating temperatures, excellent elasticity, low hysteresis, and shape recovery at large strains remains an outstanding challenge.

Oligopeptide-Modified Polymers and Related Materials

The well-understood self-assembly of ligands based on self-complementary, electronically conjugated, ditopic hydrogen bonded donor and acceptor groups, such as peptides, amides, urethanes, or ureas may provide solutions to the shortcomings of existing materials, particularly in the case of oligomers such as β-sheet-forming oligopeptides that form 1D or 2D extended nanoscopic aggregates by cooperative self-assembly [D. I. Bower, *An Introduction to Polymer Physics*, Cambridge University Press, 2002; I. A. Nyrkova, A. N. Semenov, A. Aggeli, N. Boden, *Eur. Phys. J. B* 2000, 17, 481-497]. It has been amply demonstrated that polymer-substituted β-sheet forming oligopeptides give rise to well-defined nanostructures [L. Tian, E. Croisier, H. Frauenrath, *Chimia* 2013, 67, 782-787].

However, most previous work has focused on biomaterials and biomedical applications and has therefore typically been concerned with water-processable systems, such as poly(ethylene oxide)-functionalized oligopeptides [J. Hentschel, H. G. Börner, *J. Am. Chem. Soc.* 2006, 128, 14142-14149; J. Hentschel, E. Krause, H. G. Börner, *J. Am. Chem. Soc.* 2006, 128, 7722-7723; D. Eckhardt, M. Groenewolt, E. Krause, H. G. Börner, *Chem. Commun.* 2005, 2814-2816]. Very few reports have so far been published on the mechanical properties of bulk materials obtained from soft polymers with β-sheet-forming oligopeptide end groups. For instance, Sogah et al. investigated the mechanical properties of multiblock copolymers of poly(ethylene oxide) segments and short linear or pre-organized β-sheet-forming oligopeptides, inspired by silk materials [M. J. Winningham, D. Y. Sogah, *Macromolecules* 1997, 30, 862-876; O. Rathore, D. Y. Sogah, *Macromolecules* 2001, 34, 1477-1486; O. Rathore, D. Y. Sogah, *J. Am. Chem. Soc.* 2001, 123, 5231-5239; O. Rathore, M. J. Winningham, D. Y. Sogah, *J. Polym. Sci., Part A: Polym. Chem.* 2000, 38, 352-366]. These authors reported the formation of β-sheet-like aggregates, and enhanced mechanical properties compared to pure poly(ethylene oxide). Börner et al. investigated nanofibrils of poly(butyl acrylate) with oligopeptide end groups dispersed in high molecular weight poly(butyl acrylate), which resulted in a material with a low loss factor tan δ≤0.3 and an increase in plateau modulus to about G' ≈0.1 MPa [J. Hentschel, H. G. Börner, *Macromol. Biosci.* 2009, 9, 187-194]. Since all of these previous examples have in fact focused on monofunctional polymers (with only one oligopeptide end group) limited to network formation by entanglement of the nanostructures, the resulting mechanical properties have hence remained inferior to those of simple hydrogen-bonded supramolecular elastomers (see above) and even standard TPE, in spite of the claimed formation of nanofibrillar aggregates.

Unlike all previous investigations of oligopeptide-based supramolecular elastomers, our own previous investigations have focused on mixtures of monofunctional and difunctional polymers with short, β-sheet-forming oligopeptide end groups. Our work has clearly demonstrated that the mechanical properties of the resulting elastomers may be tailored over a wide range of target moduli, loss factors, and transition temperatures, depending on the choice and combination of the oligopeptide end groups [E. Croisier, S. Liang, T. Schweizer, S. Balog, M. Mionić, R. Snellings, J. Cugnoni, V. Michaud, H. Frauenrath, *Nat. Commun.* 2014, 5, 4728; E. Croisier, *From Reinforcement to High-Performance Damping*, EPFL PhD Thesis 5861, 2013; S. Liang, *Damping Materials from Hierarchically Structured Oligopeptide-Modified Polymer Blends*, EPFL PhD Thesis 6648, 2015; E. Croisier, H. Frauenrath, S. Liang, V. Michaud, EPFL, WO 2014080043, "Blends of oligopeptide terminal poly(isobutylene) or poly(styrene)"]. We have shown that hydrogen bonding between the oligopeptides in the hydrophobic environment of a bulk material based e.g. on oligopeptide-modified poly(isobutylene) is strong, so that oligopeptides with 1-4 amino acid units (2~5 peptide groups) may give materials with high softening temperatures. For example, elastic materials with loss factors tan δ≤0.2 at temperatures up to 65° C., and plateau moduli of up to G' ≈5 MPa were achieved. Moreover, even materials with higher softening temperatures were achieved.

However, the softening temperatures become progressively lower and the transitions broader when the molar mass of the polymer segments tethered to the oligopeptides is increased. This is because negative contributions from the conformational entropy of the tethered polymer chains to the free energy of association of the β-sheet-forming oligopeptide end groups are expected to increase with increasing molar mass. The reduction in conformational entropy may be associated with confinement both by the substrate (in this case β-sheet fibrils or tapes formed by the oligopeptide groups) and by adjacent chains, in the case of a large number of tethered polymer segments per unit surface of the substrate, in this case, the aggregates formed from the oligopeptides. Self-assembly may also be increasingly kinetically hindered for increasing molar masses of the polymers tethered to the oligopeptides as the viscosity of the polymer matrix increases. This is a severe shortcoming of such systems because molecular weights well in excess of several times the entanglement length are required for both elastomers and thermoplastic materials, if they are to show sufficient ductility, strength and toughness for practical applications.

It is an objective of the present invention to improve the temperature range of operation and/or the toughness of thermoplastic polymers and TPEs in comparison to classical thermoplastics and TPEs. A further objective is to provide materials from low-cost commodity polymers for high-temperature applications, particularly for the automotive industry, electronics industry, and the medical sector. A particular objective of the present invention is to provide TPEs from inexpensive commodity polymers with a glass transition temperature $T_g$ below the operating temperature T, with molecular weights well-above several multiples of their respective entanglement molecular weights, and softening temperatures $T_s$ significantly above the operating temperature T, preferably above 150° C. An additional objective is to increase the form stability of amorphous or semicrystalline thermoplastic polymers at elevated operating temperatures T well above their respective glass transition temperature $T_g$ or melting temperatures $T_m$. A further objective is to provide such amorphous or semicrystalline thermoplastic polymers with increased form stability at elevated temperatures that have an improved toughness in tensions and/or upon impact.

SUMMARY OF THE INVENTION

By using the present invention, some or all of the drawbacks of the prior art can be overcome. In particular, some or all of the difficulties and drawbacks of the prior art can be overcome by the composition of claim 1, the method of claim 23, the use of claim 26, the use of claim 28, and the sheets, fibers or molded parts of claim 29. In particular, by using the present invention, an increase of the operating temperature range of thermoplastic polymers and TPEs based on commodity polymers can be achieved while, at the same time, their respective mechanical properties can be improved, which significantly broadens the scope of their applications.

Figure 2:
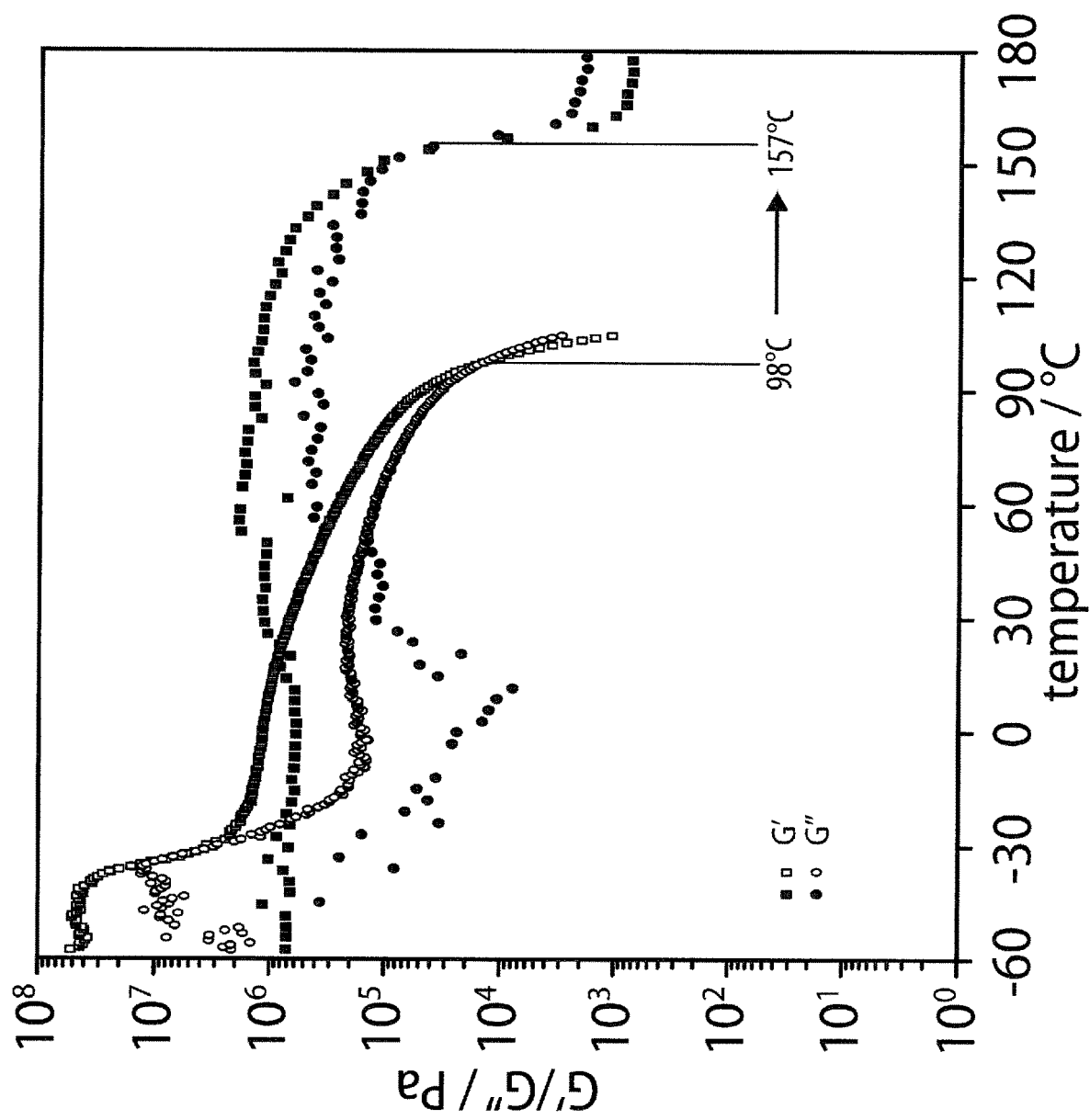
Figure 3:
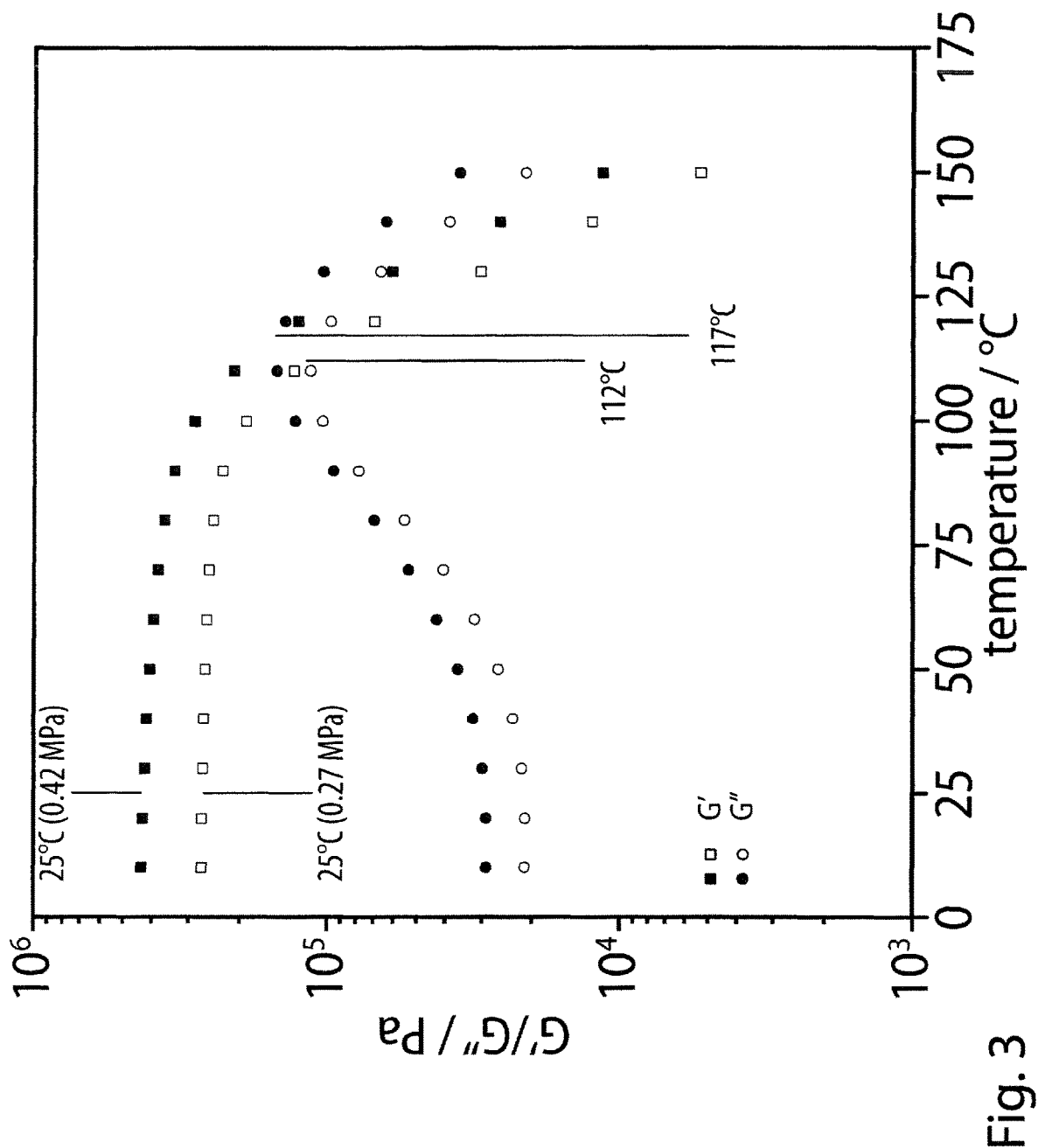
Figure 4:
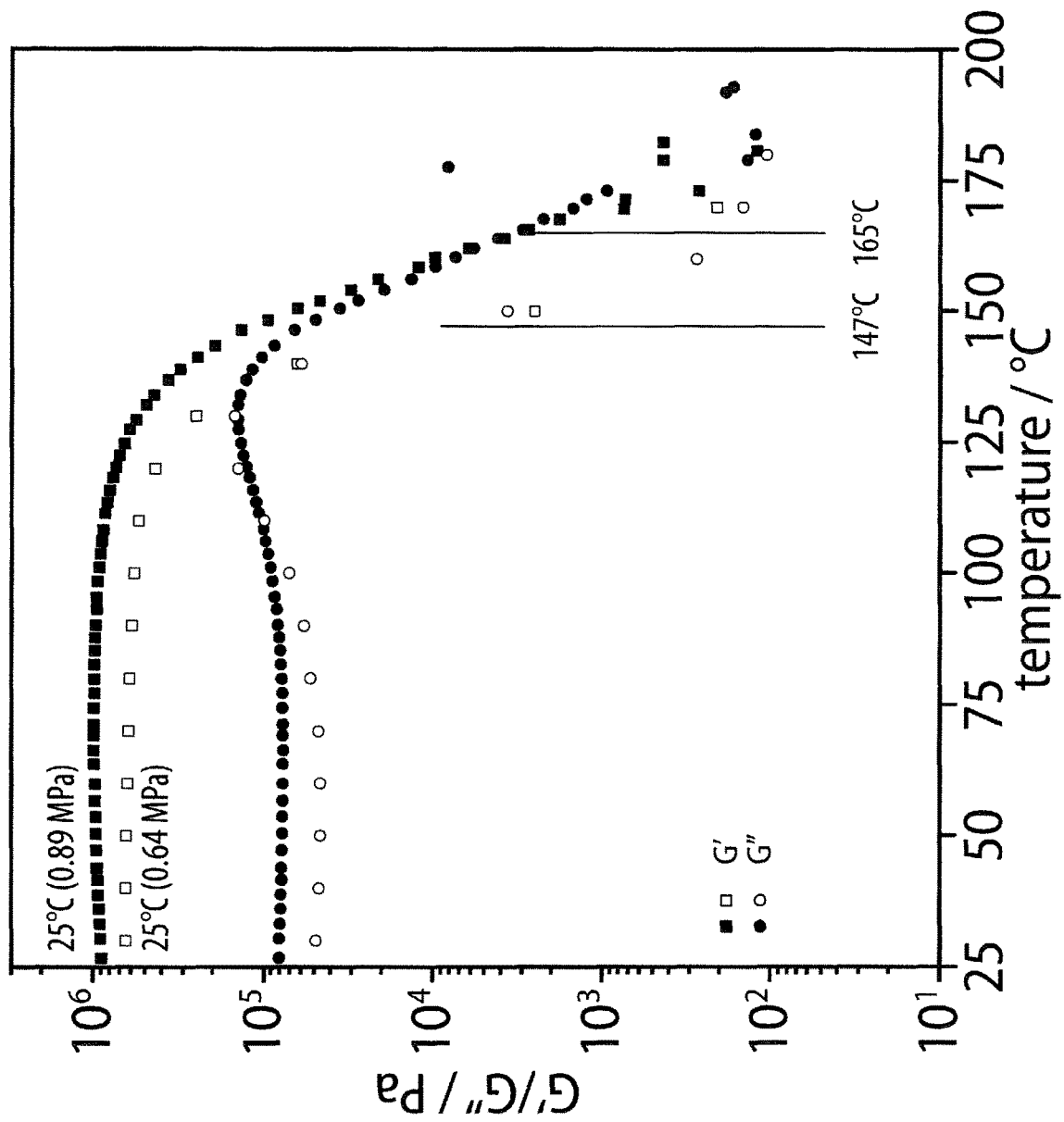
Figure 5:
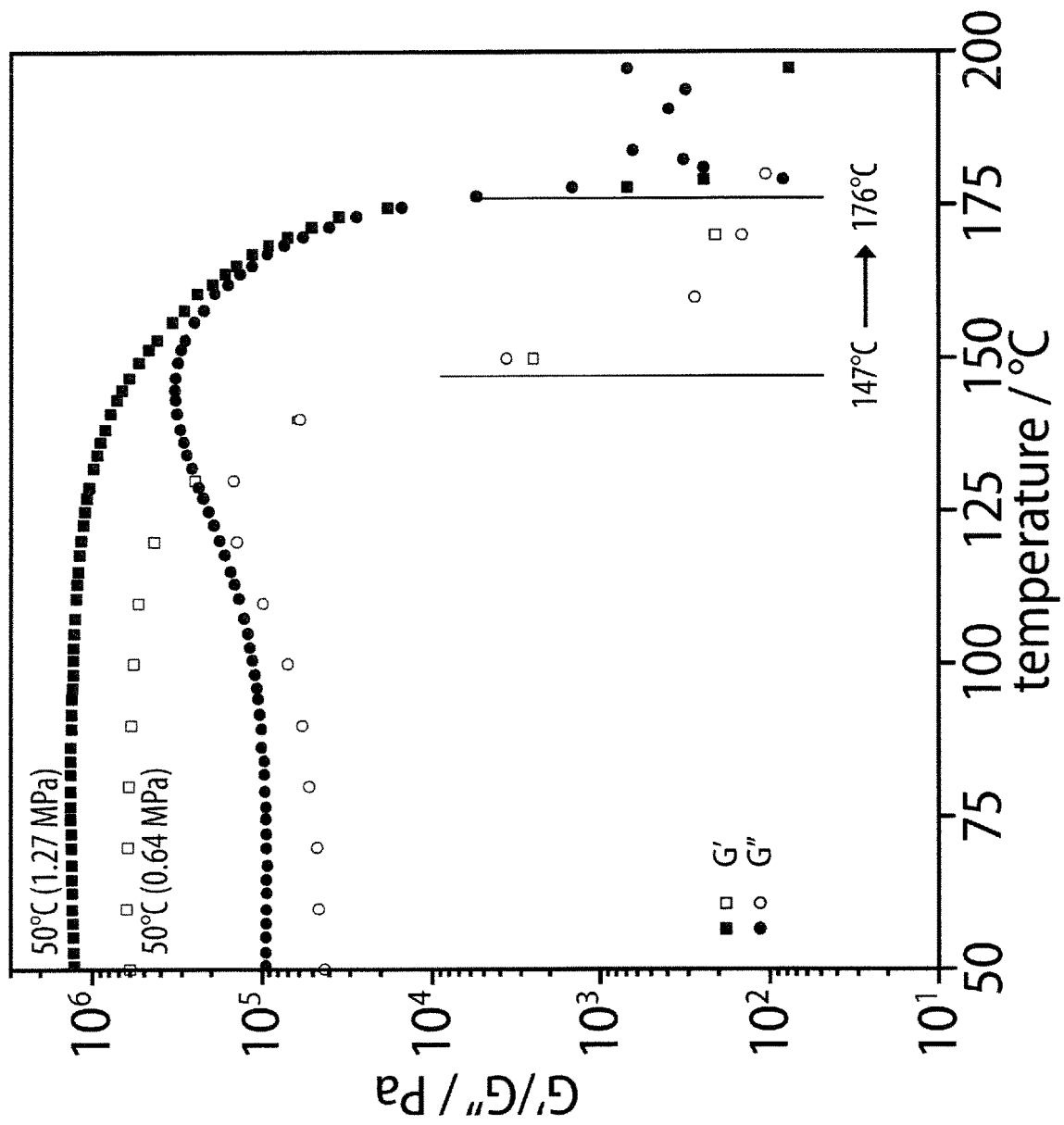
Figure 6:
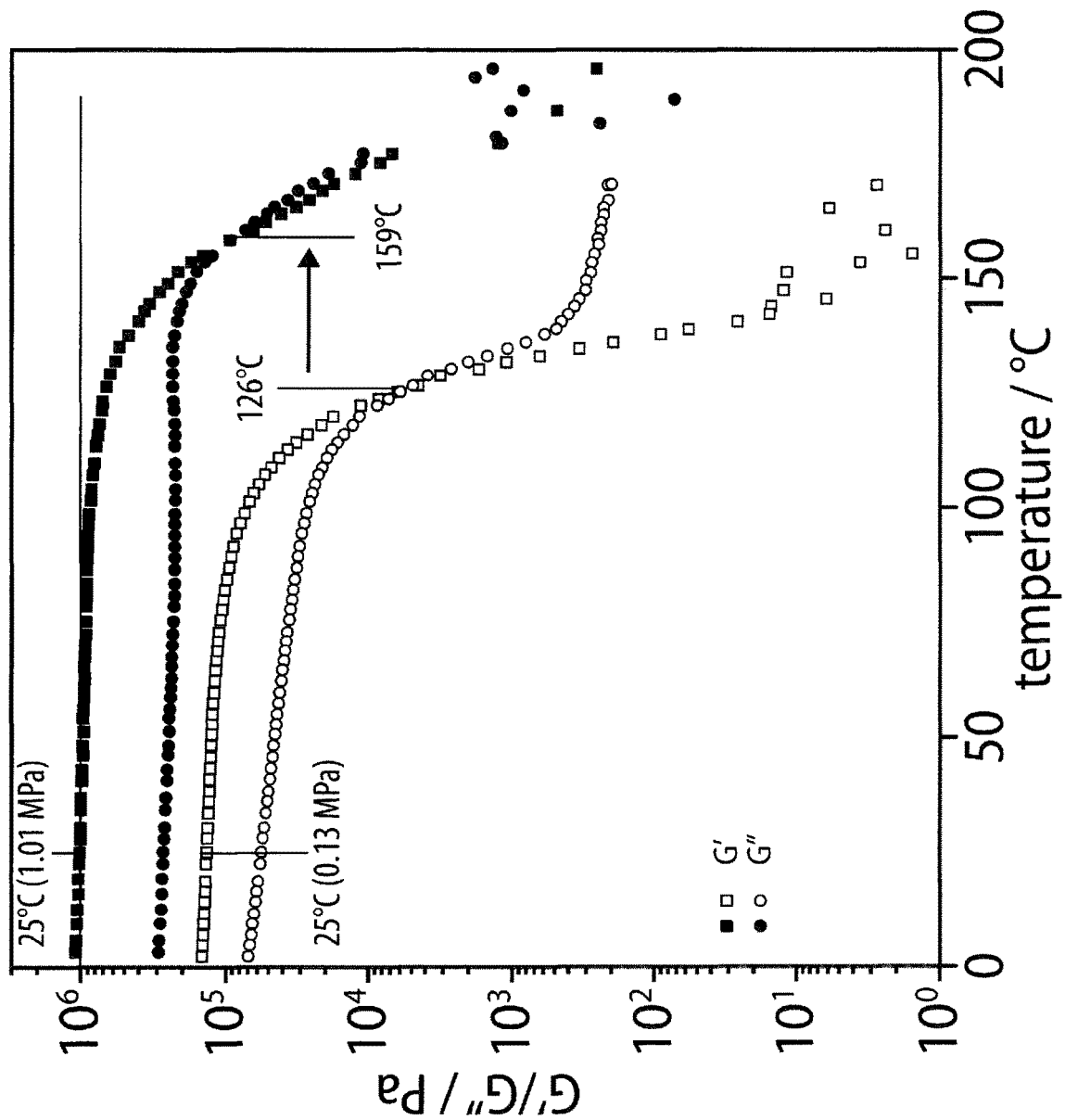

FIG. 1 shows a schematic and exemplary overview of how the composition according to the invention can be obtained, FIG. 2 shows a graph of rheology measurements of a pure functionalized polymer and of a composition according to the invention, FIG. 3 shows a graph of rheology measurements of a pure functionalized polymer and of a composition according to the invention, FIG. 4 shows a graph of rheology measurements of a pure functionalized polymer and of a composition according to the invention, FIG. 5 shows a graph of rheology measurements of a pure functionalized polymer and of a composition according to the invention, FIG. 6 shows a graph of rheology measurements of a pure functionalized polymer and of a composition according to the invention.

The present invention provides a composition containing
a. a functionalized polymer 10 that comprises at least one polymer segment 13 and at least two polymer aggregating segments 11, 12 capable of forming non-covalent bonds based on a supramolecular interaction,
b. an aggregating additive 20 that comprises at least one additive aggregating segment 21 capable of forming non-covalent bonds based on the same supramolecular interaction as the polymer aggregating segments 11, 12,
wherein the polymer aggregating segments 11, 12 and the additive aggregating segment 21 are ditopic,
wherein the polymer aggregating segments 11, 12 and the additive aggregating segment 21 are designed such that they can form aggregates 31 that contain polymer aggregating segments 11, 12 and additive aggregating segments 21, and wherein the aggregating additive 20 has a molecular weight of from 50 g/mol to 2000 g/mol.

A ditopic segment contains at least two interaction sites from which non-covalent bonds can be formed, wherein the segment contains at least one unsaturated interaction site when the segment has already formed an aggregate with another segment. Preferably, a ditopic segment is a segment that contains two bonding regions each comprising at least one interaction site capable of forming non-covalent bonds, wherein the bonding regions are arranged such that the at least one interaction site of one of the bonding regions remains unsaturated when the segment has already formed an aggregate with another segment via the other bonding region. Preferably, the at least two interactions sites of a ditopic segment are distributed over the two bonding regions. Ditopic segments can particularly aggregate with two other segments. The non-covalent bonds formed in one of the bonding regions of the segment can be based on the same or on a different supramolecular interaction as the non-covalent bonds formed in the other bonding region. Preferably, non-covalent bonds formed in one of the bonding regions of the ditopic segment are based on the same supramolecular interaction as the non-covalent bonds formed in the other bonding region. Thus, according to an embodiment of the invention, the polymer aggregating segments 11, 12 and the additive aggregating segment 21 are ditopic, wherein the non-covalent bonds formed in one of the bonding regions of the ditopic segment are based on the same supramolecular interaction as the non-covalent bonds formed in the other bonding region. More preferably, the angle between the non-covalent bonds formed from two interaction sites of a ditopic segment is from 90° to 180°, more preferably from 170° to 180°. This helps in forming aggregates 31 that extend in at least one direction. The non-covalent bonds formed from the interaction sites can be preferably based on the same or on a different supramolecular interaction, preferably they are based on the same supramolecular interaction. An example for a ditopic segment is an oligopeptide, such as dialanine, or a multifunctional cyclic moiety containing one or more —C(=O)—NH— groups such as benzene tricarboxamide. In an oligopeptide and in a multifunctional cyclic moiety containing one or more —C(=O)—NH— groups, the —C(=O)— and —NH— groups are distributed over the two bonding regions of the oligopeptide or of the multifunctional cyclic moiety, which allows for aggregation via these two bonding regions independently of one another.

Without wishing to be bound by scientific theory, it is believed that the polymer aggregating segments 11, 12 of the functionalized polymer 10 and the additive aggregating segment 21 of the aggregating additive 20 form aggregates via non-covalent bonds based on the same supramolecular interaction shared by the polymer aggregating segments 11, 12 and the additive aggregating segment 21. The aggregates are believed to be extended in at least one and at most two directions, to be of nanoscopic size in at most two and at least one direction, and to be well-dispersed in the composition. In this way, it is believed that these aggregates serve as physical cross-links in the composition. Without wishing to be bound by scientific theory, it is believed that, because the functionalized polymer 10 comprises at least two polymer aggregating segments 11, 12, these physical crosslinks form a network, which improves the mechanical properties and helps to increase the softening temperatures of these compositions.

It is believed that the aggregating additives 20 serve the primary purpose to establish certain minimum concentrations of aggregating segments, particularly in case of the higher molecular weight polymers, so that nanostructure formation based on their self-complementary interactions is reinforced. It is believed that, because the aggregating additive 20 has a molecular weight of from 50 g/mol to 2000 g/mol, compositions with a high and sharp softening point can be achieved, as a high concentration of the aggregating segments 11, 12, 21 can be achieved at low contents of the aggregating additive 20.

As a result of the present invention, the softening temperatures of the composition and, thus, the materials obtained from the composition, can be increased with increasing amount of additive. This observation has never been reported in the literature. In contrast, polymers with supramolecular self-assembly motifs at the terminal groups have always been shown to break apart upon addition of identical/similar self-assembly motifs due to competitive interaction, and no significant impact on softening temperatures could be observed when low molecular weight additives were used to reinforce nanostructure formation in polymers comprising only one central self-assembling core (see Background).

With the present invention, it is possible to adjust the total concentration of the combined segments capable of non-covalent bonding of the functionalized polymer 10 and the aggregating additive 20 in the composition independently of the molecular weight of the functionalized polymer 10. As a result, the softening temperature of the resulting material can be chosen irrespective of the nature and the molecular weight of the functionalized polymer 10 and independently of its mechanical properties. Moreover, the nanoscopic size of the aggregates formed by co-assembly of the polymer aggregating segments 11, 12 and the additive aggregating segment 21, and their good dispersion in the composition are believed to ensure that the mechanical and thermal stability of the aggregates is significantly higher than that of physical cross-links in classical TPEs, at equal or even significantly lower weight fractions.

DETAILED DESCRIPTION OF THE INVENTION

The present invention provides a composition containing
a. a functionalized polymer 10 that comprises at least one polymer segment 13 and at least two polymer aggregating segments 11, 12 capable of forming non-covalent bonds based on a supramolecular interaction,
b. an aggregating additive 20 that comprises at least one additive aggregating segment 21 capable of forming non-covalent bonds based on the same supramolecular interaction as the polymer aggregating segments 11, 12,
wherein the polymer aggregating segments 11, 12 and the additive aggregating segment 21 are ditopic,
wherein the polymer aggregating segments 11, 12 and the additive aggregating segment 21 are designed such that they can form aggregates 31 that contain polymer aggregating segments 11, 12 and additive aggregating segments 21, and
wherein the aggregating additive 20 has a molecular weight of from 50 g/mol to 2000 g/mol.

According to a preferred embodiment, the invention provides for a composition containing
a. a functionalized polymer 10 that comprises at least one polymer segment 13 and at least two polymer aggregating segments 11, 12 capable of forming non-covalent bonds based on a supramolecular interaction,
b. an aggregating additive 20 that comprises at least one additive aggregating segment 21 capable of forming non-covalent bonds based on the same supramolecular interaction as the polymer aggregating segments 11, 12,
wherein the polymer aggregating segments 11, 12 and the additive aggregating segment 21 are ditopic,
wherein the polymer aggregating segments 11, 12 and the additive aggregating segment 21 are designed such that they can form aggregates 31 that contain polymer aggregating segments 11, 12 and additive aggregating segments 21, and
wherein the aggregating additive 20 has a molecular weight of from 50 g/mol to 1300 g/mol.

According to another preferred embodiment, the invention provides for a composition containing
a. a functionalized polymer 10 that comprises at least one polymer segment 13 and at least two polymer aggregating segments 11, 12 capable of forming non-covalent bonds based on a supramolecular interaction,
b. an aggregating additive 20 that comprises at least one additive aggregating segment 21 capable of forming non-covalent bonds based on the same supramolecular interaction as the polymer aggregating segments 11, 12,
wherein the polymer aggregating segments 11, 12 and the additive aggregating segment 21 are ditopic,
wherein the polymer aggregating segments 11, 12 and the additive aggregating segment 21 are designed such that they can form aggregates 31 that contain polymer aggregating segments 11, 12 and additive aggregating segments 21, and
wherein the aggregating additive 20 has a molecular weight of from 50 g/mol to 1000 g/mol.

According to another embodiment of the invention, the aggregating additive 20 is monodisperse.

Preferably, for a monodisperse compound, all molecules in a sample of the compound are uniform. For example, all molecules have the same molecular weight with the exception of molecular weight differences caused by the incorporation of different isotopes. For example, ethane is a monodisperse compound, whereas polystyrene is not. Preferably, for a monodisperse residue in a compound, this residue is uniform in all molecules of a sample of a compound. For example, in the amine ($C_2H_5$)—NH-polystyrene, the ethyl residue is monodisperse, whereas the polystyrene residue is not.

According to another preferred embodiment, the invention provides for a composition containing
a. a functionalized polymer 10 that comprises at least one polymer segment 13 and at least two polymer aggregating segments 11, 12 capable of forming non-covalent bonds based on a supramolecular interaction,
b. an aggregating additive 20 that comprises at least one additive aggregating segment 21 capable of forming non-covalent bonds based on the same supramolecular interaction as the polymer aggregating segments 11, 12,
wherein the polymer aggregating segments 11, 12 and the additive aggregating segment 21 are ditopic,
wherein the polymer aggregating segments 11, 12 and the additive aggregating segment 21 are designed such that they can form aggregates 31 that contain polymer aggregating segments 11, 12 and additive aggregating segments 21, and
wherein the aggregating additive 20 has a molecular weight of from 50 g/mol to 2000 g/mol and the aggregating additive 20 is monodisperse.

According to an embodiment of the invention, the composition contains a further polymer that is preferably unfunctionalized. If the composition contains a further polymer, this polymer is more preferably of the same type as the polymer segment 13 of the functionalized polymer 10. The optional further polymer is also described in more detail below. For example, if the polymer segment 13 of the functionalized polymer 10 is poly(isobutylene), the further polymer is preferably poly(isobutylene).

Structure of the Functionalized Polymer 10

The functionalized polymer 10 can have different architectures. For example, it may be a linear polymer or a multiarm star polymer. Preferably, the functionalized polymer is a linear polymer. The functionalized polymer 10 may comprise the at least two polymer aggregating segments 11, 12 along the backbone of the functionalized polymer 10, as terminal groups, or as side groups. Preferably, the functionalized polymer 10 comprises the at last two polymer aggregating segments 11, 12 as terminal groups. According to an embodiment of the invention, the functionalized polymer 10 is a linear polymer and/or comprises two polymer aggregating segments 11, 12, in particular as terminal groups. According to another embodiment of the invention, the functionalized polymer 10 is a linear difunctional polymer comprising two polymer aggregating segments 11, 12, wherein the two polymer aggregating segments 11, 12 are terminal groups of the functionalized polymer 10. For example, the functionalized polymer 10 may have the structure X-Q-X, wherein X represents the polymer aggregating segments 11, 12 and Q represents the polymer segment 13. Linear difunctional polymers comprising two polymer aggregating segments 11, 12 as terminal groups, in particular with a structure X-Q-X, wherein X represents the polymer aggregating segments 11, 12 and Q represents the polymer segment are synthetically most straightforward to access.

According to another embodiment of the invention, the functionalized polymer 10 can be a multiarm star polymer. In this case, it is preferable that every arm of the polymer comprises a polymer aggregating segment, preferably as terminal group of the arm. For example, the functionalized polymer 10 may have the structure $E(-Q-X)_m$ with m=2-6 polymer arms Q-X grafted to a central core E, wherein Q and X are as defined above. The central core E may be a trifunctional, tetrafunctional, pentafunctional or hexafunctional unit. Multiarm star polymers can be obtained via standard living polymerization protocols known to the skilled person, using either multifunctional initiators or multifunctional quenching agents [J. M. Ren, T. G. McKenzie, Q. Fu, E. H. H. Wong, J. Xu, Z. An, S. Shanmugam, T. P. Davis, C. Boyer, G. G. Qiao, Chem. Rev. 2016, 116, 6743-6836]. For example, living polymer chains synthesized by living anionic polymerization techniques can be conveniently linked to a central core E by termination with chlorosilanes such as $Me_2SiCl_2$, $MeSiCl_3$, and $SiCl_4$ or benzene derivatives bearing two or more chloromethyl or bromomethyl substituents, resulting in cores E=$Me_2Si$, MeSi, Si, or $C_6H_4(CH_2)_2$, $C_6H_3(CH_2)_3$, $C_6H_2(CH_2)_4$, respectively [N. Hadjichristidis, M. Pitsikalis, S. Pispas, H. Iatrou, Chem. Rev. 2001, 101, 3747-3792]. In the multiarm star polymer architectures, the branching points may serve as covalent network points to increase the overall network density without affecting the melt processability and recyclability of the material.

According to another embodiment of the invention, the functionalized polymer 10 comprises the at least two polymer aggregating segments 11, 12 as side groups, in particular as side groups along the polymer segment 13 of the functionalized polymer 10. In this case, the functionalized polymer 10 may comprise more than 2 polymer aggregating segments 11, 12, in particular 3 to 100 segments capable of forming non-covalent bonds. A polymer with this architecture may be called a side-functional polymer. For example, the functionalized polymer 10 can be a side-functional polymer with the structure $U'_x$-ran-$(U''(—X))_y$, that is, a random copolymer of repeating units U' and repeating units U" carrying the segment X capable of forming covalent bonds.

According to an embodiment of the invention, the functionalized polymer 10 is a linear or a multiarm star copolymer as defined above and the composition further contains a side-functional polymer as defined above. In this way, the concentration of polymer aggregating segments 11, 12 can be increased locally in a simple way.

The mechanical properties of the materials obtained from the composition according to the invention are strongly dependent on the molecular weight of the functionalized polymer 10. Since, as a consequence of the chosen approach, the softening temperature of the material no longer depends on the molecular weight of the polymer matrix, the molecular weight of the functionalized polymer 10 can be chosen from a broad range of molecular weights, for instance a number average molecular weight $M_n$=1000 g/mol to 1000000 g/mol. Thus, according to an embodiment of the invention, the functionalized polymer 10 has a number average molecular weight of from 1000 g/mol to 1000000 g/mol, in particular of from 2000 g/mol to 100000 g/mol or from 10000 g/mol to 50000 g/mol.

In the functionalized polymer 10 the main part of the molecular weight is preferably contributed by the polymer segment 13. The at least two polymer aggregating segments 11, 12 are preferably designed such that they make a small contribution to the molecular weight of the functionalized polymer 10. Thus, according to an embodiment of the invention, the polymer segment 13 has a number average molecular weight of from 1000 g/mol to 1000000 g/mol, in particular of from 2000 g/mol to 100000 g/mol or from 10000 g/mol to 50000 g/mol. Preferably however, the lower limit of the molecular weight of the polymer segment 13 is well above the entanglement molecular weight of the respective polymer in order to account for good elastic behavior of the material; more preferably, the lower limit of the molecular weight of the polymer segment 13 is at least five times the entanglement molecular weight of the respective polymer, so that an entanglement network can be formed.

The entanglement molecular weights differ from polymer type to polymer type, but are typically on the order of $M_e$=2000 g/mol to 19000 g/mol (in each case number average molecular weights). Examples of entanglement molecular weights can be found in L. J. Fetters, D. J. Lohse, R. H. Colby, Chain Dimensions and Entanglement Spacings, in Physical Properties of Polymers Handbook, $2^{nd}$ edition, J. E. Mark, ed., Ch. 25, 2007; Polymer Handbook, $4^{th}$ edition, J. Brandrup, E. H. Immergut, E. A. Grulke, eds, Wiley, 2003; e.g., PE, $M_e$≈1000 g/mol; PIB, $M_e$≈6700-10000 g/mol; HPI, $M_e$≈2860-18000 g/mol, PI, $M_e$≈6000 g/mol; PB, $M_e$≈2000-4000 g/mol; atactic PMMA, $M_e$≈12'500 g/mol; atactic PS, $M_e$≈19000 g/mol.

Even more preferably, the lower limit of the molecular weight of the polymer segment 13 exceeds the molecular weight threshold where the changes in mechanical properties with increasing molecular weight start to level off, so well above a number average molecular weight $M_n$=20000 g/mol to 30000 g/mol. At the same time, in order to not reduce the concentration of the polymer aggregating segments 11, 12 more than necessary (which would require the addition of more aggregating additive 20), the preferred molecular weight of polymer segment 13 should not be chosen too far above the molecular weight threshold where the changes in mechanical properties with increasing molecular weight start to level off, because further molecular weight increases typically do not result in changed properties. Hence, preferred number average molecular weights for the polymer segment 13 are $M_n$=2000 g/mol to 100000 g/mol, and even more preferred are $M_n$=10000 g/mol to 50000 g/mol.

Various kinds of polymers are suitable as polymer segment 13. If the co-assembly of the polymer aggregating segments 11, 12 and the additive aggregating segments 21 is based on hydrogen bonding, the polymer segment 13 is preferably hydrophobic so that hydrogen bonding interactions in the bulk material are not impeded by a competition with water or other hydrophilic agents and hence stronger compared to hydrophilic polymer materials. This ensures that both the length of the polymer aggregating segments 11, 12 and the additive aggregating segment 21 as well as their required total concentration can be chosen as low as possible for a given binding strength and softening temperature, which is beneficial for the elastic properties of the material.

According to an embodiment of the invention, the polymer segment 13 is selected from the group consisting of polyolefins, in particular poly(isoprene) (PI), hydrogenated poly(isoprene) (HPI), poly(butadiene) (PB), hydrogenated poly(butadiene) (HPB), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP); polysiloxanes, in particular poly(dimethylsiloxane) (PDMS); polyesters, in particular poly(glycolide) (PGA), amorphous or semicrystalline poly(lactide) (PLA), poly(3-hydroxybutyrate) (P3HB), poly(ethylene adipate), poly(ethylene succinate); polyethers, in particular poly(ethylene oxide) (PEO), poly(propylene oxide) (PPO), poly(tetrahydrofuran) (PTHF); and polyacrylates and polymethacrylates, in particular poly(butyl acrylate) (PBuA), poly(methyl methacrylate) (PMMA), and poly(ethylene-co-acrylate)s.

Moreover, the kind of polymer used for the polymer segment 13 also depends on the purpose the resulting material should serve, in particular on the service temperature at which the material is normally used. Thus according to an embodiment of the invention, the polymer segment 13 is selected from the group consisting of poly(isoprene) (PI), hydrogenated poly(isoprene) (HPI), poly(butadiene) (PB), hydrogenated poly(butadiene) (HPB), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), and polysiloxanes, in particular poly(dimethylsiloxane) (PDMS), soft polyesters, in particular poly(glycolide) (PGA), poly(ethylene adipate), poly(ethylene succinate), polyethers, in particular poly(ethylene oxide) (PEO), poly(propylene oxide) (PPO), poly(tetrahydrofuran) (PTHF), polyacrylates, in particular poly(butyl acrylate) (PBuA); and poly(ethylene-co-acrylate)s. C. Compositions in which the functionalized polymer 10 comprises a polymer segment 13 selected from the aforementioned polymers may particularly serve as thermoplastic elastomers with tailored softening temperatures.

According to another embodiment of the invention, the polymer segment 13 is selected from the group consisting of amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP); polymethacrylates, in particular poly(methyl methacrylate) (PMMA); and polyesters, in particular amorphous poly(lactide) (PLA), in particular poly(L-lactide) (PLLA) with high contents of D-lactide, semicrystalline poly(lactide) (PLA), in particular poly(L-lactide) (PLLA), poly(3-hydroxybutyrate) (P3HB); and semicrystalline polyethers. Compositions in which the functionalized polymer 10 comprises a polymer segment 13 selected from the aforementioned polymers may particularly serve as thermoplastic polymers with increased form stability at elevated temperatures.

Structure of the Additives

The aggregating additive 20 contains at least one additive aggregating segment 21 capable of forming non-covalent bonds based on the same supramolecular interaction as the polymer aggregating segments 11, 12. The aggregating additive 20 may contain more than one additive aggregating segment 21 capable of forming non-covalent bonds, for example two, three, four, or five additive aggregating segments 21. If the aggregating additive 20 contains more than one additive aggregating segment 21, these additive aggregating segments 21 may be different from each other or identical, preferably they are identical. According to an embodiment of the invention, the aggregating additive 20 contains multiple additive aggregating segments 21 attached as side groups to a polymer segment. According to another embodiment of the invention, the aggregating additive 20 contains 2 to 5, in particular 2 to 4, additive aggregating segments 21. According to another embodiment of the invention, the aggregating additive 20 contains one additive aggregating segment 21. Aggregating additives 20 containing one additive aggregating segment 21 are easily accessible. Moreover, they can be more easily dispersed in the composition according to the invention.

In addition to the at least one additive aggregating segment 21, the aggregating additive 20 may comprise one or more additional groups 22. These additional groups 22 may serve various purposes, for example, to increase the solubility of the aggregating additive 20 in the composition, but they may also serve other purposes, for example imparting another functionality such as flame retardancy. Preferably, the additional groups 22 do not interfere with the capability of the additive aggregating segment 21 of the aggregating additive 20 to form aggregates with the polymer aggregating segments 11, 12 and/or with other additive aggregating segments 21 of other aggregating additives 20. More preferably, the additional groups 22 serve to increase the solubility of the aggregating additive 20 in the composition. Advantageously, the additional groups are miscible with the polymer segment 13 of the functionalized polymer 10. According to an embodiment of the invention, the aggregating additive 20 comprises at least one additional group 22. According to another embodiment of the invention, the aggregating additive 20 comprises two additional groups 22. If the aggregating additive 20 comprises more than one additional group, these groups may be different from each other or identical, preferably they are different from each other.

Additional groups 22 in the aggregating additive 20 may be incorporated into the aggregating additive 20 in different ways. For example, they may be incorporated as terminal groups, as side groups or as groups within the backbone of the aggregating additive 20. The aggregating additive 20 may have a linear structure or may have a structure based on a multifunctional cyclic or polycyclic and/or branched moiety. According to an embodiment of the invention, the aggregating additive 20 comprises at least one, in particular 2 to 6, additional groups 22, in particular as terminal groups. The additional groups 22, in particular the terminal groups 22, of the aggregating additive 20 may be different from each other or identical. An aggregating additive 20 with a linear structure advantageously comprises two additional groups 22, in particular two terminal groups 22, wherein the additional groups 22, in particular the terminal groups 22, are preferably different from each other. An aggregating additive with a structure based on a multifunctional cyclic or polycyclic and/or branched moiety advantageously comprises 3 to 6 additional groups 22, in particular 3 to 6 terminal groups 22, wherein the additional groups 22, in particular the terminal groups 22, are preferably identical.

In principle, various chemical groups can be used as additional groups 22 of the aggregating additive 20. Advantageously, the additional groups 22 of the aggregating additive 20 do not interfere or hinder the aggregation of the additive aggregating segment 21 with other additive aggregating segments 21 of other aggregating additives 20 or with polymer aggregating segments 11, 12. The additional groups 22 may be monodisperse or polydisperse. Preferably, the at least one additional group 22 is monodisperse and/or has a molecular weight of less than 500 g/mol, in particular less than 400 g/mol or less than 300 g/mol or less than 200 g/mol or less than 100 g/mol. Monodisperse additional groups 22 particularly allow to achieve higher softening temperatures of the composition.

Good results were obtained when the additional groups 22, in particular the terminal groups 22, of the aggregating additive 20 are miscible with the polymer segment 13. According to an embodiment of the invention, the additional groups 22, in particular the terminal groups 22, are selected from the group consisting of a hydrocarbon group with 1 to 30 carbon atoms, a $C_1$ to $C_{30}$ alkyl group, in particular methyl group, ethyl group, propyl group, butyl group, pentyl group, hexyl group, heptyl group, octyl group, nonyl group, decyl group, undecyl group, dodecyl group, a $C_4$ to $C_{20}$ aromatic moiety, in particular phenyl group, diisopropylphenyl group, di-tert.-butylphenyl group, benzyl group, diisopropylbenzyl group, di-tert.-butylbenzyl group, a branched hydrocarbon group with 1 to 26 carbon atoms, in particular 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group.

Preferably, the additional groups 22, in particular the terminal groups 22, are selected from the group consisting of 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group.

According to an embodiment of the invention, the aggregating additive 20 has a linear structure and comprises two terminal groups 22 that can be any group miscible in the composition, in particular with the polymer segment 13. The two terminal groups 22 can be identical or not. In particular, the two terminal groups 22 can be of any chemical nature as long as both, or one of them, provides solubility in the composition, more particularly in the polymer matrix provided by the polymer segment 13 and optionally a further unfunctionalized polymer. Preferably the two terminal groups 22 are apolar moieties such as $C_1$ to $C_{30}$ hydrocarbon groups, more preferably branched $C_1$ to $C_{30}$ alkyl groups, even more preferably selected from the additional groups 22 listed above. Preferably, the terminal groups 22 are not identical and one of the terminal groups is of as low as possible steric demand. In this way, it can be avoided that this terminal group countervails co-aggregation of the additive aggregating segment 21 of the aggregating additive 20 with the polymer aggregating segments 11, 12. Advantageously, the second terminus is designed such that it provides sufficient solubility in the polymer and for processing purposes, but is preferably not subject to specific intermolecular interactions. Preferably, the first terminal group is a $C_1$ to $C_{12}$ alkyl group, more preferably a methyl group, and the second terminal group is a $C_1$ to $C_{30}$ hydrocarbon fragment, in particular a group selected from the group consisting of a hydrocarbon group with 1 to 30 carbon atoms, a $C_1$ to $C_{30}$ alkyl group, in particular methyl group, ethyl group, propyl group, butyl group, pentyl group, hexyl group, heptyl group, octyl group, nonyl group, decyl group, undecyl group, dodecyl group, a C4 to C20 aromatic moiety, in particular phenyl group, diisopropylphenyl group, di-tert.-butylphenyl group, benzyl group, diisopropylbenzyl group, di-tert.-butylbenzyl group, a branched hydrocarbon group with 1 to 26 carbon atoms, in particular 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group. Preferably, the $C_1$ to $C_{30}$ hydrocarbon fragment is branched in order to reduce the crystallization tendency of the hydrogen bonding units for the sake of improved miscibility with the polymer matrix. According to a preferred embodiment, one of the terminal groups 22 of the aggregating additive 20 is selected from the group consisting of 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group, preferably 2-ethylhexyl, in particular for an aggregating additive 20 that comprises a diglycine or dialanine in the at least one additive aggregating segment 21. In this preferred embodiment, the aggregating additive 20 comprises a methyl group as second terminal group 22 and the additive aggregating segment 21 further comprises an —NH— group and a —C(=O)— group that connect the 2-ethylhexyl group and the methyl group with the dialanine, respectively. However, when the additive aggregating segment 21 of the aggregating additive 20 is a larger oligopeptide such as acetylated triglycine or acetylated trialanine, a larger residue such as 2-octyldodecyl instead of 2-ethylhexyl may be required as terminal group 22 due to the lower solubility of the acetylated trialanine.

According to another embodiment of the invention, the aggregating additive 20 is based on a multifunctional cyclic or polycyclic and/or branched moiety and comprises 3 to 6 terminal groups 22 that can be any group miscible in the composition, in particular with the polymer segment 13. The 3 to 6 terminal groups 22 are preferably identical. In particular, the 3 to 6 terminal groups 22 can be of any chemical nature as long as they provide solubility in the composition, more particularly in the polymer matrix provided by the polymer segment 13 and optionally a further unfunctionalized polymer. Preferably the 3 to 6 terminal groups 22 are apolar moieties such as C1 to C30 hydrocarbon groups, more preferably selected from the group consisting of a hydrocarbon group with 1 to 30 carbon atoms, a $C_1$ to $C_{30}$ alkyl group, in particular methyl group, ethyl group, propyl group, butyl group, pentyl group, hexyl group, heptyl group, octyl group, nonyl group, decyl group, undecyl group, dodecyl group, a $C_4$ to $C_{20}$ aromatic moiety, in particular phenyl group, diisopropylphenyl group, di-tert.-butylphenyl group, benzyl group, diisopropylbenzyl group, di-tert.-butylbenzyl group, a branched hydrocarbon group with 1 to 26 carbon atoms, in particular 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group.

The aggregating additive 20 has a molecular weight of from 50 g/mol to 2000 g/mol. Preferably, the aggregating additive 20 has a molecular weight of from 50 g/mol to 1900 g/mol, in particular from 50 g/mol to 1800 g/mol or from 50 g/mol to 1700 g/mol or from 50 g/mol to 1600 g/mol or from 50 g/mol to 1500 g/mol or from 50 g/mol to 1400 g/mol or from 50 g/mol to 1300 g/mol or from 50 g/mol to 1200 g/mol or from 50 g/mol to 1100 g/mol or from 50 g/mol to 1000 g/mol or from 100 g/mol to 800 g/mol or from 150 g/mol to 700 g/mol or from 150 g/mol to 600 g/mol or from 150 g/mol to 500 g/mol.

The aggregating additive 20 can be monodisperse or polydisperse. Preferably, the aggregating additive 20 is monodisperse. With monodisperse aggregating additives 20, higher softening temperatures of the composition can be achieved.

The composition according to the invention is particularly suited for the preparation of materials or as a material in various applications. For example, materials from the composition according to the invention can be used in the automotive industry. The materials from the composition are used at different temperatures. The temperature at which they are most commonly used may also be called the operating temperature. For example a material that is most commonly used at temperatures of 80° C. is used at an operating temperature of 80° C. According to an embodiment of the invention, the melting temperature of the aggregating additive 20 is at least 30° C., more particularly at least 40° C. or at least 50 OC, higher than the operating temperature at which materials from the composition according to the invention will be used. The melting temperature may also be called melting point. The melting point can be determined by differential scanning calorimetry (DSC) heating scans at a heating rate of 10 K/min. The melting temperature may also be called the dissociation temperature, Td. The melting or dissociation temperature $T_d$ in a composition may in particular be determined by differential scanning calorimetry, in particular at a heating rate of 10 K/min. The higher the melting temperature of the additive is above the operating temperature, the lower is the amount of additive that is required in order to achieve a material with a high softening temperature $T_s$. The softening temperature $T_s$ may in particular be the temperature where the loss factor becomes tan δ≥1. The softening temperature $T_s$ may in particular be determined using oscillatory shear-rheological temperature sweeps, in particular using a parallel plate rheometer with a gap from 0.4 to 0.6 mm at a cooling rate of 3° C./min, a fixed radial frequency of 1 rad/s, and a strain amplitude of 0.1% during the measurement after annealing to 120° C. to 200° C. for 20 min. Preferably, the softening temperature $T_s$ of a material for a thermoplastic elastomer from the composition is higher than the operating temperature at which it will be used.

Structure of the Polymer Aggregating Segments 11, 12 and the Additive Aggregating Segment 21

In particular, the polymer aggregating segments 11, 12 and the at least one additive aggregating segment 21 can be the same or different but preferably, they are both capable of cooperative self-assembly by the same supramolecular interactions. In this way, the polymer aggregating segments 11, 12 and the additive aggregating segment 21 can form aggregates incorporating both the polymer aggregating segments 11, 12 and the additive aggregating segment 21 by co-assembly. Examples of supramolecular interactions include hydrogen bonding interactions, ion-dipole interactions, dipole-dipole interactions, and interactions between a cation and a pi-system. Non-covalent bonds based on supramolecular interactions are preferably formed between chemical functional groups. Examples of such chemical functional groups include carboxylic acid groups, amide groups, urethane groups, urea groups, aromatic groups, perfluoroaromatic groups, hydroxyl groups, amine groups, and a trialkyl ammonium residue. Non-covalent bonds based on the same supramolecular interaction may be formed between different or identical chemical functional groups. For example in the case of hydrogen bonding, a hydrogen bond may be formed between an amide group and a urethane group as an example for a non-covalent bond based on the same supramolecular interaction, wherein the non-covalent bond is formed between different chemical functional groups. A hydrogen bond may also be formed between two amide groups as an example for a non-covalent bond based on the same supramolecular interaction, wherein the non-covalent bond is formed between identical chemical functional groups.

According to an embodiment of the invention, the polymer aggregating segments 11, 12 and the additive aggregating segment 21 each contain at least two interaction sites from which a non-covalent bond is formed.

According to another embodiment of the invention, the non-covalent bonds that can be formed by the polymer aggregating segments 11, 12 and the additive aggregating segment 21 are selected from the group consisting of hydrogen bonds, bonds between ions and dipoles, bonds between dipoles, bonds between a cation and a pi-system, and bonds between pi-systems, in particular selected from the group consisting of hydrogen bonds and bonds between dipoles, more particularly hydrogen bonds. According to another embodiment of the invention, the supramolecular interaction, on which the non-covalent bonds that may be formed by the polymer aggregating segments 11, 12 and the additive aggregating segment 21 are based, is selected from the group consisting of hydrogen bonding interactions, ion-dipole interactions, dipole-dipole interactions, interactions between a cation and a pi-system, and interactions between pi-systems, in particular selected from the group consisting of hydrogen bonding interactions and dipole-dipole interactions, more particularly hydrogen bonding interactions. The aforementioned supramolecular interactions, in particular hydrogen bonding, allow to achieve higher softening temperatures of the composition. For good formation of aggregates 31 in the composition, it is preferable that the supramolecular interactions chosen to affect the co-assembly of the polymer aggregating segments 11, 12 and the additive aggregating segment 21 are neither too weak to not allow for meaningful aggregation, nor too strong to prohibit error correction by reversible, dynamic dissociation and re-association; a suitable range of binding energies for this purpose is 20-100 kJ/mol per interaction site. Thus, according to an embodiment of the invention, each non-covalent bond has a binding energy of from 20 kJ/mol to 100 kJ/mol.

The polymer aggregating segments 11, 12 and the additive aggregating segment 21 are ditopic. The polymer aggregating segments 11, 12 and the additive aggregating segment 21 are preferably ditopic and self-complementary. Preferably, in a ditopic and self-complementary segment, the type and arrangement of the interaction sites in the segment are designed such that, when two segments aggregate via one of the bonding regions of each segment, all the interactions sites of the aggregated bonding regions are saturated, in particular they all have formed non-covalent bonds. More preferably, in a ditopic and self-complementary segment, the type and arrangement of the interaction sites in the segment are designed such that, when two segments aggregate, all interaction sites of one segment, from which non-covalent bonds with an angle from 0° to 45° between these covalent bonds are formed, are saturated. An example for a ditopic and self-complementary segment is a dialanine unit or a benzene tricarboxamide unit. In an aggregate formed from two dialanine units, all interaction sites of one of the bonding regions of each dialanine unit have formed non-covalent bonds and are, thus, saturated. The same applies to an aggregate formed from two benzene tricarboxamide units.

With the aid of ditopic and self-complementary polymer aggregating segments 11, 12 and additive aggregating segment 21, aggregates 31 with a periodic placement of the polymer aggregating segments 11, 12 and/or the additive aggregating segment 21 along at least one extended dimension can be formed from a large number of polymer aggregating segments 11, 12 and/or additive aggregating segment 21 as repeating units. In this way, different from any example of prior art where self-assembling end groups and/or ligands only give rise to dimers, trimers, or oligomers that serve as point-to-point connections between polymer chains in the material even if they rely on multiple self-complementary supramolecular interactions, the successive replacement of polymer aggregating segments 11, 12 with additive aggregating segments 21 in the co-assembled aggregates does not result in a breakage of physical network points that makes up the rubbery network and thus to a weakening of the material.

Thus, according to an embodiment of the invention, the polymer aggregating segments 11, 12 and the additive aggregating segment 21 are complementary and/or identical, in particular complementary and identical, more particularly the polymer aggregating segments 11, 12 and the additive aggregating segment 21 are self-complementary and/or identical, more particularly self-complementary and identical.

Preferably, the supramolecular interactions in the ditopic segments 11, 12, 21, in particular in the ditopic and self-complementary segments 11, 12, 21, that are the origin of the co-assembly of the polymer aggregating segments 11, 12 and the additive aggregating segment 21 should be specific, of limited range, and oriented in space, so that aggregates with a well-defined geometry are formed that are well dispersed in the polymer matrix.

According to an embodiment of the invention, the polymer aggregating segments 11, 12 and the additive aggregating segment 21 each contain donor sites and/or acceptor sites as interaction sites from which non-covalent bonds are formed. Preferably, the self-complementary, ditopic supramolecular interactions of the polymer aggregating segments 11, 12 and the additive aggregating segment 21 should each comprise an electronically conjugated donor and acceptor function, such as a dipole. Advantageously, the polymer aggregating segments 11, 12 and the additive aggregating segment 21 each contain at least one donor site and at least one acceptor site as interaction sites from which non-covalent bonds are formed, in particular wherein the at least one donor site and at least one acceptor site are electronically conjugated. An example of a donor site and an acceptor site that are electronically conjugated, is an amide (—NH—C(=O)—) group. If the polymer aggregating segments 11, 12 and the additive aggregating segment 21 each contain more than one donor and one acceptor site, it is preferred that all the donor and acceptor sites are electronically conjugated in donor-acceptor site pairs. Preferably, a donor site and an acceptor site may be combined in a chemical functional group, for example a chemical functional group that simultaneously provides a hydrogen bond donor and a hydrogen bond acceptor site. Preferably, in each of the ditopic polymer aggregating segments 11, 12 and additive aggregating segment 21, two interaction sites that are not in the same bonding region of the segment are electronically conjugated. Thus, when the ditopic polymer aggregating segments 11, 12 and additive aggregating segment 21 each contain one or more pairwise electronically conjugated donor and acceptor sites, preferably, the donor site and the acceptor site in each electronically conjugated donor and acceptor site pair are distributed over the two bonding regions of the respective ditopic segment. In this way, the co-assembly of the polymer aggregating segments 11, 12 and the additive aggregating segment 21 into aggregates becomes cooperative, which serves to increase their dissociation temperature and decrease the dissociation temperature range. Examples of a ditopic segment that contains pairwise electronically conjugated donor and acceptor sites, wherein the donor and acceptor site in each donor and acceptor site pair are distributed over the two bonding regions of the ditopic segment are segments comprising amide groups or urethane groups or urea groups, in particular oligopeptides, oligoamides, oligourethanes, oligoureas, and multifunctional cyclic or polycyclic and/or branched moieties, wherein the multifunctional cyclic or polycyclic and/or branched moiety comprises at least three amide or urethane or urea groups.

More preferably, in each of the ditopic polymer aggregating segments 11, 12 and additive aggregating segment 21, two adjacent interaction sites, wherein the angle between these adjacent interaction sites is from 90° to 180°, preferably from 170° to 180°, are electronically conjugated. Thus, when the ditopic polymer aggregating segments 11, 12 and additive aggregating segment 21 each contain one or more adjacent and pairwise electronically conjugated donor and acceptor sites, preferably, there is an angle of from 90° to 1800, in particular from 170° to 1800, between the non-covalent bonds formed from the donor site and from the acceptor site of each electronically conjugated donor and acceptor site pair in the respective ditopic segment. Examples of a ditopic segment that contains adjacent and pairwise electronically conjugated donor and acceptor sites, wherein there is an angle of from 90° to 1800, in particular from 170° to 180°, between the non-covalent bonds formed from the donor site and from the acceptor site of each electronically conjugated donor and acceptor site pair in the ditopic segment are segments comprising amide groups or urethane groups or urea groups, in particular oligopeptides, oligoamides, oligourethanes, oligoureas, and multifunctional cyclic or polycyclic and/or branched moieties, wherein the multifunctional cyclic or polycyclic and/or branched moiety comprises at least three amide or urethane or urea groups.

It is therefore preferable for the polymer aggregating segments 11, 12 and the at least one additive aggregating segment 21 to provide one or more such chemical functional groups. According to an embodiment of the invention, the polymer aggregating segments 11, 12 and the additive aggregating segment 21 each contain at least one, in particular 2 to 10 or 2 to 5, chemical functional groups that, in particular provide a donor site and an acceptor site as interaction sites from which non-covalent bonds are formed, in particular wherein the donor site and the acceptor site are electronically conjugated. In this way, their co-assembly can be adjusted more easily to result in aggregation but still allow for error correction by dynamic dissociation and re-association. Preferably, the polymer aggregating segments 11, 12 and the additive aggregating segment 21 each contain 2 to 10 or 2 to 5 chemical functional groups that provide self-complementary, ditopic, electronically conjugated donor and acceptor sites.

Various chemical functional groups can be used that provide an electronically conjugated donor and acceptor site. Advantageous are chemical functional groups that each simultaneously provide an electronically conjugated hydrogen bond donor and a hydrogen bond acceptor site, particularly in the form of —C(=Y)—NH functions that can be part of a —C(=Y)—NH— function, a —O—C(=Y)—NH— function, or a —NH—C(=Y)—NH— function, wherein in each case, Y is selected from the group consisting of NH, S, and O, preferably O. Thus, according to an embodiment of the invention, the donor and acceptor site of the chemical functional group of the polymer aggregating segments 11, 12 and the additive aggregating segment 21 are capable of forming hydrogen bonds, in particular wherein the chemical functional group is selected from the group consisting of peptide (—C(=O)—NH—), amide (—C(=O)—NH—), urethane (—O—C(=O)—NH—), urea (—NH—C(=O)—NH—), thiopeptide (—C(=S)—NH—), thioamide (—C(=S)—NH—), thiourethane (—O—C(=S)—NH—), thiourea (—NH—C(=S)—NH—), —C(=NH)—NH—, —O—C(=NH)—NH—, and —NH—C(=NH)—NH—, more preferably selected from the group consisting of peptide (—C(=O)—NH—), amide (—C(=O)—NH—), urethane (—O—C(=O)—NH—), and urea (—NH—C(=O)—NH—), most preferably selected from the groups consisting of peptide (—C(=O)—NH—) and amide (—C(=O)—NH—). A segment that contains at least one of the aforementioned chemical functional groups is a ditopic segment that contains at least two interactions sites from which non-covalent bonds, in particular hydrogen bonds, can be formed.

Thus, according to an embodiment, the invention provides for a composition containing
   a. a functionalized polymer 10 that comprises at least one polymer segment 13 and at least two polymer aggregating segments 11, 12 each comprising at least one chemical functional group selected from the group consisting peptide (—C(=O)—NH—), amide (—C(=O)—NH—), urethane (—O—C(=O)—NH—), urea (—NH—C(=O)—NH—), thiopeptide (—C(=S)—NH—), thioamide (—C(=S)—NH—), thiourethane (—O—C(=S)—NH—), thiourea (—NH—C(=S)—NH—), —C(=NH)—NH—, —O—C(=NH)—NH—, and —NH—C(=NH)—NH—, more preferably selected from the group consisting of peptide (—C(=O)—NH—), amide (—C(=O)—NH—), urethane (—O—C(=O)—NH—), and urea (—NH—C(=O)—NH—), most preferably selected from the groups consisting of peptide (—C(=O)—NH—) and amide (—C(=O)—NH—);
   b. an aggregating additive 20 that comprises at least one additive aggregating segment 21 comprising at least one chemical functional group selected from the group consisting of peptide (—C(=O)—NH—), amide (—C(=O)—NH—), urethane (—O—C(=O)—NH—), urea (—NH—C(=O)—NH—), thiopeptide (—C(=S)—NH—), thioamide (—C(=S)—NH—), thiourethane (—O—C(=S)—NH—), thiourea (—NH—C(=S)—NH—), —C(=NH)—NH—, —O—C(=NH)—NH—, and —NH—C(=NH)—NH—, more preferably selected from the group consisting of peptide (—C(=O)—NH—), amide (—C(=O)—NH—), urethane (—O—C(=O)—NH—), and urea (—NH—C(=O)—NH—), most preferably selected from the groups consisting of peptide (—C(=O)—NH—) and amide (—C(=O)—NH—).
   wherein the polymer aggregating segments 11, 12 and the additive aggregating segment 21 are designed such that they can form aggregates 31 that contain polymer aggregating segments 11, 12 and additive aggregating segments 21, and wherein the aggregating additive 20 has a molecular weight of from 50 g/mol to 2000 g/mol, in particular from 50 g/mol to 1300 g/mol, more particularly from 50 g/mol to 1000 g/mol. According to this embodiment, the aggregating additive 20 is preferably monodisperse.

If the polymer aggregating segments 11, 12 and the additive aggregating segment 21 each contain more than one chemical functional group, these chemical functional groups may be different from each other or identical. It is particularly preferable that these chemical functional groups are placed at defined distances along the polymer aggregating segments 11, 12 and the additive aggregating segment 21, so that the polymer aggregating segments 11, 12 and the additive aggregating segment 21 can co-assemble in-register in spite of the specific, short range, and geometrically defined nature of the supramolecular interactions.

According to another embodiment of the invention, the polymer aggregating segments 11, 12 and the additive aggregating segment 21 each comprise an oligopeptide and/or an oligoamide and/or an oligourethane and/or an oligourea and/or a multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—, in particular from the group consisting of —C(=O)—NH—, —NH—C(=O)—, —O—C(=O)—NH—, —NH—C(=O)—O—, and —NH—C(=O)—NH—, more particularly from the group consisting of —C(=O)—NH— and —NH—C(=O)—. Preferably, the polymer aggregating segments 11, 12 and the additive aggregating segment 21 each comprise an oligopeptide and/or an oligoamide.

A segment that comprises at least an oligopeptide and/or an oligoamide and/or an oligourethane and/or an oligourea and/or a multifunctional cyclic or polycyclic and/or branched moiety as described above is a ditopic segment that contains at least two interactions sites from which non-covalent bonds, in particular hydrogen bonds, can be formed.

Thus, according to an embodiment, the invention provides for a composition containing
  a. a functionalized polymer 10 that comprises at least one polymer segment 13 and at least two polymer aggregating segments 11, 12 each comprising an oligopeptide and/or an oligoamide and/or an oligourethane and/or an oligourea and/or a multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—,
  b. an aggregating additive 20 that comprises at least one additive aggregating segment 21 comprising an oligopeptide and/or an oligoamide and/or an oligourethane and/or an oligourea and/or a multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—,
  wherein the polymer aggregating segments 11, 12 and the additive aggregating segment 21 are designed such that they can form aggregates 31 that contain polymer aggregating segments 11, 12 and additive aggregating segments 21, and wherein the aggregating additive 20 has a molecular weight of from 50 g/mol to 2000 g/mol, in particular from 50 g/mol to 1300 g/mol, more particularly from 50 g/mol to 1000 g/mol. According to this embodiment, the aggregating additive 20 is preferably monodisperse.

Preferably, the oligopeptide contains from 1 to 10, in particular from 2 to 5, peptide units, the oligoamide contains from 1 to 10, in particular from 2 to 5, amide units, the oligourethane contains from 1 to 10, in particular from 2 to 5, urethane units, the oligourea contains from 1 to 10, in particular from 2 to 5, urea units and/or the multifunctional cyclic or polycyclic and/or branched moiety contains from 2 to 6, in particular 3 chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—O—, —NH—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—, in particular from the group consisting of —C(=O)—NH—, —NH—C(=O)—, —O—C(=O)—NH—, —NH—C(=O)—O—, and —NH—C(=O)—NH—, more particularly from the group consisting of —C(=O)—NH— and —NH—C(=O)—.

In the above embodiments, the at least two, in particular at least three, chemical functional groups of the multifunctional cyclic or polycyclic and/or branched moiety are preferably identical and selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—, in particular from the group consisting of —C(=O)—NH—, —NH—C(=O)—, —O—C(=O)—NH—, —NH—C(=O)—O—, and —NH—C(=O)—NH—, more particularly from the group consisting of —C(=O)—NH— and —NH—C(=O)—.

The units of the oligopeptide, the oligoamide, the oligourethane and the oligourea may be made up from building blocks selected from the group consisting of natural amino acids, synthetic amino acids, diacids, diamines, isocyanates, alcohols, amines, and mixtures thereof. The natural amino acids are known to the skilled person. Synthetic amino acids preferably have the structure HOOC—$R^1$—$NH_2$, wherein $R^1$ is a hydrocarbon group with 2 to 15 carbon atoms, in particular they are selected from the group consisting of beta-alanine, 3-aminopropanoic acid, 4-aminobutanoic acid, 5-aminopentanoic acid, 6-aminohexanoic acid, p-aminobenzoic acid, or m-aminobenzoic acid. Diacids preferably have the structure HOOC—$R^2$—COOH, wherein $R^2$ is a hydrocarbon group with 1 to 15 carbon atoms, in particular they are selected from the group consisting of malonic acid, succinic acid, glutaric acid, adipic acid, pimelic acid, suberic acid, azelaic acid, sebacoic acid, undecandedioic acid, dodecanedioic acid, tridecanedioic acid, tetradecanedioic acid, p-terephthalic acid, m-terephthalic acid, napthalene-2,6-dicarboxylic acid, napthalene-1,5-dicarboxylic acid, and 1,1'-biphenyl-4,4'-dicarboxylic acid. Diamines preferably have the structure $H_2N$—$R^3$—$NH_2$, wherein $R^3$ is a hydrocarbon group with 1 to 15 carbon atoms, in particular they are selected from the group consisting of tetramethylene diamine, pentamethylene diamine, hexamethylene diamine, heptamethylene diamine, octamethylene diamine, nonamethylene diamine, decamethylene diamine, p-phenylene diamine, m-phenylene diamine, 1,3-bis(aminomethyl)benzene, 1,4-bis(aminomethyl)benzene, 1,3-bis(aminomethyl)cyclohexane, 1,4-bis(aminomethyl)cyclohexane, and 4,4'-diamino-1,1'-biphenyl. Diisocyanates preferably have the structure OCN—$R^4$—NCO, wherein $R^4$ is a hydrocarbon group with 1 to 15 carbon atoms, in particular they are selected from the group consisting of hexamethylene diisocyanate, toluene diisocyanate, and diphenylmethylene diisocyanate. Diols preferably have the structure HO—$R^5$—OH, wherein $R^5$ is a hydrocarbon group with 2 to 15 carbon atoms, in particular they are selected from the group consisting of ethanediol, propane-1,2-diol, propane-1,3-diol, butane-1,4-diol, pentane-1,5-diol, 1,4-dihydroxybenzene, 4,4'-dihydroxy-1,1'-biphenyl, and bisphenol A.

It is apparent for one skilled in the art which of the aforementioned repeating units are applicable to the oligopeptide, the oligoamide, the oligourethane, and the oligourea. In particular, it is apparent for one skilled in the art that oligopeptides can be obtained by combining amino acids, oligoamides can be obtained by combining amino acids and/or diacids and/or diamines, oligourethanes can be obtained by combining diisocyanates with diols and oligoureas can be obtained by combining diisocyanates with diamines. Of course, other combinations are conceivable, such as diamines with diacids and diisocyanates to provide a mixed oligoamide-oligourea.

The multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—, can be made up from the respective polycarboxylic acid or polyamine derivatives or polyol or polythiol derivatives or derivatives with different functional groups as building blocks. In particular, the multifunctional cyclic or polycyclic and/or branched moiety may be based on amides derived from polycarboxylic acids or on amides and ureas derived from polyamines or on urethanes derived from polyols.

Polycarboxylic acids preferably have the structure $R^6$—$(COOH)_a$, wherein $R^6$ is a hydrocarbon group with 2 to 20 carbon atoms and a is an integer from 3 to 6, in particular they are selected from the group consisting of benzene-1,3,5-tricarboxylic acid, benzene-1,2,4-tricarboxylic acid, benzene-1,2,4,5-tetracarboxylic acid, benzene-1,2,3,4,5-pentacarboxylic acid, benzene-1,2,3,4,5,6-hexacarboxylic acid, 1,1'-biphenyl-3,4',5-tricarboxylic acid, 1,1'-biphenyl-3,3',5,5'-tetracarboxylic acid, [1,1':4',1"]terphenyl-3,3",5,5"-tetracarboxylic acid, 1,3,5-tris(4-carboxyphenyl)benzene, 1,2,4,5-tetrakis (4-carboxyphenyl)benzene, 3,3',5,5'-tetracarboxydiphenylmethane, 1,3,5-s-triazine-2,4,6-tricarboxylic acid, 2,4,6-tris(4-carboxyphenyl)-1,3,5-triazine, cyclohexane-1,3,5-tricarboxylic acid, cyclohexane-1,2,4-tricarboxylic, cyclohexane-1,2,4,5-tetracarboxylic acid, cyclohexane-1,2,3,4,5,6-hexacarboxylic acid, 1,2,3,4-cyclopentanetetracarboxylic acid, 1,2,3,4-cyclobutanetetracarboxylic acid, 1,1,2-ethanetricarboxylic acid, 1,2,3-propanetricarboxylic acid, 2-hydroxy-1,2,3-propanetricarboxylic acid (citric acid), 1,2,4-butanetricarboxylic acid, 1,2,3,4-butanetetracarboxylic acid, and 1,3,5-pentanetricarboxylic acid.

Polyamines preferably have the structure $R^7$—$(NH_2)_b$, wherein $R^7$ is a hydrocarbon group with 2 to 20 carbon atoms and b is an integer from 3 to 6, in particular they are selected from the group consisting of 1,3,5-triaminobenzene, 1,2,4-triaminobenzene, 2,4,6-triaminotoluene, 1,2,4,5-tetraaminobenzene, 1,3,5-tris (aminomethyl)benzene, 1,2,4,5-tetrakis(aminomethyl)benzene, 1,3,5-triaminocyclohexane, 3,3',4,4'-tetraamino-1,1'-biphenyl, N,N,N-tris(2-aminoethyl)amine, N,N,N-tris(3-aminopropyl)amine, and N,N,N',N'-tetrakis(3-aminopropyl)-1,4-butanediamine.

Polyols preferably have the structure $R^8$—$(OH)_c$, wherein $R^8$ is a hydrocarbon group with 2 to 20 carbon atoms and c is an integer from 3 to 6, in particular they are selected from the group consisting of 1,3,5-trihydroxybenzene and its derivatives, in particular 2,4,6-trihydroxybenzoic acid, 1,2,4-trihydroxybenzene and its derivatives, in particular 2,4,5-trihydroxybenzoic acid, 1,2,3-trihydroxybenzene and its derivatives, in particular 3,4,5-trihydroxybenzoic acid and 2,3,4-trihydroxybenzoic acid, 2,4,6-trihydroxytoluene, 3,4,5-trihydroxytoluene, 2,3,5,6-tetrahydroxy-1,4-quinone, 1,3,5-trihydroxycyclohexane, 1,2,3,4,5,6-hexahydroxycyclohexane, 1,1,1-tris(hydroxymethyl)methane, 1,1,1-tris(hydroxymethyl)ethane, 1,1,1-tris(hydroxymethyl)propane, and pentaerythritol.

It is apparent to the person skilled in the art how to prepare amides, urethanes, or ureas from the aforementioned building blocks. In particular, it is apparent for one skilled in the art that amides can be prepared by combining the above polycarboxylic acids with amines or by combining the above polyamines with carboxylic acid derivatives, urethanes can be prepared by combining the above polyols with isocyanates, and ureas can be prepared by combining the above polyamines with isocyanates. Moieties with mixed functionalities can of course be prepared by combining a molecule with different functionalities with the respective amines, carboxylic acid derivatives or isocyanates, for example by combining citric acid with an amine and with an isocyanate.

According to an embodiment of the invention, the polymer aggregating segments 11, 12 and the additive aggregating segment 21 each comprise an oligopeptide and/or an oligoamide and/or an oligourethane and/or an oligourea and/or a multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—, in particular from the group consisting of —C(=O)—NH—, —NH—C(=O)—, —O—C(=O)—NH—, —NH—C(=O)—O—, and —NH—C(=O)—NH—, more particularly from the group consisting of —C(=O)—NH— and —NH—C(=O)—, wherein the oligopeptide, the oligoamide, the oligourethane, the oligourea, or the multifunctional cyclic or polycyclic and/or branched moiety are made up from the respective building blocks as described above.

According to another embodiment of the invention, the polymer aggregating segments 11, 12 and the additive aggregating segment 21 each comprise an oligopeptide and/or an oligoamide and/or an oligourea and/or a multifunctional cyclic or polycyclic and/or branched moiety comprising at least two, in particular at least three, chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C (=O)—NH—, —S—C(=S)—NH—, and —S—C(=NH)—NH—, in particular from the group consisting of —C(=O)—NH—, —NH—C(=O)—, —O—C(=O)—NH—, —NH—C(=O)—O—, and —NH—C(=O)—NH—, more particularly from the group consisting of —C(=O)—NH— and —NH—C(=O)—, wherein the oligopeptide, the oligoamide, the oligourea, or the multifunctional cyclic or polycyclic and/or branched moiety are made up from the respective building blocks as described above.

According to another embodiment of the invention, the polymer aggregating segments 11, 12 and the additive aggregating segment 21 each comprise a moiety with the structure (—C(=O)—$R^9$—NH—)$_d$ or with the structure (—C(=O)—$R^{10}$—C(=O)NH—$R^{11}$—NH—)$_e$ or with the structure (—C(=O)—NH—$R^{12}$—NH—C(=O)—O—$R^{13}$—O—)$_f$ or with the structure (—C(=O)—NH—$R^{14}$—NH—C(=O)—NH—$R^{15}$—NH—)$_g$, or with the structure D(—Z—)$_o$, wherein d is an integer from 1 to 10, in particular from 2 to 5, and $R^9$ is —$C_6H_4$— or (—$CR^{16}H$—)$_h$, wherein h is an integer from 1 to 6, in particular 1 or 2, and each $R^{16}$ is independently H or Me, e is an integer from 1 to 10, in particular from 2 to 5, and $R^{10}$ is —$C_6H_4$— or (—$CH_2$—)$_i$, wherein i is an integer from 1 to 6, and $R^{11}$ is —$C_6H_4$— or —$CH_2C_6H_4CH_2$— or (—$CH_2$—)$_j$, wherein j is an integer from 1 to 6, f is an integer from 1 to 10, in particular from 2 to 5, and $R^{12}$ is —$C_6(Me)H_3$— or (—$CH_2$-)$_k$, wherein k is an integer from 1 to 6, and $R^{13}$ is —$C_6H_4$— or (—$CH_2$—)$_l$, wherein l is an integer from 1 to 6, g is an integer from 1 to 10, in particular from 2 to 5, and $R^{14}$ is —$C_6(Me)H_3$— or (—$CH_2$-)$_z$, wherein z is an integer from 1 to 6, and $R^{15}$ is —$C_6H_4$— or —$CH_2C_6H_4CH_2$— or (—$CH_2$—)$_y$, wherein y is an integer from 1 to 6, is an integer from 3 to 6, in particular 3, D is a benzene or a cyclohexane or a 1,3,5-triazine moiety and each Z is independently selected from the group consisting of —C(=O)—NH—, —C(=NH)—NH—, —NH—C(=O)—, —NH—C(=NH)—, —NH—C(=O)—O—, —NH—C(=NH)—O—, —NH—C(=O)—NH—, —NH—C(=NH)—NH—, and —O—C(=O)—NH—, more preferably from the group consisting of —C(=O)—NH—, —NH—C(=O)—, —O—C(=O)—NH—, —NH—C(=O)—O—, and —NH—C(=O)—NH—, even more preferably from the group consisting of —C(=O)—NH— and —NH—C(=O)—. In this embodiment, all —Z— are preferably identical.

In addition to interaction sites that stem from the building blocks of monovalent, divalent, or multivalent oligomers or the multifunctional cyclic or polycyclic and/or branched moiety, the polymer aggregating segments 11, 12 and the additive aggregating segment 21 may each also contain chemical functional groups that may provide an additional interaction site. Preferably the additional chemical functional groups are independently selected from the group consisting of —O—, —NH—, —S—, —C(=O)—, —C(=S)—, and —C(=NH)—, more preferably from the group consisting of —NH— and —C(=O)—. Preferably, the polymer aggregating segments 11, 12 and the additive aggregating segment 21 contain 1 or 2 additional chemical functional groups.

According to an embodiment of the invention, the polymer aggregating segments 11, 12 and the least one additive aggregating segment 21 are linear. According to this embodiment, the polymer aggregating segments 11, 12 are polydisperse or monodisperse, in particular monodisperse, and/or the at least one additive aggregating segment 21 is polydisperse or monodisperse, in particular monodisperse. For example, the polymer aggregating segments 11, 12 and the at least one additive aggregating segment 21 can be based on monodisperse oligomers with a precise number n of repeating units and a defined molar mass, or they can be short polydisperse segments, that is, a mixture of oligomers with different numbers n of repeating units and a molar mass distribution with a number-average degree of polymerization ñ=1-10. Preferably, the polymer aggregating segments 11, 12 and the additive aggregating segment 21 are based on monodisperse oligomers, because their aggregation, in particular their cooperative, in-register self-assembly then results in geometrically defined aggregates with higher dissociation temperatures and sharper dissociation transitions with reduced hysteresis at the same or even smaller length of the polymer aggregating segments 11, 12 and the additive aggregating segment 21 and/or the same or even smaller total concentration of the polymer aggregating segments 11, 12 and additive aggregating segment 21 in the material, because polydisperse mixtures would be subject to a melting point depression and inhomogeneity mostly originating in the increased contribution of the interfacial energy between the aggregates and the polymer matrix that is disfavorable for aggregation. For example, the polymer aggregating segments 11, 12 and the additive aggregating segment 21 may comprise or consist of a monovalent, divalent, or multivalent oligomer, in particular a monodisperse oligomer. A divalent oligomer may in particular have the structure —$U_n$— that can be an oligopeptide, oligoamide, oliogurethane, or oligourea, where the building blocks for the n repeating units U can be chosen from any natural or synthetic amino acids, diacids, diamines, diols, and/or diisocyanates. Different types of repeating units U can also be combined. The preferred number of repeating units U is n=1-10. The segments should not contain more than 10 units because deaggregation would occur at too high temperatures, aggregation would occur on too slow time scales, error correction by reversible, dynamic dissociation and re-association would be kinetically hindered.

The polymer aggregating segments 11, 12 and the additive aggregating segments 21 can be chosen to be different or identical. If the polymer aggregating segments 11, 12 and the least one additive aggregating segment 21 are linear and different, then they should preferably have the same number n or number-average number nf of repeating units, which will ensure better cooperative, in-register co-assembly and thus comparably higher dissociation temperatures and sharper dissociation transitions with reduced hysteresis. Even more preferred are combinations of the polymer aggregating segments 11, 12 and the additive aggregating segment 21 with the same number n or number-average number it of repeating units that place the chemical functional groups responsible for co-assembly at the same distances, which will again ensure better cooperative, in-register co-assembly and thus comparably higher dissociation temperatures and sharper dissociation transitions with reduced hysteresis. Even more preferably, the polymer aggregating segments 11, 12 and the additive aggregating segment 21 are chosen to be identical, which will even further ensure better cooperative, in-register co-assembly and thus comparably higher dissociation temperatures and sharper dissociation transitions with reduced hysteresis, because mixtures in which the polymer aggregating segments 11, 12 are different from the additive aggregating segment 21 would be subject to a melting point depression of the resulting aggregates.

Thus, preferably the polymer aggregating segments 11, 12 and the additive aggregating segment 21 comprise an oligopeptide, an oligoamide, an oligourethane, and/or an oligourea that are as defined above. More preferably, the polymer aggregating segments 11, 12 and the additive aggregating segment 21 comprise an oligopeptide, an oligoamide, and/or an oligourea that are as defined above.

According to another embodiment of the invention, the polymer aggregating segments 11, 12 and the additive aggregating segment 21 each comprise a group with the structure $D(-Z-)_x$, wherein D is a multifunctional cyclic or polycyclic and/or branched moiety, Z is selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, —S—C(=NH)—NH—, preferably from the group consisting of —C(=O)—NH—, —NH—C(=O)—, —O—C(=O)—NH—, —NH—C(=O)—O—, and —NH—C(=O)—NH—, more preferably from the group consisting of —C(=O)—NH— and —NH—C(=O)—, and x is an integer from 2 to 6. Preferably, the multifunctional cyclic or polycyclic and/or branched moiety is as defined above. According to a preferred embodiment, the polymer aggregating segments 11, 12 and the additive aggregating segment 21 each comprise a group with the structure $D(-C(=O)-NH-)_3$ or $D(-NH-C(=O)-)_3$, wherein D is a benzene or a cyclohexane or a 1,3,5-triazine core.

The polymer aggregating segments 11, 12 and the additive aggregating segment 21 can be chosen to be chiral or achiral. If the polymer aggregating segments 11, 12 and the additive aggregating segment 21 are linear, they are preferably chiral. It is believed that the co-assembly of linear chiral segments into extended nanostructures is associated with the emergence of supramolecular helicity, which suppresses lateral interactions and thus supports the formation of nanostructures with only one extended dimension. If the chiral or achiral polymer aggregating segments 11, 12 and the additive aggregating segment 21 are based on a cyclic or polycyclic and/or branched core, this core should be chosen so as to favor the formation of nanostructures with only one extended dimension. In either case, this formation of nanostructures with only one extended dimension. is deemed favorable because it favors dispersion of the aggregates 31 formed from the polymer aggregating segments 11, 12 and the additive aggregating segment 21 in the polymer matrix and disfavors the possibility for the aggregating additive 20 to crystallize in the matrix based on the self-assembly of its at least one additive aggregating segment 21 without an interaction with the polymer aggregating segments 11, 12, which would result in phase segregation and inferior macroscopic properties.

The Composition

The polymer aggregating segments 11, 12 and the additive aggregating segment 21 are designed such that they can form aggregates 31 that contain polymer aggregating segments 11, 12 and additive aggregating segments 21. According to an embodiment of the invention, aggregates 31 that contain polymer aggregating segments 11, 12 and additive aggregating segments 21 are formed in the composition. The aggregates 31 may in particular be formed in the composition during preparation of the composition. More particularly, the aggregates 31 may be formed during mixing of the functionalized polymer 10 and the aggregating additive 20 and optional further components in solution or in the melt. Thus, according to an embodiment of the invention, the composition contains aggregates 31 that contain polymer aggregating segments 11, 12 and additive aggregating segments 21. Preferably, the aggregates 31 extend in one or in two dimensions, in particular in one dimension. An aggregate 31 that extends in one or in two dimensions may in particular have a large number, more particularly at least 30 or at least 50, of repeating units in this dimension or in these dimensions. On the other hand, an aggregate 31 that extends in one or in two dimensions may in particular have in the dimensions or in the dimension, in which it does not extend a small number, more particularly less than 5, of repeating units, in particular 2 or 1 repeating units. The repeating units in this case may in particular be the polymer aggregating segments 11, 12 and the additive aggregating segment 21. If the polymer aggregating segments 11, 12 and the additive aggregating segment 21 are linear, the structure may be a tape or a ladder either of which may be twisted, in which the polymer aggregating segments 11, 12 and the additive aggregating segments 21 form the rungs of the ladder. Two or more such tapes or ladders may further aggregate with their faces to form a fibrillar aggregate. According to an embodiment, the aggregates 31 are tape-like structures. According to another embodiment, the aggregates 31 are fibrillar aggregates. The tape-like or fibrillar aggregates 31 may be extended in one dimension, in particular they may have one characteristic length on the length scale above 50 nm, more particularly above 100 nm. In the other two dimensions, the size of the tape-like or fibrillar aggregates 31 may be limited by the small number of repeating units, in particular less than 5 repeating units, more particularly 1 or 2 repeating units. Accordingly, the tape-like or fibrillar aggregates 31 may have a diameter of below 20 nm, in particular below 10 nm in the other two dimensions. In another embodiment, the polymer aggregating segments 11, 12 and the additive aggregating segment 21 give rise to a lamellar structure that extends in two dimensions. According to this embodiment, the aggregates 31 are lamellar structures. The lamellar structures may in particular have two characteristic lengths on the length scale above 50 nm, in particular above 100 nm. In the other dimension, the size of the lamellar aggregates 31 may be limited by the small number of repeating units, in particular less than 5 repeating units, more particularly 1 or 2 repeating units. Accordingly, the lamellar aggregates 31 may have a thickness below 20 nm, in particular below 10 nm. Both for the tape-like or fibrillary aggregates 31 and for the lamellar aggregates 31, the repeating units may in particular be the polymer aggregating segments 11, 12 and the additive aggregating segment 21. Preferably, at least 50 wt %, more preferably at least 60 wt % or at least 70 wt % or at least 80 wt % or at least 90 wt % of the aggregating additive 20, in each case based on the total weight of the aggregating additive 20 in the composition, is present in the composition as part of aggregates 31 that also contain polymer aggregating segments 11, 12.

The composition according to the invention contains the functionalized polymer 10 and the aggregating additive 20. The composition may consist of the functionalized polymer 10 and the aggregating additive 20. The composition may contain only one type of aggregating additive 20 or several different types of aggregating additives 20 that are as described herein. In addition, the composition may contain a further polymer and/or other additives. If the composition contains a further polymer, it is preferably unfunctionalized. Thus, according to an embodiment of the invention, the composition contains a further polymer selected from the group consisting of polyolefins, in particular poly(isoprene) (PI), hydrogenated poly(isoprene) (HPI), poly(butadiene) (PB), hydrogenated poly(butadiene) (HPB), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP); polysiloxanes, in particular poly(dimethylsiloxane) (PDMS); polyesters, in particular poly(glycolide) (PGA), amorphous or semicrystalline poly(lactide) (PLA), poly(3-hydroxybutyrate) (P3HB), poly(ethylene adipate), poly(ethylene succinate); polyethers, in particular poly(ethylene oxide) (PEO), poly(propylene oxide) (PPO), poly(tetrahydrofuran) (PTHF); and polyacrylates and polymethacrylates, in particular poly(butyl acrylate) (PBuA), poly(methyl methacrylate) (PMMA), and poly(ethylene-co-acrylate)s and/or the composition contains a further additive selected from the group consisting of inorganic fillers, organic fillers, pigments, dyes, flame retardants, and mixtures thereof. If the composition contains a further polymer, this polymer is preferably of the same type as the polymer segment 13 of the functionalized polymer 10. For example, if the polymer segment 13 of the functionalized polymer 10 is poly(isobutylene), the further polymer is preferably poly(isobutylene). For the molecular weight of the further polymer, the provisions concerning the polymer segment 13 shall apply.

The composition may contain the aggregating additive 20 in different amounts. Preferably, the composition contains the aggregating additive in an amount from 0.1 to 20 wt %, more preferably from 0.1 to 10 wt %, even more preferably from 0.1 to 5 wt %, in each case based on the total weight of the composition.

An important parameter for the composition according to the invention is the total concentration of the polymer aggregating segments 11, 12 and the additive aggregating segment 21 in the composition. The total concentration of the polymer aggregating segments 11, 12 and the additive aggregating segment 21 is calculated as Total concentration of the polymer aggregating segments 11, 12 and the additive aggregating segment 21=(Weight of the polymer aggregating segments 11, 12 in the composition+weight of the additive aggregating segment 21 in the composition)/(total weight of the composition).

Preferably, the total concentration of the polymer aggregating segments 11, 12 and the additive aggregating segment 21 in the composition ranges from 0.1 wt % to 20 wt %, preferably from 1 wt % to 20 wt % or from 1 wt % to 15 wt % of from 1 wt % to 10 wt % or from 1 wt % to 5 wt %.

Preferred Embodiments

Thus, according to a preferred embodiment of the invention, the aggregating additive 20 has the structure R'—X'—R" where X' is the additive aggregating segment 21 capable of forming non-covalent bonds, and R' and R" are terminal groups 22 that preferably serve to provide solubility of the aggregating additive 20 in the composition, more preferably, R' and R" are selected from the additional groups 22 listed above.

According to another preferred embodiment of the invention, the aggregating additive 20 has the structure $R^{20}$-$A^1$-$U^1$—C(=O)—$R^{21}$, wherein
  $R^{20}$ is a branched alkyl group selected from the group consisting of 2-ethylhexyl group, 2-butyloctyl group, 2-hexyldecyl group, 2-octyldodecyl group, 2-decyltetradecyl, 2-hexyloctanyl, 2-octyldecyl, 1-methylethyl, 1-ethylpropyl, 1-propylbutyl, 1-butylpentyl, 1-pentylhexyl, 1-hexylheptyl, 1-heptyloctyl, 1-octylnonyl, 1-nonyldocyl, 1-docylundecyl, 1-undecyldodecyl, and 1-dodecyltridecyl, preferably a 2-ethylhexyl group or a 2-octyldodecyl group,
  $A^1$ is a covalent bond, —C(=O)—, —O— or —NH—, preferably —NH—,
  $U^1$ is an oligopeptide containing 1 to 5 natural and/or synthetic amino acids, in particular alanine, glycine, beta-alanine, 3-aminopropanoic acid, 4-aminobutanoic acid, 5-aminopentanoic acid, 6-aminohexanoic acid, p-aminobenzoic acid, or m-aminobenzoic acid, preferably containing 2 to 5 alanine, and
  $R^{21}$ is selected from the group consisting of methyl group, ethyl group, propyl group, butyl group, pentyl group, and hexyl group, preferably a methyl group.

According to another preferred embodiment of the invention, the aggregating additive 20 has the structure $R^{20}$-$A^1$-$U^2$—$B^1$—$R^{21}$, wherein
  $R^{20}$, $A^1$ and $R^{21}$ are as defined above,
  $B^1$ is selected from the group consisting of a covalent bond, —C(=O)—, —NH—, and —O—, and
  $U^2$ is an oligoamide containing 1 to 5 repeating units made up from diacids and diamines, preferably made up from malonic acid, succinic acid, glutaric acid, adipic acid, pimelic acid, suberic acid, azelaic acid, sebacoic acid, undecandedioic acid, dodecanedioic acid, tridecanedioic acid, tetradecanedioic acid, p-terephthalic acid, m-terephthalic acid, napthalene-2,6-dicarboxylic acid, napthalene-1,5-dicarboxylic acid, 1,1'-biphenyl-4,4'-dicarboxylic acid, tetramethylene diamine, pentamethylene diamine, hexamethylene diamine, heptamethylene diamine, octamethylene diamine, nonamethylene diamine, decamethylene diamine, p-phenylene diamine, m-phenylene diamine, 1,3-bis(aminomethyl)benzene, 1,4-bis(aminomethyl)benzene, 1,3-bis(aminomethyl)cyclohexane, 1,4-bis(aminomethyl)cyclohexane, and 4,4'-diamino-1,1'-biphenyl.

According to another preferred embodiment of the invention, the aggregating additive 20 has the structure $R^{20}$-$A^2$-$U^3$—$B^2$—$R^{21}$, wherein
  $R^{20}$, $R^{21}$ are as defined above,
  $A^2$ is selected from the group consisting of a covalent bond, —C(=O)—, —NH—, and —O—, preferably —NH— or —O—,
  $B^2$ is selected from the group consisting of a covalent bond, —C(=O)—, —NH—, and —O—, preferably —NH— or —O—, and
  $U^3$ is an oligourethane containing 1 to 5 repeating units made up from diisocyanates and diols, preferably made up from hexamethylene diisocyanate, toluene diisocyanate, diphenylmethylene diisocyanate, ethanediol, propane-1,2-diol, propane-1,3-diol, butane-1,4-diol, pentane-1,5-diol, benzene-1,4-diol, and bisphenol A.

According to another preferred embodiment of the invention, the aggregating additive 20 has the structure $R^{20}$-$A^2$-$U^4$—$B^2$—$R^{21}$, wherein
  $R^{20}$, $A^2$, $B^2$, and $R^{21}$ are as defined above, and
  $U^4$ is an oligourea containing 2 to 5 repeating units made up from diisocyanates and diamines, preferably made up from hexamethylene diisocyanate, toluene diisocyanate, diphenylmethylene diisocyanate, tetramethylene diamine, pentamethylene diamine, hexamethylene diamine, heptamethylene diamine, octamethylene diamine, nonamethylene diamine, decamethylene diamine, p-phenylene diamine, m-phenylene diamine, 1,3-bis(aminomethyl)benzene, 1,4-bis(aminomethyl) benzene, 1,3-bis(aminomethyl)cyclohexane, 1,4-bis (aminomethyl)cyclohexane, and 4,4'-diamino-1,1'-biphenyl.

According to another preferred embodiment of the invention, the aggregating additive 20 has the structure $D^1(-Z^1-R^{22})_3$, wherein
- each $R^{22}$ is selected from the group consisting of methyl group, ethyl group, propyl group, butyl group, pentyl group, hexyl group, heptyl group, octyl group, nonyl group, decyl group, undecyl group, dodecyl group, phenyl group, diisopropylphenyl group, di-tert.-butylphenyl group, benzyl group, diisopropylbenzyl group, di-tert.-butylbenzyl group, 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldecyl group, 1-docylundecyl group, 1-undecyldodecyl group, and 1-dodecyltridecyl group, preferably selected from the group consisting of 2-ethylhexyl group, 2-butyloctyl group, 2-hexyldecyl group, 2-octyldodecyl group, 1-pentylhexyl group, 1-hexylheptyl group, and 1-heptyloctyl group,
- $D^1$ is a benzene or cyclohexane or 1,3,5-triazine moiety, preferably a benzene core, and
- $Z^1$ is selected from the group consisting of $-C(=O)-NH-$, $-NH-C(=O)-$, $-NH-C(=O)-O-$, $-O-C(=O)-NH-$, and $-NH-C(=O)-NH-$, preferably $-C(=O)-NH-$ or $-NH-C(=O)-$.

According to another preferred embodiment of the invention, the functionalized polymer 10 has the structure $R^{21}-U^1-A^1-A^1-A^1-U^1-B^1-R^{21}$, wherein $R^{21}$, $U^1$, $A^1$, and $B^1$ are as defined above, and
- $Q^1$ is a polymer segment with a number average molecular weight from 2000 g/mol to 50000 g/mol, preferably selected from the group consisting of polyolefins, in particular poly(isoprene) (PI), hydrogenated poly(isoprene) (HPI), poly(butadiene) (PB), hydrogenated poly (butadiene) (HPB), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP); polysiloxanes, in particular poly(dimethylsiloxane) (PDMS); polyesters, in particular poly(glycolide) (PGA), amorphous or semicrystalline poly(lactide) (PLA), poly(3-hydroxybutyrate) (P3HB), poly(ethylene adipate), poly(ethylene succinate); polyethers, in particular poly(ethylene oxide) (PEO), poly(propylene oxide) (PPO), poly(tetrahydrofuran) (PTHF); and polyacrylates and polymethacrylates, in particular poly(butyl acrylate) (PBuA), poly (methyl methacrylate) (PMMA), and poly(ethylene-co-acrylate)s.

According to another preferred embodiment of the invention, the functionalized polymer 10 has the structure $R^{21}-B^1-U^2-A^1-Q^1-A^1-U^2-B^1-R^{21}$, wherein $R^{21}$, $U^2$, $A^1$, $B^1$, and $Q^1$ are as defined above.

According to another preferred embodiment of the invention, the functionalized polymer 10 has the structure $R^{21}-B^2-U^3-A^2-Q^1-A^2-U^3-B^2-R^{21}$, wherein $R^{21}$, $U^3$, $A^2$, $B^2$, and $Q^1$ are as defined above.

According to another preferred embodiment of the invention, the functionalized polymer 10 has the structure $R^{21}-B^2-U^4-A^2-Q^1-A^2-U^4-B^2-R^{21}$, wherein $R^{21}$, $U^4$, $A^2$, $B^2$, and $Q^1$ are as defined above.

According to another preferred embodiment of the invention, the functionalized polymer 10 has the structure $(R^{22}-Z^1-)_2 D^1-Z^2-Q^1-Z^1-D^1(-Z^2-R^{22})_2$, wherein
- $R^{22}$, $Z^1$, $D^1$, and $Q^1$ are as defined above and
- $Z^2$ is selected from the group consisting of $-NH-C(=O)-$, $-C(=O)-NH-$, $-O-C(=O)-NH-$, $-NH-C(=O)-O-$, and $-NH-C(=O)-NH-$, preferably $-NH-C(=O)-$ or $-C(=O)-NH-$.

According to another preferred embodiment of the invention, the invention provides a composition that contains an aggregating additive 20 with the structure $R^{20}-A^1-U^1-C(=O)-R^{21}$, wherein
- $R^{20}$, $A^1$, $U^1$, and $R^{21}$ are as defined above, and
- a functionalized polymer 10 with the structure $R^{21}-B^1-U^1-A^1-Q^1-A^1-U^1-B^1-R^{21}$, wherein
- $R^{21}$, $U^1$, $A^1$, $B^1$, and $Q^1$ are as defined above.

According to another preferred embodiment of the invention, the invention provides a composition that contains an aggregating additive 20 with the structure $R^{20}-A^1-U^2-B^1-R^{21}$, wherein
- $R^{10}$, $A^1$, $B^1$, $U^2$, and $R^{11}$ are as defined above, and
- a functionalized polymer 10 with the structure $R^{21}-B^1-U^2-A^1-Q^1-A^1-U^2-B^1-R^{21}$, wherein
- $R^{21}$, $U^2$, $A^1$, $B^1$, and $Q^1$ are as defined above.

According to another preferred embodiment of the invention, the invention provides a composition that contains an aggregating additive 20 with the structure $R^{20}-A^2-U^3-B^2-R^{21}$, wherein
- $R^{20}$, $A^2$, $B^2$, $U^3$, and $R^{21}$ are as defined above, and
- a functionalized polymer 10 with the structure $R^{21}-B^2-U^3-A^2-Q^1-A^2-U^3-B^2-R^{21}$, wherein
- $R^{21}$, $U^3$, $A^2$, $B^2$, and $Q^1$ are as defined above.

According to another preferred embodiment of the invention, the invention provides a composition that contains an aggregating additive 20 with the structure $R^{20}-A^2-U^4-B^2-R^{21}$, wherein
- $R^{20}$, $A^2$, $B^2$, $U^4$, and $R^{21}$ are as defined above, and a functionalized polymer 10 with the structure $R^{21}-B^2-U^4-A^{21}-A^2-U^4-B^2-R^{21}$ wherein
- $R^{21}$, $U^4$, $A^2$, $B^2$, and $Q^1$ are as defined above.

According to another preferred embodiment of the invention, the invention provides a composition that contains an aggregating additive 20 with the structure $D^1(-Z^1-R^{22})_3$, wherein
- $R^{22}$, $Z^1$, and $D^1$ are as defined above, and
- a functionalized polymer 10 with the structure $(R^{22}-Z^1-)_2 D^1-Z^2-Q^1-Z^1-D^1(-Z^2-R^{22})_2$, wherein
- $R^{22}$, $Z^1$, $Z^2$, $D^1$, and $Q^1$ are as defined above.

In the preferred embodiments of compositions according to the invention listed above, the composition may in particular also contain an additional polymer selected from the group consisting of polyolefins, in particular poly(isoprene) (PI), hydrogenated poly(isoprene) (HPI), poly(butadiene) (PB), hydrogenated poly(butadiene) (HPB), poly (ethylene-co-butylene) (ethylene-butylene rubber, EB), poly (styrene-co-isoprene), poly(styrene-co-butadiene) (styrene-butadiene rubber, SBR), poly(isobutylene) (PIB), amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP); polysiloxanes, in particular poly(dimethylsiloxane) (PDMS); polyesters, in particular poly(glycolide) (PGA), amorphous or semicrystalline poly(lactide) (PLA), poly(3-hydroxybutyrate) (P3HB), poly(ethylene adipate), poly(ethylene succinate); polyethers, in particular poly(ethylene oxide) (PEO), poly(propylene oxide) (PPO), poly(tetrahydrofuran) (PTHF); and polyacrylates and polymethacrylates, in particular poly(butyl acrylate) (PBuA), poly(methyl methacrylate) (PMMA), and poly(ethylene-co-acrylate)s.

The implications of the invention are further explained in the following preferred embodiments concerning thermoplastic elastomers with tailored softening temperatures, thermoplastic polymers with increased form stability at elevated temperature, and thermoplastic polymers from semicrystalline polymers with improved high temperature mechanical properties and improved melt elasticity above their melting points, which are only provided as particular examples and do not limit the scope of the invention.

Thermoplastic Elastomers with Tailored Softening Temperature One particular objective of the present invention is to provide TPEs based on high molecular weight polymers, with significantly higher softening transitions at the same or even a lower weight fraction of domains that serve as physical cross-links as compared to classical TPEs.

For this purpose, the present invention provides a composition according to claim 1 that, optionally, contains a further polymer, which is preferably unfunctionalized, according to the description above.

In order to serve as a TPE, in this particular embodiment, the polymer segment and the optional further polymer provide the rubbery matrix and hence have a glass transition temperature $T_g$ below the operating temperature T; preferably below room temperature. The $T_g$ is the temperature at which amorphous regions of the polymer pass from the viscous or rubbery state to the glassy state as the temperature is decreased. A common operational definition of the glassy state is that the viscosity of a material in the glassy state exceeds a threshold of $10^{12}$ Pa*s. Methods to determine the $T_g$ are known to the skilled person. In particular, the $T_g$ given here can be and has been determined as mid-point of the heat capacity step in differential scanning calorimetry (DSC) heating scans at a heating rate of 10 K/min. Other laboratory methods, which, however, were not applied in the current invention, include dielectric spectroscopy, static mechanical tests, dynamic mechanical analysis (DMA), or measurements of the coefficient of thermal expansion (dilatometry). Particularly preferred embodiments include compositions in which the polymer segment 13 and the optional further polymer are selected from the group consisting of poly(isoprene) (PI), hydrogenated poly(isoprene) (HPI), poly(butadiene) (PB), hydrogenated poly(butadiene) (HBP), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), and polysiloxanes, in particular poly(dimethylsiloxane) (PDMS), soft polyesters, in particular poly(glycolide) (PGA), poly(ethylene adipate), poly(ethylene succinate), polyethers, in particular poly(ethylene oxide) (PEO), poly(propylene oxide) (PPO), poly(tetrahydrofuran) (PTHF), polyacrylates, in particular poly(butyl acrylate) (PBuA); and poly(ethylene-co-acrylate)s.

The final materials can be conveniently prepared by mixing of functionalized polymer 10, aggregating additive 20, as well as, optionally, the further polymer in solution or in the melt by using appropriate blending techniques. It is believed that the combination of a functional polymer 10 and an aggregating additive 20 according to the present invention circumvents the disadvantages of regular thermoplastic elastomers (a high weight fraction of hard domains), and of supramolecular polymers and networks of high molecular weight polymers (not sufficiently strong aggregation) because the nature of the polymer segment 13 and the optional further polymer, their molecular weight, the nature and binding strength of the polymer aggregating segments 11, 12 and the at least one additive aggregating segment 21, as well as the total concentration of the polymer aggregating segments 11, 12 and additive aggregating segment 21 in the composition can all be chosen independently. Thus, the elastic and thermal properties of the obtained materials can be tailored by the choice of the type of polymer segment 13 and of the optional further polymer based on their glass transition temperatures, and by the choice of their molecular weight. Their softening temperatures, on the other hand, are primarily determined by the choice of the polymer aggregating segments 11, 12 and the at least one additive aggregating segment 21 as well as their total concentration in the composition. The present invention thus implies important advantages with respect to the state of the art in the field of thermoplastic elastomers as well as supramolecular polymers and networks. Moreover, our invention allows to precisely tune the softening transition to any temperature between the melting temperature of the polymer component and that of the additive, only by variation of their mixing ratio.

In order to choose an appropriate combination of parameters, one can conveniently apply the following exemplary procedure. If one desires to prepare a TPE with a certain desired softening temperature $T_s$ one starts by selecting an aggregating additive 20 that has (in pure form) a melting point $T_m > T_s$, preferably $T_m > T_s + 50$ K. The $T_m$ is typically determined by differential scanning calorimetry (DSC) by heating the specimen at a standard rate, typically 10 K/min, and detecting the enthalpy change associated with the melting transition. However, $T_m$ may be determined by any technique that is sensitive to molecular mobility or molecular order, including optical transmittance measurements, densitometry and mechanical measurements. This melting point represents the maximum possible softening temperature $T_s$ that can be achieved in the final TPE under any circumstances. One then chooses the polymer segment 13 and, optionally, a further polymer and their molecular weights according to the desired mechanical properties of the final TPE. The softening temperature $T_s$ of a material purely based on a functionalized polymer 10 comprising at least two polymer aggregating segments 11, 12, i.e., without the addition of an aggregating additive 20 comprising an additive aggregating segment 21, will typically be far below the melting point $T_m$ of the aggregating additive 20 for the reasons outlined above. Upon the addition of the aggregating additive 20 into the mixture however, the softening temperature $T_s$ will asymptotically approach the melting point $T_m$ of the aggregating additive 20. If the desired softening temperature $T_s$ is only reached at total concentrations of the polymer aggregating segments 11, 12 and additive aggregating segment 21 that are deemed too high (detrimental for the mechanical properties) or remains overall too low, then one can conveniently choose to start from an aggregating additive 20 with a higher melting point $T_m$.

With this exemplary procedure, the combination of the polymer aggregating segments 11, 12 and the at least one additive aggregating segment 21 provides a means to also increase the softening temperatures $T_s$ to hitherto inaccessible temperatures for these types of polymers at a given weight fraction of domains (aggregates) serving as physical cross-links. Alternatively, high softening temperatures $T_s$ are accessible for high molecular weight polymers even at comparably low total concentrations of the polymer aggregating segments 11, 12 and additive aggregating segment 21, which is beneficial for the elastic properties.

A preferred embodiment of the present invention are TPEs with a melting or dissociation temperature $T_d$ of the rigid domains that serve as physical crosslinks, $T_d>120°$ C., particularly $T_d>150°$ C., and even more so $T_d>180°$ C., at preferred total concentrations of the segments 11, 12, 21<20 wt %, particularly <10 wt %, and <5 wt %.

The rigid domains that serve as physical crosslinks may in particular be the aggregates 31. The melting or dissociation temperature of the rigid domains or the aggregates 31 may in particular be determined by differential scanning calorimetry, in particular at a heating rate of 10 K/min.

Moreover, the sharp melting temperatures that can in particular be provided from the highly cooperative deaggregation of the polymer aggregating segments 11, 12 and the additive aggregating segment 21 result in a well-defined transition from the elastic regime to viscous behavior, so that melt processing by techniques such as injection molding that involve large-scale viscous flow, may be conveniently carried out at temperatures immediately above the softening temperature. Therefore, with the composition according to the invention, supramolecular elastomers can be achieved that combine the mechanical properties of covalently cross-linked rubbers with the processability, design freedom, and recyclability of thermoplastic materials, and operate in a broad temperature range due to their significantly higher softening temperatures.

Thermoplastic Polymers with Increased Form Stability at Elevated Temperature

Another objective of the present invention is to provide thermoplastic polymers that are based on amorphous polymers with glass transition temperatures, $T_g$, above room temperature, containing low weight fractions of functional domains that serve as physical cross-links, so that these thermoplastic polymer exhibit improved form stability during transient exposure to temperatures above $T_g$, improved fracture resistance at temperatures immediately below $T_g$, and improved melt elasticity with concomitant processing advantages in a broad range of temperatures above $T_g$ compared with the corresponding non-functionalized thermoplastic polymers. For this purpose, the present invention provides a composition according to Claim 6 that, optionally, contains a further polymer, which is preferably unfunctionalized, according to the description above.

For this particular embodiment, the polymer segment 13 and the optional further polymer have a glass transition temperature $T_g$ above the operating temperature T, and preferably above room temperature. Particularly preferred embodiments include compositions in which the polymer segment 13 and the optional further polymer are selected from the group consisting of amorphous poly(styrene) (PS), poly(styrene-co-acrylonitrile) (SAN), polymethacrylates, in particular poly(methyl methacrylate) (PMMA), and amorphous polyesters, in particular amorphous poly(lactide) (PLA), in particular poly(L-lactide) (PLLA) with high contents of D-lactide.

The final materials can be conveniently prepared by mixing of functionalized polymer 10, aggregating additive 20, as well as, optionally, the further polymer in solution or in the melt by using appropriate blending techniques. The present invention implies important advantages with respect to the state of the art in the field of thermoplastics from amorphous polymers. In particular, according to this embodiment, our invention allows to precisely adjust the total concentration of the polymer aggregating segments 11, 12 and the additive aggregating segment 21 and, hence, permits control of the effective upper melting temperature of the material even at low weight fractions of the aggregating additive 20. In this way, the rubbery plateau may be extended to well-above the glass transition temperature, $T_g$, and, as a result, the form stability with respect to transient exposure to temperatures above $T_g$ during service and processability of the material are significantly enhanced. The improved form stability is because elastic behavior above $T_g$ confers a solid-like response to short term low intensity mechanical solicitation, preventing large scale flow and consequent loss in the structural and mechanical integrity of a part during service. The improved processability arises from the ability of a material to undergo deformations of up to several 100% in the unsupported state without breaking, depending on the effective entanglement and/or physical crosslink density in the rubbery state in a temperature extending from immediately above $T_g$ up to the temperature that characterizes loss in entanglement and/or physical crosslinking. The ability of a material to undergo large deformations without breaking is crucial to a wide variety of processing techniques, including film blowing, fiber spinning, foaming, thermoforming, extrusion/drawing and any other process that requires a high degree of deformability of a material in the unsupported state. Indeed, it is well known from the state of the art that unmodified poly(styrene), which is widely used to produce packaging and insulating foam, shows particularly limited melt elasticity because of its high entanglement molecular weight, such that the extent of the rubbery plateau is limited to about 15° C. above $T_g$ depending on the molecular weight, leading to coalescence and breakdown of foam cell walls. This is highly undesirable for the production of high quality closed-cell foams for packaging and insulation, and has led to many efforts to improve its melt elasticity. The presence of physical crosslinks may also significantly improve the mechanical properties of an amorphous thermoplastic at service temperatures immediately below $T_g$ when they are subjected to low intensity loads over long periods of time, which may lead to loss of structural and mechanical integrity owing to the loss of entanglement. Stable physical crosslinks will act to prevent loss of entanglement by chain slip, preventing or hindering the development of cracks. Finally, recyclability and processing of the material by melt processing techniques that require large scale viscous flow, such as injection molding, is ensured by dissociation of the self-assembling units above their softening point.

Because the improvements in the melt elasticity and other benefits resulting from the presence of physical crosslinks in the material are primarily determined by the nature and the binding strength of the supramolecular interactions between the polymer aggregating segments 11, 12 and the additive aggregating segment 21, and is consequently a function of the total concentration of the polymer aggregating segments 11, 12 and the additive aggregating segment 21, it is possible to choose the nature of the polymer segment 13 and, optionally, of the further polymer, the chain architectures, and the molecular weights of the polymer segment 13 and the further polymer can be chosen independently without affecting the softening transition temperature of the rigid domains that act as physical crosslinks. Thus, the combination of amorphous polymers based on amorphous poly (styrene) (PS), poly(styrene-co-acrylonitrile) (SAN), poly (methyl methacrylate) (PMMA), or amorphous polyesters, in particular amorphous poly(lactide) (PLA), in particular poly(L-lactide) (PLLA) with high contents of D-lactide comprising the polymer aggregating segments 11, 12 with the aggregating additive 20 results in improved form stability and elastic properties in the final materials above their respective glass transition temperatures, $T_g$, and below the melting or disaggregation temperature of the aggregating segments 11, 12, 21, and improved mechanical properties of the materials at temperatures immediately below $T_g$.

In the following, an exemplary, non-limiting procedure to choose the appropriate parameters is presented. According to this exemplary procedure, the aggregating additive 20 is selected so that it has a deaggregation temperature or melting point $T_m$(additive) above the desired dissociation temperature $T_d$ of the physical crosslinks in the final thermoplastic material, which can in turn be chosen to be considerably higher than the glass transition temperature $T_g$ of the material. Preferably, one choses the melting point of the aggregating additive 20 $T_m \geq T_d + 50°$ C. This melting point $T_m$(additive) represents the maximum possible softening temperature of the rigid domains that serve as physical crosslinks in the final thermoplastic material. To further tailor the macroscopic properties of the material, one then chooses the polymer segment 13 and, optionally, a further polymer and their molecular weights. The number average molecular weights $M_n$ of the polymer segment 13 and the unfunctionalized polymer may in principle range from 1000-100000. However, a molecular weight well above the entanglement molecular weight and preferably at least five times the entanglement molecular weight (for PS the entanglement molecular weight is typically of the order of 19000) is desired in order to adequate fracture resistance in the solid state. The upper limit of $M_n$=100000 is intended to maintain a certain threshold concentration of the polymer end groups. Given a preferred number average molecular weight $M_n$>40000, the dissociation temperature $T_d$ of the rigid domains that serve as physical crosslinks in a material purely based on the functionalized polymer 10 comprising the polymer aggregating segments 11, 12, that is without the addition of aggregating additive 20, will typically be inferior for reasons outlined above as compared to a composition using the aggregating additive 20: (i) too low concentration of the self-assembling ligands in the polymer matrix; (ii) pronounced chain entropy penalty associated with polymer chains tethered to the ligands; (iii) kinetically hindered aggregation because of comparably high viscosity of the polymer matrix in the melt. These problems can be remedied by the use of aggregating additives 20 comprising additive aggregating segments 21 to adjust the total concentration of self-assembling units in the final material, making it possible to adjust the upper limit of the rubbery plateau of this latter, which corresponds to the dissociation temperature $T_d$, of the rigid domains formed by the polymer aggregating segments 11 and 12, and the additive aggregating segments 21, so that it lies between the glass transition temperature, $T_g$, of the material and the melting temperature, $T_m$, of the aggregating additive 20 in their respective pure forms.

A preferred embodiment of the present invention are thermoplastic materials with dissociation temperatures $T_d$>120° C., particularly $T_d$>150° C., and even more so $T_d$>180° C., at preferred total concentrations of the polymer aggregating segments 11, 12 and the additive aggregating segment 21<20 wt %, particularly <10 wt %, and <5 wt %. Therefore, the extent of the rubbery plateau, given by the interval $T_d$-$T_g$ may be controlled so as to lie between 20° C. and 120° C., given that the $T_g$ of the preferred amorphous polymers lie between 60° C. for poly(lactide) (PLA), 100° C. for poly(styrene) (PS) and more than 100° C. for poly (styrene-co-acrylonitrile) (SAN), and poly(methyl methacrylate) (PMMA) depending on their composition and tacticity respectively. The choice of the interval $T_d$-$T_g$ will depend on the desired processing characteristics and applications, so that as large as possible a value may be preferred where form stability above $T_g$ is of primary importance, whereas values between 20° C. and 50° C. may be preferred where it is desired to improve melt elasticity for the purposes of thermoforming or foaming, for example, bearing in mind that $T_d$ will also determine the lower limit of the range of temperatures within which the material may be processed by techniques such as injection molding, requiring large scale viscous flow.

A further objective of the present invention is to provide thermoplastic polymers from semicrystalline polymers with improved high temperature mechanical properties, and improved melt elasticity above their melting points, $T_m$, by incorporating low weight fractions of rigid domains that serve as physical cross-links that remain stable up to their dissociation temperature, $T_d$, which is chosen to be considerably higher than $T_m$ of the base semicrystalline polymer. For this purpose, the present invention provides a composition according to Claim 7 that, optionally, contains a further polymer, which is preferably unfunctionalized, according to the description above.

For this particular embodiment, the crystalline domains of the polymer segment 13 and the optional further polymer must have a melting temperature $T_m$ above the operating temperature T. Particularly preferred embodiments include compositions in which the polymer segment 13 and the optional further polymer are selected from the group consisting of semicrystalline syndiotactic poly(styrene) (sPS), semicrystalline isotactic poly(styrene) (iPS), poly(ethylene) (PE), poly(propylene) (PP), semicrystalline polyesters, in particular poly(3-hydroxybutyrate) (P3HB), semicrystalline poly(lactide) (PLA), in particular poly(L-lactide) (PLLA), and semicrystalline polyethers.

The final materials can be conveniently prepared by mixing of functionalized polymer 10, aggregating additive 20, as well as, optionally, the further polymer in solution or in the melt by using appropriate blending techniques. The present invention implies important advantages with respect to the state of the art in the field of thermoplastics from semicrystalline polymers. Extended nanostructures comprising the polymer aggregating segments 11, 12 and the additive aggregating segment 21 serve as physical cross-links that can act as an interpenetrating network structure in the melt and accordingly contribute to form stability above the melting point $T_m$ of the base polymer, crack resistance during long term low level loading, particularly at service temperatures just below $T_m$, and melt elasticity above $T_m$, with concomitant processing advantages Already at low additive contents, the long-term mechanical stability of the material under low level loading, particularly at service temperatures just below $T_m$, may be significantly increased and toughness considerably improved, because the additional physical crosslinks hinder or prevent loss of entanglements that is otherwise known to contribute to long term embrittlement in applications such as water or gas pipes under internal pressure, for example.

Adjustment of the concentration of the polymer aggregating segments 11, 12 and the additive aggregating segment 21 permits control of the temperature range in which the melt shows significant elasticity. This is of particular importance for semicrystalline polymers, whose melting temperature, $T_m$, is generally much higher than their glass transition temperature, $T_g$. Therefore, in many semicrystalline polymers, the extent of the rubbery plateau above $T_m$ may be limited or the rubbery plateau may even be absent, depending on the molecular weight of the polymer, owing to instability of the entanglement network. Therefore for many semicrystalline polymers, processing techniques such as thermoforming and foaming are technically difficult and may require ad hoc modifications to the molecular architecture that are disadvantageous for other properties. The inclusion of physical crosslinks that are stable up to a dissociation temperature $T_d$ considerably above $T_g$ will greatly improve the processability of these polymers.

Moreover, the macroscopic properties of the final material may be advantageously influenced by unidirectional or biaxial stretching of the material in the rubbery state at temperatures between melting temperature $T_m$ of the semicrystalline polymer and the softening temperature $T_s$. of the corresponding composition stabilized by the presence of the physical crosslinks established by the aggregates comprising the aggregating segments 11, 12, and 21. This will result in aggregates 31 that form oriented nanostructures consisting of the aggregated polymer aggregating segments 11, 12 and the additive aggregating segment 21. Consecutive recrystallization of the polymer segments 13 may hence result in a stiff polymer with a highly anisotropic and controllable microstructure, with benefits for the elastic properties and mechanical strength at service temperatures, as well as other properties that depend on microstructural control, such as optical transparency.

In the following, an exemplary, non-limiting procedure to choose the appropriate parameters is presented. According to this exemplary procedure, the aggregating additive 20 is selected so that it has a melting point $T_m$ above the desired dissociation temperature $T_d$ of the physical crosslinks in the final thermoplastic material, which can in turn be chosen to lie considerably above the melting temperature $T_m$ of the material. Preferably, one choses the melting point of the aggregating additive 20 $T_m \geq T_d + 50°$ C. This melting point $T_m$ represents the maximum possible softening temperature that can be achieved in the final thermoplastic material.

The polymer segment 13 and, optionally, a further, unfunctionalized polymer are selected according to the description above. In a preferred embodiment, the molecular weight of the polymer segment 13 greatly exceeds the entanglement molecular weight of the polymer and is preferably at least five times the entanglement molecular weight. Hence, a material purely based on the functionalized polymer 10 comprising the polymer aggregating segments 11, 12, that is without the addition of aggregating additive 20, will typically be inferior for reasons outlined above as compared to a composition using the aggregating additive 20: (i) too low concentration of the self-assembling ligands in the polymer matrix; (ii) pronounced chain entropy penalty associated with polymer chains tethered to the ligands; (iii) kinetically hindered aggregation because of comparably high viscosity of the polymer matrix in the melt. These problems can be remedied by the use of aggregating additives 20 comprising additive aggregating segments 21 to adjust the total concentration of self-assembling units in the final material, making it possible to adjust the upper limit of the rubbery plateau of this latter, which corresponds to the dissociation temperature $T_d$, of the rigid domains formed by the aggregating segments 11, 12, and 21, between the melting temperature, $T_m$, of the functionalized polymer 10 and the melting temperature, $T_m$, of the aggregating additive 20 in their respective pure forms.

Other Aspects of the Invention

The invention also provides for a method for the preparation of a composition according to the invention, comprising a. providing a functionalized polymer 10 that comprises at least one polymer segment 13 and at least two polymer aggregating segments 11, 12 capable of forming non-covalent bonds based on a supramolecular interaction, b. providing an aggregating additive 20 that comprises at least one additive aggregating segment 21 capable of forming non-covalent bonds based on the same supramolecular interaction as the polymer aggregating segments 11, 12, and c. mixing the functionalized polymer 10 and the aggregating additive 20 by applying thermal and/or mechanical energy, wherein the polymer aggregating segments 11, 12 and the additive aggregating segment 21 are ditopic, wherein the polymer aggregating segments 11, 12 and the additive aggregating segment 21 are designed such that they can form aggregates 31 that contain polymer aggregating segments 11, 12 and additive aggregating segments 21, and wherein the aggregating additive 20 has a molecular weight of from 50 g/mol to 2000 g/mol, in particular from 50 g/mol to 1300 g/mol, more particularly from 50 g/mol to 1000 g/mol.

According to a preferred embodiment of the method of the invention, the aggregating additive 20 is preferably monodisperse.

The method steps provided above may be conducted in any order, but are preferably conducted in the order given above.

According to an embodiment of the method of the invention, a further polymer and/or a further additive are provided in an additional step and are mixed with the functionalized polymer 10 and the aggregating additive 20.

According to another embodiment of the method of the invention, the functionalized polymers 10, the aggregating additive 20 and, optionally, the further polymer and/or the further additive are mixed in solution or in the melt, in particular by applying thermal and/or mechanical energy. Preferably, after mixing, the resulting solution is left for 0.1 to 50 hour, more preferably 1 to 30 hours, even more preferably 10 to 25 hours, without applying mechanical energy.

According to another embodiment of the method of the invention, the composition is stretched unidirectionally or biaxially at elevated temperatures, in particular at temperatures between the melting point of the semicrystalline polymer and the softening temperature of the composition, in an additional step after step c.

For the functionalized polymer 10, the polymer aggregating segments 11, 12, the additive aggregating segments 21, the covalent bonds, the supramolecular interaction, the aggregates 31, the binding energy of the non-covalent bonds, the aggregating additive 20, the optional further polymer and the optional further additive of the method for preparation according to the invention, the above provisions concerning the functionalized polymer 10, the polymer aggregating segments 11, 12, the additive aggregating segments 21, the covalent bonds, the supramolecular interaction, the aggregates 31, the binding energy of the non-covalent bonds, the aggregating additive 20, the optional further polymer and the optional further additive of the composition according to the invention shall apply.

The method of the present invention provides a general means of introducing reversible physical branching or physical crosslinking or physical chain extension into thermoplastic polymers without adverse consequences for flow properties above a well-defined dissociation temperature of the aggregates of the aggregating segments 11, 12, 21, $T_d$, that may be chosen to be significantly higher than the upper solid-rubber or solid-liquid transition temperature of the base thermoplastic polymer, which may be a melting point or a glass transition temperature. This dissociation temperature $T_d$ lies preferentially in the range from 100° C. to 250° C. and more preferentially in the range from 150° C. to 250° C. to improve the thermomechanical properties and processing characteristics of a range of commercially important thermoplastics including, but not limited to atactic poly(styrene) (PS), poly(styrene-co-acrylonitrile) (SAN), poly(methyl methacrylate) (PMMA), amorphous or high D-content semicrystalline poly(1-lactide), poly(3-hydroxybutyrate) (P3HB), poly(ethylene) (PE), and isotactic poly(propylene) (PP).

The modified thermoplastics produced by the method of the present invention will have improved melt strength over the corresponding unmodified base thermoplastic polymer, quantifiable as (i) an increase in the melt fracture strength at a fixed temperature above the melting point or the glass transition temperature of the base thermoplastic polymer using for example Gottfert "Rheotens" melt strength tester; (ii) an increase in the temperature of the cross-over between the storage modulus and loss modulus characteristic of the high temperature limit of the rubbery plateau or melting transition in dynamic temperature scans at fixed frequency; (iii) an increase in the apparent extensional viscosity at a fixed temperature above the melting point or the glass transition temperature of the base thermoplastic polymer as determined by capillary rheometry; (iv) any other technique that reflects the increased elastic character of the thermoplastic in the temperature range from the melting point or the glass transition temperature of the base thermoplastic polymer to the dissociation temperature of the physical crosslinks or branch points.

The increased melt strength of the modified thermoplastics makes them more suitable for use in thermoforming applications than the unmodified base polymers, whose linear forms in particular are well known from the state of the art to show poor melt strength and hence to be difficult to process by thermoforming, film blowing or physical and chemical foaming, for example. The benefits include a wider temperature processing window in the modified thermoplastics than in the linear thermoplastic base polymers. The modified thermoplastics may be used in small and large part thermoforming such as in the production of items of food packaging such as margarine tubs, disposable beverage containers, or refrigerator liners, bathroom fittings and radar housing. They may show improved blow moulding characteristics, leading to reduced equipment costs, and facilitate the production of large blow moulded parts such as reservoirs and fuel tanks as an alternative to rotational moulding, for example. They may be foamed with a wider processing window than for the unmodified base polymers using either physical or chemical blowing agents, providing foams with improved morphological and physical characteristics for insulation and packaging, such as reduced open cell content and reduced cell coalescence. Waste streams of many linear thermoplastic polymers are presently difficult to recycle owing to a reduction in molecular weight during service. Use of the present invention to modify waste streams containing atactic polystyrene, isotactic polypropylene or polyethylene, by improving their melt strength, may facilitate the production of recycled objects by thermoforming, film blowing or physical and chemical foaming, for example.

The introduction of reversible physical branching or physical crosslinking or physical chain extension into rigid or semi-rigid linear thermoplastic polymers provided by the present invention will hinder or prevent chain disentanglement under load at low loading rates at any temperature or at low to high loading rates in the upper range of service temperatures and during transient exposure to temperatures exceeding the range of service temperatures corresponding to long term use. Thermoplastics commonly used under conditions of long term low level loading including at elevated temperatures include but are not limited to poly(ethylene) (PE), and isotactic poly(propylene) (PP). Furthermore, the invention may extend the range of continuous use temperatures and resistance to transient temperature increases in amorphous thermoplastics such as poly(styrene) (PS, maximum continuous use temperature 65° C., maximum operating temperature for short periods 80° C.), poly(styrene-co-acrylonitrile) (SAN, maximum continuous use temperature 65° C., maximum operating temperature for short periods 95° C.) and poly(methyl methacrylate) (PMMA, maximum continuous use temperature 70° C., maximum operating temperature for short periods 90° C.) as well as semicrystalline polymers such as poly(ethylene) (PE, maximum continuous use temperature 80° C., maximum operating temperature for short periods 100° C.) and isotactic poly(propylene) (PP, maximum continuous use temperature 130° C., maximum operating temperature for short periods 145° C.). Introduction of reversible physical branching or physical crosslinking or physical chain extension that are thermally stable up to considerably higher temperatures than the bas polymers, may provide high temperature reinforcement, to temperature ranges from 100° C. to 250° C., preferably from 150° C. to 250° C., to any of these thermoplastic polymers without compromising and possibly improving their processing characteristics. This will broaden their range of use in applications requiring exposure to high temperatures, such as under-hood automotive parts (semi-rigid hosing and ducts, manifolds, casings, gearwheels) sterilisable packaging and medical devices and electronics packaging, in which the use of thermoplastics is normally limited to more expensive and/or more expensive to process high temperature resistant polymers such as semiaromatic polycarbonates, polyamides, polysulphones, polyimides, polyesters or polyethers.

Improved heat resistance is important for elastomer applications such as O-ring seals and tubing in fuel, lubricant and hydraulic systems, radiator seals, valve stem seals, electrical connectors, hoses, diaphragms, gaskets and ducts, particularly in the automotive industry, where smaller, hotter engine compartments place increasingly stringent requirements on elastomer properties with respect both to continuous use temperatures and exposure to transient temperatures, but also in the electrical and electronics industries, biomedicine, aeronautics and other industries. The method of the present invention may provide a general means to introduce reversible physical crosslinking to chemically stable low glass transition polymers including but not limited to polyolefins, polyesters, polyethers, polyacrylates, polyacrylamides, poly(ethylene acrylate)s and polysiloxanes, such that the resulting thermoplastic elastomer shows elastomeric behaviour in a temperature range whose lower limit is determined by the base polymer properties but whose upper limit is determined by the dissociation temperature of the low weight fraction of aggregates that give rise to the physical crosslinks, and lies preferably in a range from 100° C. to 250° C., in particular from 150° C. to 250° C., which is beyond the continuous use temperature of commodity heat resistant vulcanizates, exemplified by ethylene propylene diene monomer (EPDM, maximum continuous use temperature 150° C.) and competitive with more expensive high temperature vulcanizates, such as poly(dimethylsiloxane). Thanks to the well-defined dissociation temperature of the aggregates the improved thermoplastic elastomers may be advantageously processed using standard thermoplastic processing techniques, such as injection molding, extrusion, thermoforming or film blowing with short cycle times and recycled at temperatures above the dissociation temperature of the aggregates, contrary to permanently crosslinked vulcanizates, and may show improved high temperature compression set, strength and elongation at break compared with existing temperature resistant thermoplastic rubbers such as polyurethanes and polyamide elastomers that typically contain ill-defined rigid domains with broad dissociation transitions whose transition temperature depends on the volume of the domains, so that high temperature stability may only be obtained at the expense of the elastomeric properties.

The invention also provides for the use of an aggregating additive 20 that comprises at least one additive aggregating segment 21 capable of forming non-covalent bonds based on a supramolecular interaction with a functionalized polymer 10 that comprises at least one polymer segment 13 and at least two polymer aggregating segments 11, 12 capable of forming non-covalent bonds based on the same supramolecular interaction as the at least one additive aggregating segment 21,
  wherein the polymer aggregating segments 11, 12 and the additive aggregating segment 21 are ditopic,
  wherein the polymer aggregating segments 11, 12 and the additive aggregating segment 21 are designed such that they can form aggregates 31 that contain polymer aggregating segments 11, 12 and additive aggregating segments 21, and
  wherein the aggregating additive 20 has a molecular weight of from 50 g/mol to 2000 g/mol, in particular from 50 g/mol to 1300 g/mol, more particularly from 50 g/mol to 1000 g/mol.

According to a preferred embodiment of the use of the invention, the aggregating additive 20 is preferably monodisperse.

According to a preferred embodiment of the use of the invention, the aggregating additive 20 is used to prepare a composition with the functionalized polymer 10.

For the functionalized polymer 10, the polymer aggregating segments 11, 12, the at least one additive aggregating segment 21, the covalent bonds, the supramolecular interaction, the aggregates 31, the binding energy of the non-covalent bonds, the aggregating additive 20, the optional further polymer and the optional further additive of the use according to the invention, the above provisions concerning the functionalized polymer 10, the polymer aggregating segments 11, 12, the additive aggregating segment 21, the covalent bonds, the supramolecular interaction, the aggregates 31, the binding energy of the non-covalent bonds, the aggregating additive 20, the optional further polymer and the optional further additive of the composition according to the invention shall apply.

The composition according to the invention can be used for the preparation of sheets, fibers, or molded parts. Consequently, the invention also provides for sheets, fibers, or molded parts that contain the composition according to the invention.

FIG. 1 shows a schematic overview of how the composition according to the invention can be obtained from an exemplary combination of a functionalized polymer 10 that comprises a polymer segment 13 and two polymer aggregating segments 11, 12 capable of forming non-covalent bonds based on a supramolecular interaction as terminal groups and a matching aggregating additive 20 that comprises one additive aggregating segment 21 capable of forming non-covalent bonds based on the same supramolecular interaction as the polymer aggregating segments 11, 12 of the functionalized polymer 10. The polymer aggregating segments 11, 12 and the additive aggregating segment 21 are self-complementary in this case. The polymer aggregating segments 11, 12 and the additive aggregating segments 21 aggregate into aggregates 31 in the composition that contain both polymer aggregating segments 11, 12 of the functionalized polymer 10 and additive aggregating segments 21 of the aggregating additive 20. The aggregation is in this case cooperative.

EXAMPLES

Materials

Amine-telechelic poly(styrene-co-butadiene) (H$_2$N—SBR—NH$_2$) (M$_n$=33500) was prepared using standard techniques of anionic polymerization, and purified by two subsequent precipitations from THF solution into MeOH prior to use. Boc-amino-telechelic polybutadiene (M$_n$=29000) was prepared by ring-opening metathesis polymerization of cyclooctadiene using cis-di-tert-butyl-2-butene-1,4-diyldicarbamate [R. Okabayashi, Y. Ohta, T. Yokozawa, *Macromolecules* 2017, 50, 9589-9597] as chain-transfer agent [S. Ji, T. R. Hoye, C. W. Macosko, *Macromolecules* 2004, 37, 5485-5489]. Subsequent reduction with p-toluenesulfonyl hydrazide afforded Boc-amino-telechelic PE (M$_n$=29000) [A. D. Todd, R. J. McEneany, V. A. Topolkaraev, C. W. Macosko, M. A. Hillmyer, *Macromolecules* 2016, 49, 8988-8994]. 2-hexyldecylamine was synthesized according to a literature-known procedure [X. Guo, R. Ponce Ortiz, Y. Zheng, M.-G. Kim, S. Zhang, Y. Hu, G. Lu, A. Facchetti, T. J. Marks, *J. Am. Chem. Soc.* 2011, 133, 13685-13697]. 2-octyldodecylamine was synthesized according to a literature-known procedure [S. Liu, Z. Kan, S. Thomas, F. Cruciani, J-L. Brédas, P. M. Beaujuge, *Angew. Chem. Int. Ed.* 2016, 55, 12996-13000]; N-acetyl-L-alanyl-L-alanine and N-acetyl-glycyl-glycine were synthesized according to a literature-known procedure [R. J. Cox, H. Jenkins, J. A. Schouten, R. A. Stentiford, K. J. Wareing, *J. Chem. Soc., Perkin Trans.* 1 2000, 2023-2036]; 5-(methoxycarbonyl)isophthalic acid was synthesized according to a literature-known procedure [M. A. J. Veld, D. Haveman, A. R. A. Palmans, E. W. Meijer, *Soft Matter* 2011, 7, 524-531]; 1-(3-bromopropyl)-2,2,5,5-tetramethyl-1-aza-2,5-disilacyclopentane was synthesized according to a literature-known procedure [W. N. Ottou, S. Norsic, I. Belaid, C. Boisson, F. D'Agosto, *Macromolecules* 2017, 50, 8372-8377]; amine-telechelic polydimethylsiloxane (H$_2$N-PDMS-NH$_2$, ABCR) (M$_n$=1000, 3000, 30000, 50000); diisopropylethylamine (DIEA, TCI); benzotriazol-1-yl-oxytripyrrolidinophosphonium-hexafluorophosphat (PyBOP, GL Biochem (Shanghai) Ltd.) Solvents were of technical grade and distilled prior to use. Tetrahydrofuran (THF) was dried before use by a solvent purification system (PureSolv MD-5, Innovative Technology Inc.); dichloromethane (DCM); dimethylsulfoxide (DMSO); 1,1,2,2-tetrachloroethane (TCE); trifluoroacetic acid (TFA).

Methods

Differential Scanning Calorimetry (DSC). DSC measurements were performed on a TA Instruments Q100 calorimeter at a scanning rate of 10° C./min under a flow of nitrogen (50 mL/min). The data given for the thermal transitions were obtained from the second heating scans.

Gel Permeation Chromatography (GPC). GPC measurements were performed on an Agilent 1260 Infinity GPC/SEC system with a refractive index detector. THF was used as the eluent.

Proton Nuclear Magnetic Resonance ($^1$H NMR) Spectroscopy. NMR spectroscopy was carried out at 298 K on a Bruker Avance III 400 spectrometer at a frequency of 400 MHz. The spectra were calibrated to the residual solvent peaks of DMSO-d$^6$ (2.50 ppm) or CDCl$_3$ (7.26 ppm) or TCE-d$^2$ (6.00 ppm).

High-Resolution Mass Spectrometry (HRMS). HRMS was carried out on a Q-TOF Ultima (Waters) for ESI-TOF measurements.

Dynamic Shear Rheology. Rheology measurements were carried out on a parallel plate rheometer AR 2000 (TA Instruments). Disc-shaped sample specimen that were shape-persistent were prepared manually on a hot stage or in the rheometer at 100-150° C. Aluminum plates of 15 mm were used, and the gap between the plates was in the range of 0.4-0.6 mm. All samples were annealed in the temperature range 120-200° C. for 20 min in the rheometer prior to the measurements. Measurements were carried out from 200° C. to −60° C. at a cooling rate of 3° C./min, a fixed radial frequency of 1, 10, or 100 rad/s, and a strain amplitude of 0.1% during the complete measurements.

Synthesis of Functionalized Polymers 10

Example 1:
Ac-Ala-Ala-NH—SBR—NH-Ala-Ala-Ac

Synthesis. We synthesized the functionalized polymer Ac-Ala-Ala-NH—SBR—NH-Ala-Ala-Ac, which comprises two identical polymer aggregating segments with the structure NH-Ala-Ala-Ac, by coupling amine-telechelic poly(styrene-co-butadiene) H$_2$N—SBR—NH$_2$ ($M_n$=33500) to N-acetyl-L-alanyl-L-alanine in a PyBOP-promoted peptide coupling reaction in THF as the solvent. To this end, N-acetyl-L-alanyl-L-alanine (0.18 g), DIEA (0.24 mL), and PyBOP (0.50 g) were added to a solution of amine-telechelic poly(styrene-co-butadiene) H$_2$N—SBR—NH$_2$ (24 g) in dry THF (300 mL). The reaction mixture was stirred at room temperature for 3 d and then precipitated into 1 M HCl. The precipitate was re-dissolved in THF and precipitated two more times into 1 M HCl to yield the functionalized polymer Ac-Ala-Ala-NH—SBR—NH-Ala-Ala-Ac as a colorless solid (22 g).

Characterization: $^1$H-NMR (400 MHz, CDCl$_3$): δ=7.32-6.50 (bs, 875H), 5.66-4.71 (bs, 1684H), 3.79 (m, 4H), 2.64-1.19 (bs, 3116H). The contents of polystyrene (8 n/n %), 1,2-polybutadiene (39 n/n %), and 1,4-polybutadiene (53 n/n %) units were calculated from their characteristic zones in the $^1$H-NMR spectrum. GPC (THF): $M_n$=33500.

Example 2:
Ac-Ala-Ala-NH-PDMS—NH-Ala-Ala-Ac ($M_n$=1000)

Synthesis. We synthesized the functionalized polymer Ac-Ala-Ala-NH-PDMS—NH-Ala-Ala-Ac, which comprises two identical polymer aggregating segments with the structure NH-Ala-Ala-Ac, by coupling amine-telechelic polydimethylsiloxane ($M_n$=1000) to N-acetyl-L-alanyl-L-alanine in a PyBOP-promoted peptide coupling reaction in THF as the solvent. To this end, N-acetyl-L-alanyl-L-alanine (1.02 g, 5.10 mmol), amine-telechelic polydimethylsiloxane (2 g), DIEA (1.10 mL), and PyBOP (2.85 g, 5.48 mmol) were suspended in THF (50 mL), and the reaction mixture was stirred at room temperature overnight and then precipitated into 1 M HCl (1 L). The precipitate was collected, washed with H$_2$O (3×100 mL) and dried under high vacuum to yield the functionalized polymer Ac-Ala-Ala-NH-PDMS—NH-Ala-Ala-Ac as an off-white solid (1.97 g, 69%).

Characterization: $^1$H-NMR (400 MHz, CD$_2$Cl$_2$): δ=7.93-6.51 (bs, 6H), 4.73 (bs, 4H), 3.24 (m, 4H), 2.05 (s, 6H), 1.57 (bs, 4H), 1.38 (m, 12H), 0.59 (bs, 4H), 0.13 (bs, 128H) ppm.

Example 3:
Ac-Gly-Gly-NH-PDMS-NH-Gly-Gly-Ac ($M_n$=1000)

Synthesis. We synthesized the functionalized polymer Ac-Gly-Gly-NH-PDMS-NH-Gly-Gly-Ac, which comprises two identical polymer aggregating segments with the structure NH-Gly-Gly-Ac, by coupling amine-telechelic polydimethylsiloxane ($M_n$=1000) to N-acetyl-glycyl-glycine in a PyBOP-promoted peptide coupling reaction in DMF/THF as the solvent. To this end, N-acetyl-glycyl-glycine (0.84 g, 4.80 mmol) was dissolved in DMF (20 mL) and THF (30 mL) was added. Amine-telechelic polydimethylsiloxane (2 g), DIEA (1.5 mL), and PyBOP (2.63 g, 5.09 mmol) were added and the reaction mixture was stirred at room temperature for 3 d and then precipitated into H$_2$O. The precipitate was re-dissolved in THF and precipitated one more time into H$_2$O and dried under high vacuum to yield the functionalized polymer Ac-Gly-Gly-NH-PDMS-NH-Gly-Gly-Ac as an off-white solid (1.20 g, 54%).

Characterization: $^1$H-NMR (400 MHz, CDCl$_3$): δ=7.10 (bs, 2H), 6.62 (bs, 2H), 6.38 (bs, 2H), 3.96 (m, 8H), 3.23 (bs, 4H), 2.05 (s, 6H), 1.53 (m, 4H), 0.50 (bs, 4H), 0.07 (bs, 80H) ppm.

Example 4:
Ac-Ala-Ala-NH-PDMS—NH-Ala-Ala-Ac ($M_n$=3000)

Synthesis. We synthesized the functionalized polymer Ac-Ala-Ala-NH-PDMS—NH-Ala-Ala-Ac, which comprises two identical polymer aggregating segments with the structure NH-Ala-Ala-Ac, by coupling amine-telechelic polydimethylsiloxane ($M_n$=3000) to N-acetyl-L-alanyl-L-alanine in a PyBOP-promoted peptide coupling reaction in THF as the solvent. To this end, N-acetyl-L-alanyl-L-alanine (0.32 g, 1.60 mmol), amine-telechelic polydimethylsiloxane (2 g), DIEA (0.35 mL), and PyBOP (0.90 g, 1.73 mmol) were suspended in THF (50 mL), and the reaction mixture was stirred at room temperature overnight and then precipitated into 1 M HCl (1 L). The precipitate was collected, washed with H$_2$O (3×100 mL) and dried under high vacuum to yield the functionalized polymer Ac-Ala-Ala-NH-PDMS—NH-Ala-Ala-Ac as an off-white solid (2.04 g, 90%).

Characterization: $^1$H-NMR (400 MHz, CDCl$_3$): δ=7.26-6.40 (bs, 6H), 4.60 (bs, 4H), 3.22 (m, 4H), 2.03 (s, 6H), 1.53 (m, 4H), 1.37 (m, 12H), 0.53 (m, 4H), 0.07 (bs, 213H) ppm.

Example 5:
Ac-Gly-Gly-NH-PDMS-NH-Gly-Gly-Ac
($M_n$=3000)

Synthesis. We synthesized the functionalized polymer Ac-Gly-Gly-NH-PDMS-NH-Gly-Gly-Ac, which comprises two identical polymer aggregating segments with the structure NH-Gly-Gly-Ac, by coupling amine-telechelic polydimethylsiloxane ($M_n$=3000) to N-acetyl-glycyl-glycine in a PyBOP-promoted peptide coupling reaction in DMF/THF as the solvent. To this end, N-acetyl-glycyl-glycine (0.27 g, 1.54 mmol) was dissolved in DMF (10 mL) and THF (20 mL) was added. Amine-telechelic polydimethylsiloxane (2 g), DIEA (0.5 mL), and PyBOP (0.85 g, 1.65 mmol) were added and the reaction mixture was stirred at room temperature for 3 d and then precipitated into H$_2$O. The precipitate was re-dissolved in THF and precipitated one more time into H$_2$O and dried under high vacuum to yield the functionalized polymer Ac-Gly-Gly-NH-PDMS-NH-Gly-Gly-Ac as an off-white solid (1.28 g, 47%).

Characterization: $^1$H-NMR (400 MHz, DMSO-d$^6$): δ=8.19 (bs, 2H), 8.11 (bs, 2H), 7.73 (bs, 2H), 3.67 (m, 8H), 3.03 (bs, 4H), 1.87 (s, 6H), 1.41 (bs, 4H), 0.53 (m, 4H), 0.07 (bs, 222H) ppm.

Example 6:
Ac-Ala-Ala-NH-PDMS—NH-Ala-Ala-Ac
($M_n$=30000)

Synthesis. We synthesized the functionalized polymer Ac-Ala-Ala-NH-PDMS—NH-Ala-Ala-Ac ($M_n$=30000), which comprises two identical polymer aggregating segments with the structure NH-Ala-Ala-Ac, by coupling amine-telechelic polydimethylsiloxane ($M_n$=30000) to N-acetyl-L-alanyl-L-alanine in a PyBOP-promoted peptide coupling reaction in THF as the solvent. To this end, N-acetyl-L-alanyl-L-alanine (0.34 g), DIEA (0.70 mL), and PyBOP (1.03 g) were added to a solution of amine-telechelic polydimethylsiloxane (20 g) in THF (150 mL). The reaction mixture was stirred at room temperature for 3 d and then precipitated into H$_2$O (2 L). The precipitate was re-dissolved in THF (150 mL) and precipitated two more times into H$_2$O (2 L). The precipitate was then dissolved in DCM (200 mL) and dried over MgSO$_4$. After filtration, the solvent was removed to the functionalized polymer Ac-Ala-Ala-NH-PDMS—NH-Ala-Ala-Ac ($M_n$=30000) as an off-white solid (16 g, 79%).

Characterization: $^1$H-NMR (400 MHz, CDCl$_3$): δ=6.94 (bs, 2H), 6.42 (bs, 2H), 6.36 (bs, 2H), 4.52 (m, 2H), 4.46 (m, 2H), 3.24 (m, 4H), 2.05 (s, 6H), 1.54 (m, 4H), 1.39 (t, 6H), 1.39 (t, 6H), 0.53 (m, 4H), 0.08 (bs, 3026H).

Example 7:
Ac-Gly-Gly-NH-PDMS-NH-Gly-Gly-Ac
($M_n$=30000)

Synthesis. We synthesized the functionalized polymer Ac-Gly-Gly-NH-PDMS-NH-Gly-Gly-Ac ($M_n$=30000), which comprises two identical polymer aggregating segments with the structure NH-Gly-Gly-Ac, by coupling amine-telechelic polydimethylsiloxane ($M_n$=30000) to N-acetyl-glycyl-glycine in a PyBOP-promoted peptide coupling reaction in THF as the solvent. To this end, N-acetyl-glycyl-glycine (0.31 g), DIEA (0.70 mL), and PyBOP (1.05 g) were added to a solution of amine-telechelic polydimethylsiloxane (20 g) in dry THF (150 mL). The reaction mixture was stirred at room temperature for 3 d and then precipitated into H$_2$O (2 L). The precipitate was re-dissolved in THF (200 mL) and precipitated two more times into H$_2$O (2 L). The precipitate was then dissolved in DCM (250 mL) and dried over MgSO$_4$. After filtration, the solvent was removed to yield the functionalized polymer Ac-Gly-Gly-NH-PDMS-NH-Gly-Gly-Ac ($M_n$=30000) as an off-white solid (17 g, 85%).

Characterization: $^1$H-NMR (400 MHz, CDCl$_3$): δ=6.83 (bs, 2H), 6.38 (bs, 4H), 3.97 (m, 8H), 3.28 (m, 4H), 2.08 (6H), 1.55 (m, 4H), 0.53 (m, 4H), 0.07 (bs, 5112H) ppm.

Example 8: Ac-Ala-NH-PDMS—NH-Ala-Ac
($M_n$=30000)

Synthesis. We synthesized the functionalized polymer Ac-Ala-NH-PDMS—NH-Ala-Ac ($M_n$=30000), which comprises two identical polymer aggregating segments with the structure NH-Ala-Ac, by coupling amine-telechelic polydimethylsiloxane ($M_n$=30000) to N-acetyl-L-alanine in a PyBOP-promoted peptide coupling reaction in THF as the solvent. To this end, N-acetyl-L-alanine (0.36 g), DIEA (0.8 mL), and PyBOP (1.56 g) were added to a solution of amine-telechelic polydimethylsiloxane (16.3 g) in THF (120 mL). The reaction mixture was stirred at room temperature for 1 d and then precipitated into H$_2$O (1.5 L). The water phase was decanted off and additional water was added to the remaining polymer. After vigorous stirring for 30 min the water was decanted off. The polymer was re-dissolved in DCM and dried over MgSO$_4$. After filtration, the solvent was removed to yield the functionalized polymer Ac-Ala-NH-PDMS—NH-Ala-Ac ($M_n$=30000) as a colorless viscous liquid (9.61 g, 59%).

Characterization: $^1$H-NMR (400 MHz, CDCl$_3$): δ=6.30 (bs, 4H), 4.45 (m, 2H), 3.24 (m, 4H), 2.02 (s, 6H), 1.53 (m, 4H), 1.38 (d, 6H), 0.53 (m, 4H), 0.07 (bs, 3634H) ppm.

Example 9: Ac-Gly-NH-PDMS-NH-Gly-Ac
($M_n$=30000)

Synthesis. We synthesized the functionalized polymer Ac-Gly-NH-PDMS-NH-Gly-Ac ($M_n$=30000), which comprises two identical polymer aggregating segments with the structure NH-Gly-Ac, by coupling amine-telechelic polydimethylsiloxane ($M_n$=30000) to N-acetyl-glycine in a PyBOP-promoted peptide coupling reaction in THF as the solvent. To this end, N-acetyl-glycine (42 mg), DIEA (0.10 mL), and PyBOP (0.21 g) were added to a solution of amine-telechelic polydimethylsiloxane (2.00 g) in THF (50 mL). The reaction mixture was stirred at room temperature for 1 d and then precipitated into H$_2$O. The polymer was re-dissolved in DCM (200 mL) and washed with H$_2$O three times. For further purification, the polymer was dissolved in THF and subsequently precipitated into H$_2$O. The polymer was re-dissolved in DCM and dried over MgSO$_4$. After filtration, the solvent was removed to yield the functionalized polymer Ac-Gly-NH-PDMS-NH-Gly-Ac ($M_n$=30000) as a colorless viscous liquid (1.04 g, 52%).

Characterization: $^1$H-NMR (400 MHz, CDCl$_3$): δ=6.38 (bs, 2H), 6.11 (bs, 2H), 3.92 (d, 4H), 3.26 (m, 4H), 2.05 (s, 6H), 1.54 (m, 4H), 0.53 (m, 4H), 0.07 (bs, 3180H) ppm.

Example 10: BTA-PDMS-BTA ($M_n$=30000)

Synthesis: We synthesized the functional polymer BTA-PDMS-BTA, which comprises two identical polymer aggregating segments from the group of benzene-1,3,5-tricarboxamide end groups, by coupling amine-telechelic polydimethylsiloxane ($M_n$=30000) to (3,5-bis(2-ethylhexyl)carbamoyl)benzoic acid in a PyBOP-promoted peptide coupling reaction in THF as the solvent. To this end, (3,5-bis(2-ethylhexyl)carbamoyl)benzoic acid was synthesized by suspending 5-(methoxycarbonyl)isophthalic acid (5.40 g, 24.1 mmol), 2-ethylhexan-1-amine (6.85 g, 53.0 mmol), and PyBOP (28.9 g, 55.9 mmol) in THF (150 mL). DIEA (18.9 mL) was added, and the reaction mixture was stirred at room temperature overnight and then precipitated into $H_2O$ (1 L). The precipitate was collected, dissolved in DCM and dried over $MgSO_4$, and purified by column chromatography using DCM/MeOH (100:0.5) as eluent. The intermediate methyl (3,5-bis(2-ethylhexyl)carbamoyl)benzoate was obtained as a colorless solid (4.63 g, 10.4 mmol, 43%).

Characterization: $^1$H-NMR (400 MHz, $CDCl_3$): δ=8.51 (s, 2H), 8.39 (s, 1H), 6.32 (t, 2H), 3.96 (s, 3H), 3.42 (m, 4H), 1.58 (m, 2H), 1.39 (m, 4H), 1.32 (bs, 12H), 0.95-0.88 (m, 12H) ppm. HRMS (ESI-TOF, positive): m/z 469.3042 [M+Na]$^+$, calculated for $C_{26}H_{42}N_2O_4Na$: 469.30.

(3,5-bis(2-ethylhexyl)carbamoyl)benzoate (4.50 g, 10.1 mmol) was dissolved in MeOH. LiOH (362 mg, 15.1 mmol) and water (0.5 mL) were added, and the reaction mixture was stirred at room temperature for three days and then precipitated into 1 M HCl (0.5 L). The precipitate was collected and washed with water. The (3,5-bis(2-ethylhexyl)carbamoyl)benzoic acid was obtained as a colorless solid (4.34 g, 10.0 mmol, 99%).

Characterization: $^1$H-NMR (400 MHz, DMSO-d$^6$): δ=8.68 (t, 2H), 8.60 (s, 2H), 8.45 (s, 1H), 3.37 (m, 4H), 1.68 (m, 2H), 1.47-1.37 (m, 16H), 1.00-0.93 (m, 12H) ppm. HRMS (ESI-TOF, positive): m/z 455.2886 [M+Na]$^+$, calculated for $C_{25}H_{40}N_2O_4Na$: 455.29. (3,5-bis(2-ethylhexyl)carbamoyl)benzoic acid (1.73 g, 4.00 mmol), DIEA (0.87 mL), and PyBOP (2.25 g, 4.33 mmol) were added to a solution of amine-telechelic polydimethylsiloxane (50 g) in THF (250 mL). The reaction mixture was stirred at room temperature for three days and then precipitated into $H_2O$ (1.5 L). The polymer was re-dissolved in THF (100 mL) and precipitated into $H_2O$, once more. Then, the polymer was re-dissolved in DCM and dried over $MgSO_4$. After filtration, the solvent was removed to yield the functionalized polymer BTA-PDMS-BTA ($M_n$=30000) as an off-white solid (49 g, 98%).

Characterization: $^1$H-NMR (400 MHz, $CDCl_3$): δ=8.35 (s, 6H), 6.46 (t, 2H), 6.35 (t, 4H), 3.45 (m, 12H), 1.66 (m, 4H), 1.40 (m, 4H), 1.33 (m, 32H), 0.96-0.89 (m, 24H), 0.61 (m, 4H), 0.08 (bs, 7052H) ppm.

Example 11: Ac-Ala-Ala-NH-PDMS—NH-Ala-Ala-Ac ($M_n$=50000)

Synthesis. We synthesized the functionalized polymer Ac-Ala-Ala-NH-PDMS—NH-Ala-Ala-Ac, which comprises two identical polymer aggregating segments with the structure NH-Ala-Ala-Ac, by coupling amine-telechelic polydimethylsiloxane ($M_n$=50000) to N-acetyl-L-alanyl-L-alanine in a PyBOP-promoted peptide coupling reaction in THF as the solvent. To this end, N-acetyl-L-alanyl-L-alanine (0.24 g, 1.20 mmol), DIEA (0.26 mL), and PyBOP (0.67 g, 1.50 mmol) were added to a solution of amine-telechelic polydimethylsiloxane (25 g) in THF (350 mL). The reaction mixture was stirred at room temperature for 3 d and then precipitated into $H_2O$ (1.5 L). The precipitate was re-dissolved in THF (150 mL) and precipitated two more times into $H_2O$ (1.5 L). The precipitate was then dissolved in DCM (200 mL) and dried over $MgSO_4$. For further purification, the polymer was re-dissolved in DCM (150 mL), the solution was concentrated, and MeOH (150 mL) was gradually added upon vigorous stirring. After stirring overnight, the MeOH phase was decanted off. This precipitation procedure was repeated twice. Finally, the DCM was removed in vacuum to yield the functionalized polymer Ac-Ala-Ala-NH-PDMS—NH-Ala-Ala-Ac ($M_n$=50000) as an off-white solid (12 g, 48%).

Characterization: $^1$H-NMR (400 MHz, $CDCl_3$): δ=6.80 (bs, 2H), 6.25 (bs, 2H), 6.19 (bs, 2H), 4.51 (m, 2H), 4.43 (m, 2H), 3.24 (m, 4H), 2.03 (s, 6H), 1.54 (m, 4H), 1.39 (t, 6H), 1.39 (t, 6H), 0.51 (m, 4H), 0.08 (bs, 5592H).

Example 12: Ac-Ala-Ala-Ala-NH-PDMS—NH-Ala-Ala-Ala-Ac ($M_n$=50000)

Synthesis. We synthesized the functionalized polymer Ac-Ala-Ala-Ala-NH-PDMS—NH-Ala-Ala-Ala-Ac, which comprises two identical polymer aggregating segments with the structure NH-Ala-Ala-Ala-Ac, by coupling amine-telechelic polydimethylsiloxane ($M_n$=50000) to N-acetyl-L-alanyl-L-alanyl-L-alanine in a PyBOP-promoted peptide coupling reaction in THF as the solvent. To this end, PyBOP (8.60 g, 16.5 mmol) and DIEA (6 mL) were added to a solution of N-acetyl-L-alanyl-L-alanine (2.40 g, 8.02 mmol) and L-alanine tert-butyl ester (1.73 g, 11.9 mmol) in THF (100 mL). The reaction mixture was stirred at room temperature overnight. Then, DCM was added and the mixture was stirred for 2 hours, and the resulting precipitate was collected and washed with DCM to yield N-acetyl-L-alanyl-L-alanyl-L-alanine tert-butyl ester as a colorless solid (2.24 g, 11.9 mmol, 57%).

Characterization: $^1$H-NMR (400 MHz, $D_2O$): δ=4.24-4.10 (m, 3H), 1.94 (s, 3H), 1.38 (s, 9H), 1.33-1.26 (m, 9H) ppm. HRMS (ESI-TOF, positive): m/z 352.185 [M+Na]+, calculated for $C_{15}H_{27}N_3O_5Na$: 352.18.

N-acetyl-L-alanyl-L-alanyl-L-alanine tert-butyl ester (1.60 g, 4.96 mmol) was stirred at room temperature in $CHCl_3$ (5 mL) and TFA (8.2 mL) for 3 hours. The volatiles were removed under vacuum, and the remaining solid was washed with DCM to yield N-acetyl-L-alanyl-L-alanyl-L-alanine as a colorless solid (1.18 g, 4.32 mmol, 87%).

Characterization: $^1$H-NMR (400 MHz, $D_2O$): δ=4.29-4.18 (m, 3H), 1.93 (s, 3H), 1.35 (d, 3H), 1.31 (d, 3H), 1.28 (d, 3H) ppm. HRMS (ESI-TOF, positive): m/z 296.122 [M+Na]+, calculated for $C_{11}H_{19}N_3O_5Na$: 296.12.

Then, N-acetyl-L-alanyl-L-alanyl-L-alanine (0.66 g, 2.4 mmol), PyBOP (2.3 g, 4.30 mmol), and DIEA (0.87 mL) were added to a solution of amine-telechelic polydimethylsiloxane (50 g, 1 mmol) in THF (300 mL). The reaction mixture was stirred at room temperature for 3 d and then precipitated into $H_2O$ (1.5 L). The precipitate was re-dissolved in DCM and precipitated three more times into MeOH to yield the functionalized polymer Ac-Ala-Ala-Ala-NH-PDMS—NH-Ala-Ala-Ala-Ac ($M_n$=50000) as an off-white solid (32 g, 0.64 mmol, 64%).

Characterization: $^1$H-NMR (400 MHz, $CDCl_3$): δ=7.03 (bs, 2H), 6.68 (bs, 2H), 6.61 (bs, 2H), 6.26 (bs, 2H), 4.18 (m, 6H), 3.22 (m, 4H), 2.09 (s, 6H), 1.54 (m, 4H), 1.45 (d, 6H), 1.43 (d, 6H), 1.37 (d, 6H), 0.53 (m, 4H), 0.07 (bs) ppm.

Example 13: BTA-PDMS-BTA ($M_n$=50000)

Synthesis: We synthesized the functional polymer BTA-PDMS-BTA, which comprises two identical polymer aggregating segments from the group of benzene-1,3,5-tricarboxamide end groups, by coupling amine-telechelic polydimethylsiloxane ($M_n$=50000) to (3,5-bis(2-ethylhexyl)carbamoyl)benzoic acid in a PyBOP-promoted peptide coupling reaction in THF as the solvent. To this end, (3,5-bis(2-ethylhexyl)carbamoyl)benzoic acid (0.52 g, 1.20 mmol), DIEA (0.26 mL), and PyBOP (0.68 g, 1.30 mmol) were added to a solution of amine-telechelic polydimethylsiloxane (25 g) in THF (350 mL). The reaction mixture was stirred at room temperature for three days and then precipitated into $H_2O$ (1.5 L). The polymer was re-dissolved in THF (150 mL) and precipitated into $H_2O$, once more. Then, the polymer was re-dissolved in DCM and dried over $MgSO_4$. After filtration, the solvent was removed to yield the functionalized polymer BTA-PDMS-BTA ($M_n$=50000) as an off-white solid (16 g, 64%).

Characterization: $^1$H-NMR (400 MHz, $CDCl_3$): δ=8.35 (s, 6H), 6.46 (t, 2H), 6.36 (t, 4H), 3.44 (m, 12H), 1.66 (m, 4H), 1.40 (m, 4H), 1.33 (m, 32H), 0.96-0.89 (m, 24H), 0.61 (m, 4H), 0.07 (bs, 5606H) ppm.

Example 14:
Ac-Ala-Ala-NH—PS—NH-Ala-Ala-Ac ($M_n$=3500)

Synthesis: We synthesized the functional polymer Ac-Ala-Ala-NH—PS—NH-Ala-Ala-Ac ($M_n$=3000), which comprises two identical polymer aggregating segments with the structure NH-Ala-Ala-Ac and polystyrene (PS) as an amorphous polymer segment, by coupling amine-terminated polystyrene ($M_n$=3500) to N-acetyl-L-alanyl-L-alanine in a PyBOP-promoted peptide coupling reaction in THF as the solvent. To this end, amino-telechelic polystyrene was synthesized by bidirectional living anionic polymerization of styrene initiated by sodium naphthalenide. For this purpose, naphthalene (0.39 mg), and sodium pieces (200 mg) were stirred in dry THF at room temperature for three hours under an argon atmosphere. The remaining sodium was removed from the dark green solution, and then, styrene (9.09 g, 87.3 mmol, 10 mL) was slowly added over 30 minutes at −78° C. The resulting dark red solution was stirred for three hours, while it was allowed to warm to room temperature. The reaction mixture was then cooled to −78° C. before the addition of 1-(3-bromopropyl)-2,2,5,5-tetramethyl-1-aza-2,5-disilacyclopentane (1.7 mL), and stirred at room temperature overnight. The mixture was precipitated into acidified methanol three times to yield a colorless precipitate (8.69 g, 96%). The as-obtained amino-telechelic polystyrene ($M_n$=3500) (0.48 g) was dissolved in THF. N-acetyl-L-alanyl-L-alanine (70 mg, 0.35 mmol), PyBOP (0.36 g), and DIEA (0.14 mL) were added. The reaction mixture was stirred at room temperature overnight and then precipitated into MeOH to yield the functionalized polymer Ac-Ala-Ala-NH—PS—NH-Ala-Ala-Ac ($M_n$=3000) as a colorless solid (0.23 g, 46%).

Characterization: $^1$H-NMR (400 MHz, $CDCl_3$): δ=7.00 (bs), 6.51 (bs), 3.66 (bs, 4H), 3.01 (bs, 4H), 1.78 (bs), 1.36 (bs) ppm.

Example 15: Ac-Ala-Ala-NH-PE-NH-Ala-Ala-Ac ($M_n$=29000)

Synthesis: We synthesized the functional polymer Ac-Ala-Ala-NH-PE-NH-Ala-Ala-Ac ($M_n$=29000), which comprises two identical aggregating segments with the structure NH-Ala-Ala-Ac and polyethylene (PE) as semicrystalline polymer segment, by coupling amine-terminated polyethylene ($M_n$=29000) to N-acetyl-L-alanyl-L-alanine in a PyBOP-promoted peptide coupling reaction in toluene as the solvent. To this end, boc-amino-telechelic polyethylene ($M_n$=29000) (0.5 g, 0.02 mmol) was dissolved in o-dichlorobenzene (15 mL) at 70° C. under argon atmosphere. Trifluoroacetic acid (0.2 mL) was added to the mixture, which was stirred for 16 hours at 70° C. Then, the mixture was precipitated into vigorously stirred MeOH (75 mL) at 0° C. The precipitate was collected and washed with MeOH and DCM to yield $NH_2$—PE-$NH_2$ ($M_n$=29000) an off-white solid (0.46 g, 92%).

Characterization: $^1$H-NMR (400 MHz, Tol-$d^8$): δ=2.50 (br), 1.33 (s) ppm. Then, $NH_2$—PE-$NH_2$ ($M_n$=29000) (0.46 g) was dissolved in toluene (20 mL) at 100° C. under argon atmosphere, followed by addition of PyBOP (42 mg, 0.08 mmol). Then, N-acetyl-L-alanyl-L-alanine (16 mg, 0.08 mmol) dissolved in DMSO (1 mL), and DIEA (2 mL) were added, and the reaction mixture was stirred at 100° C. for 16 hours, and then precipitated into vigorously stirred MeOH (75 mL) at 0° C. The precipitate was collected and washed with MeOH and DCM to yield the functionalized polymer Ac-Ala-Ala-NH-PE-NH-Ala-Ala-Ac ($M_n$=29000) as an off-white solid (0.44 g, 96%).

Characterization: $^1$H-NMR (400 MHz, Tol-$d^8$): δ=4.15 (bs, 4H), 3.00 (bs, 4H), 2.01 (s, 6H), 1.33 (s, 1174H).

Synthesis of Aggregating Additives 20

Example 16: N-acetyl-L-alanyl-L-alanine (2-ethylhexyl)amide

Synthesis. We synthesized the aggregating additive N-acetyl-L-alanyl-L-alanine (2-ethylhexyl)amide, which comprises an aggregating segment with the structure NH-Ala-Ala-Ac, by a PyBOP-promoted peptide coupling reaction in THF as the solvent. To this end, N-acetyl-L-alanyl-L-alanine (6.00 g, 29.6 mmol), 2-ethylhexan-1-amine (4.23 g, 32.6 mmol), and PyBOP (18.4 g, 35.6 mmol) were suspended in THF (75 mL). DIEA (15 mL) was added, and a homogenous solution was obtained. The reaction mixture was stirred at room temperature overnight and then precipitated into 1 M HCl (1 L). The precipitate was collected, washed with $H_2O$ (3×50 mL), and dried thoroughly under high vacuum to yield the aggregating additive N-acetyl-L-alanyl-L-alanine (2-ethylhexyl)amide as a colorless solid (5.91 g, 18.9 mmol, 64%).

Characterization: $^1$H-NMR (400 MHz, DMSO-$d^6$): δ=8.06 (d, 1H), 7.91 (t, 1H), 7.65 (t, 1H), 4.23 (m, 2H), 3.05 (m, 1H), 2.94 (m, 1H), 1.84 (s, 3H), 1.37 (m, 1H), 1.25-1.17 (bs, 14H), 0.87 (t, 3H), 0.83 (t, 3H) ppm. HRMS (ESI-TOF, positive): m/z 336.2268 [M+Na]+, calculated for $C_{16}H_{31}N_3O_3Na$: 336.2263. DSC: $T_m$=223° C.

Example 17: N-acetyl-L-alanyl-L-alanine (2-hexyldecyl)amide

Synthesis. We synthesized the aggregating additive N-acetyl-L-alanyl-L-alanine (2-hexyldecyl)amide, which comprises an aggregating segment with the structure NH-Ala-Ala-Ac, by a PyBOP-promoted peptide coupling reaction in THF as solvent. To this end, N-acetyl-L-alanyl-L-alanine (0.40 g, 1.98 mmol) was dissolved in dry THF (200 mL) in an argon atmosphere. 2-Hexyldecan-1-amine (0.45 g, 1.88 mmol), DIEA (0.97 mL), and PyBOP (1.18 g, 2.26 mmol) were added. The reaction mixture was stirred at room temperature in argon atmosphere for 3 h. After concentrating the mixture in vacuum, it was precipitated into 1 M HCl. The precipitate was collected, and the precipitation into 1 M HCl was repeated two times. The precipitate was dissolved in DCM and dried over MgSO$_4$. After filtration and solvent evaporation, the aggregating additive N-acetyl-L-alanyl-L-alanine (2-hexyldecyl)amide was obtained as a colorless solid (0.71 g, 1.67 mmol, 89%).

Characterization: $^1$H-NMR (400 MHz, DMSO-d$^6$): δ=6.86 (d, 1H), 6.30 (d, 1H), 6.17 (bs, 1H), 4.55 (m, 1H), 4.47 (m, 1H), 3.22 (m, 2H), 2.05 (s, 3H), 1.50 (bs, 1H), 1.40 (m, 6H), 1.28 (bs, 24H), 0.91 (m, 6H) ppm. DSC: T$_m$=184° C.

Example 18: N-acetyl-L-alanyl-L-alanine (2-octyldodecyl)amide

Synthesis. We synthesized the aggregating additive N-acetyl-L-alanyl-L-alanine (2-octyldodecyl)amide, which comprises an aggregating segment with the structure NH-Ala-Ala-Ac, by a PyBOP-promoted peptide coupling reaction in THF as the solvent. To this end, 2-octyldodecan-1-amine (2.01 g, 6.72 mmol) was dissolved in THF (50 mL). N-acetyl-L-alanyl-L-alanine (1.64 g, 8.11 mmol), PyBOP (4.87 g, 9.36 mmol), and DIEA (3.5 mL) were added, and the reaction mixture was stirred at room temperature overnight. Then, the mixture was precipitated into 1 M HCl (1 L). The precipitate was re-dissolved in THF, and the solution was again precipitated into 1 M HCl. The precipitate was finally washed with water (50 mL) and acetone (50 mL) to yield the aggregating additive N-acetyl-L-alanyl-L-alanine (2-octyldodecyl)amide as a colorless solid (2.97 g, 6.16 mmol, 92%).

Characterization: $^1$H-NMR (400 MHz, CDCl$_3$): δ=7.51 (d, 1H), 7.09 (d, 1H), 6.77 (t, 1H), 4.71 (m, 1H), 4.60 (m, 1H), 3.23 (m, 1H), 3.15 (m, 1H), 2.08 (s, 3H), 1.51 (m, 1H), 1.38 (m, 6H), 1.25 (bs, 32H), 0.87 (m, 6H) ppm. HRMS (ESI-TOF, positive): m/z 504.4145 [M+Na]$^+$, calculated for C$_{28}$H$_{55}$N$_3$O$_3$Na: 504.4141. DSC: T$_m$=186° C.

Example 19: N-acetyl-glycyl-glycine (2-ethylhexyl)amide

Synthesis. We synthesized the aggregating additive N-acetyl-glycyl-glycine (2-ethylhexyl)amide, which comprises an aggregating segment with the structure NH-Gly-Gly-Ac, by a PyBOP-promoted peptide coupling reaction in THF as the solvent. To this end, N-acetyl-glycyl-glycine (4.30 g, 21.3 mmol) was dispersed in THF (250 mL). Water was gradually added until a clear solution was obtained. 2-ethylhexylamine (5.50 g, 42.5 mmol), DIEA (11 mL), and PyBOP (13.3 g, 25.5 mmol) were added. The reaction mixture was stirred at room temperature for 15 h. After concentrating the mixture in vacuum, it was precipitated into 1 M HCl (400 mL) to yield the aggregating additive N-acetyl-glycyl-glycine (2-ethylhexyl)amide as a colorless solid (3.70 g, 13.0 mmol, 61%).

Characterization: $^1$H-NMR (400 MHz, DMSO-d$^6$): δ=8.21 (t, 1H), 8.10 (t, 1H), 7.62 (t, 1H), 3.67 (m, 4H), 3.00 (m, 2H), 1.87 (s, 3H), 1.39 (m, 1H), 1.23 (m, 8H), 0.88 (t, 3H), 0.83 (t, 3H) ppm. HRMS (ESI-TOF, positive): m/z 308.1953 [M+Na]$^+$, calculated for C$_{14}$H$_{27}$N$_3$O$_3$Na: 308.1950. DSC: T$_m$=187° C.

Example 20: N-acetyl-glycyl-glycine (2-octyldodecyl)amide

Synthesis. We synthesized the aggregating additive N-acetyl-glycyl-glycine (2-octyldodecyl)amide, which comprises an aggregating segment with the structure NH-Gly-Gly-Ac, by a PyBOP-promoted peptide coupling reaction in THF as the solvent. To this end, N-acetyl-glycyl-glycine (0.25 g, 1.24 mmol) was dissolved in DMF (25 mL). 2-Octyldodecan-1-amine (0.37 g, 1.24 mmol), DIEA (0.65 mL), and PyBOP (0.77 g, 1.48 mmol) were added. The reaction mixture was stirred at room temperature for 1 d and then precipitated into 1 M HCl (400 mL) to yield the aggregating additive N-acetyl-glycyl-glycine (2-octyldodecyl)amide as a colorless solid (0.31 g, 0.68 mmol, 55%).

Characterization: $^1$H-NMR (400 MHz, CDCl$_3$): δ=7.14 (t, 1H), 6.61 (t, 1H), 6.29 (t, 1H), 3.99 (d, 2H), 3.96 (d, 2H), 3.19 (m, 2H), 2.05 (s, 3H), 1.49 (m, 1H), 1.25 (bs, 32H), 0.88 (m, 6H) ppm. HRMS (ESI-TOF, positive): m/z 476.3835 [M+Na]+, calculated for C$_{26}$H$_{51}$N$_3$O$_3$Na: 476.3828. DSC: T$_m$=137° C.

Example 21: N$^1$,N$^3$,N$^5$-tris(2-ethylhexyl)benzene-1,3,5-tricarboxamide

Synthesis. We synthesized the aggregating additive N$^1$,N$^3$,N-tris(2-ethylhexyl) benzene-1,3,5-tricarboxamide, which comprises an aggregating segment from the group of benzene-1,3,5-tricarboxamide derivatives. To this end, triethylamine (2.11 g) and 2-ethylhexan-1-amine (2.20 g, 17.0 mmol) were dissolved in dry DCM (10 mL) in an argon atmosphere. A solution of 1,3,5-benzenetricarboxylic acid chloride (1.01 g, 3.80 mmol) in dry DCM (2 mL) was added dropwise to the reaction mixture at 0° C. The reaction mixture was stirred at room temperature in an argon atmosphere overnight. The solvent was removed, and the resulting solid was washed with 1 M HCl (3×50 mL), and H$_2$O (3×50 mL). The aggregating additive N$^1$,N$^3$,N$^5$-tris(2-ethylhexyl) benzene-1,3,5-tricarboxamide was obtained as a colorless solid (2.01 g, 3.70 mmol, 97%).

Characterization: $^1$H-NMR (400 MHz, DMSO-d$^6$): δ=8.61 (t, 3H), 8.37 (s, 3H), 3.22 (m, 6H), 1.58 (m, 3H), 1.29 (bs, 24H), 0.88 (m, 18H) ppm. HRMS (ESI-TOF, positive): m/z 544.4485 [M+H]$^+$, calculated for C$_{33}$H$_{58}$N$_3$O$_3$: 544.4478. DSC: T$_m$=289° C.

Example 22: N$^1$,N$^3$,N$^5$-tris(2-octyldodecyl)benzene-1,3,5-tricarboxamide

Synthesis: We synthesized the aggregating additive N$^1$,N$^3$,N$^5$-tris(2-octyldodecyl)benzene-1,3,5-tricarboxamide, which comprises an aggregating segment from the group of benzene-1,3,5-tricarboxamide derivatives. To this end, triethylamine (3.40 g) and 2-octyldodecan-1-amine were dissolved in dry DCM (20 mL) in an argon atmosphere. A solution of 1,3,5-benzenetricarboxylic acid chloride (2.55 g, 9.60 mmol) in dry DCM (10 mL) was added dropwise to the reaction mixture at 0° C. The reaction mixture was stirred at room temperature in an argon atmosphere for two days. The solvent was removed, and the resulting solid was washed with 1 M HCl (2×50 mL), and H$_2$O (2×50 mL), and ether (25 mL), and purified by column chromatography using ethyl acetate/hexane (1:1) as eluent. The aggregating additive N$^1$,N$^3$,N$^5$-tris(2-octyldodecyl)benzene-1,3,5-tricarboxamide was obtained as a colorless solid.

Characterization: $^1$H-NMR (400 MHz, CDCl$_3$): δ=8.34 (s, 3H), 6.37 (t, 3H), 3.41 (m, 6H), 1.63 (m, 3H), 1.32-1.25 (m, 96H), 0.87 (m, 18H) ppm. HRMS (ESI-TOF, positive): m/z 1070.9932 [M+Na]$^+$, calculated for C$_{69}$H$_{129}$N$_3$O$_3$Na: 1070.9932 DSC: T$_m$=200° C.

Example 23: N$^1$,N$^3$,N-tris(2-ethylhexyl)cyclohexane-1,3,5-tricarboxamide

Synthesis: We synthesized the aggregating additive N$^1$,N$^3$,N$^5$-tris(2-ethylhexyl)cyclohexane-1,3,5-tricarboxamide, which comprises an aggregating segment from the group of cyclohexane-1,3,5-tricarboxamide derivatives, by a PyBOP-promoted peptide coupling reaction in THF as the solvent. To this end, cyclohexane-1,3,5-tricarboxylic acid (2.00 g, 9.25 mmol), 2-ethylhexan-1-amine (4.78 g, 37.0 mmol), and PyBOP (15.9 g, 30.5 mmol) were suspended in THF (100 mL). DIEA (6.5 mL) was added, and the reaction mixture was stirred at room temperature for 18 hours. 1 M HCl (100 mL) was added, and the mixture was extracted with DCM (3×100 mL). The organic phase was dried over $MgSO_4$, before the solvent was removed. The crude product was purified by column chromatography using DCM/MeOH (96:4) as eluent, and finally by recrystallization from EtOH. The aggregating additive $N^1,N^3,N^5$-tris(2-ethylhexyl)cyclohexane-1,3,5-tricarboxamide was obtained as a colorless solid (2.60 g, 4.73 mmol, 51%).

Characterization: $^1$H-NMR (400 MHz, DMSO-d$^6$): δ=7.62 (t, 3H), 2.97 (t, 6H), 2.20 (dd, 3H), 1.67-1.43 (dd, 6H), 1.36 (m, 3H), 1.23 (m, 24H), 0.88-0.81 (m, 18H) ppm. DSC: $T_m$=231° C.

Example 24: $N^1,N^3,N^5$-tris(2-octyldodecyl)cyclohexane-1,3,5-tricarboxamide Synthesis: We synthesized the aggregating additive $N^1,N^3,N^5$-tris(2-octyldodecyl)cyclohexane-1,3,5-tricarboxamide, which comprises an aggregating segment from the group of cyclohexane-1,3,5-tricarboxamide derivatives, by a PyBOP-promoted peptide coupling reaction in THF as the solvent. To this end, cyclohexane-1,3,5-tricarboxylic acid (1.00 g, 4.63 mmol), 2-octyldodecan-1-amine (4.40 g, 14.8 mmol), and PyBOP (7.94 g, 15.3 mmol) were suspended in THF (100 mL). DIEA (3.2 mL) was added, and the reaction mixture was stirred at room temperature for 18 hours. 1 M HCl (100 mL) was added, and the mixture was extracted with DCM (3×100 mL). The organic phase was concentrated in vacuum. Over night, a precipitate occurred that was collected and recrystallized from EtOH. The aggregating additive $N^1,N^3,N^5$-tris(2-octyldodecyl)cyclohexane-1,3,5-tricarboxamide was obtained as a colorless solid (3.40 g, 3.22 mmol, 70%).

Example 25: N-acetyl-L-alanyl-L-alanyl-L-alanine (2-octyldodecyl)amide

Synthesis. We synthesized the aggregating additive N-acetyl-L-alanyl-L-alanyl-L-alanine (2-octyldodecyl)amide, which comprises an aggregating segment with the structure NH-Ala-Ala-Ala-Ac, by a PyBOP promoted peptide coupling reaction in THF as solvent. To this end, N-acetyl-L-alanyl-L-alanyl-L-alanine (200 mg, 0.73 mmol) was added to a solution of 2-octyldodecan-1-amine (181 mg, 0.67 mmol) in THF (10 mL). PyBOP (444 mg, 0.85 mmol) and DIEA (0.3 mL) were added, and the reaction mixture was stirred at room temperature overnight. Then, the mixture was precipitated into 1 M HCl. The precipitate was finally washed with water and purified by column chromatography using DCM by gradually increasing the MeOH content from 0 to 5% to yield the aggregating additive N-acetyl-L-alanyl-L-alanyl-L-alanine (2-octyldodecyl)amide as a colorless solid.

Characterization: HRMS (ESI-TOF, positive): m/z 575.800 [M+Na]$^+$, calculated for $C_{31}H_{60}N_4O_4$Na: 575.83.

Compositions Containing Functionalized Polymer 10 and Aggregating Additive 20

Example 26

Preparation of the Compositions. We prepared a series of compositions based on the functionalized polymer Ac-Ala-Ala-NH—SBR—NH-Ala-Ala-Ac ($M_n$=33500) described in Example 1 and varying amounts of the aggregating additive N-acetyl-L-alanyl-L-alanine (2-hexyldecyl)amide described in Example 17. To this end, both Ac-Ala-Ala-NH—SBR—NH-Ala-Ala-Ac and different amounts of acetyl-L-alanyl-L-alanyl-(2-hexyldecyl)amide were dissolved in DCM. The respective solutions were allowed to equilibrate for 2 d without stirring. Then, the solvent was removed in vacuum.

Thermomechanical Behavior. We characterized the thermomechanical behavior of the as-prepared compositions by oscillatory shear-rheological temperature sweeps carried out from 200° C. to −60° C. at a cooling rate of 3° C./min (Table 1). Prior to the measurement, the dissociation temperature $T_d$ of the aggregating additive was determined by DSC, and the specimens were annealed in the molten state in the rheometer at a temperature (ranging from 120° C. to 200° C.=chosen to be above the melting transition for 20 min. The softening temperatures $T_s$ were derived as the temperature at which the loss factor became tan (S 1.

TABLE 1

Thermomechanical properties of compositions of the functionalized polymer Ac-Ala-Ala-NH-SBR-NH-Ala-Ala-Ac ($M_n$ = 33500) and the aggregating additive acetyl- L-alanyl-L-alanine (2-hexyldecyl)amide obtained by oscillatory shear-rheological temperature sweeps.

| m(functionalized polymer) [wt %] | m(aggregating additive) [wt %] | c(Ac-Ala-Ala-NH) [wt %] | Softening temperature $T_s$ [° C.] |
|---|---|---|---|
| 100 | 0 | 1.2 | 98 |
| 97.3 | 2.7 | 2.4 | 134 |
| 94.7 | 5.3 | 3.6 | 138 |
| 90.1 | 9.9 | 5.7 | 157 |
| 0 | 100 | 47 | (184)$^a$ |

$^a$The melting transition of the pure additive was determined by DSC.

FIG. 2 shows graphs of rheology measurements conducted as described in the section thermomechanical behavior of Example 26. In FIG. 2, the storage modulus (G') is depicted as squares and the loss modulus (G") is depicted as circles for the pure functionalized polymer Ac-Ala-Ala-NH—SBR—NH-Ala-Ala-Ac ($M_n$=33500) (empty symbols) and for a composition containing the aggregating additive acetyl-L-alanyl-L-alanyl-(2-hexyldecyl)amide, wherein the total concentration of the aggregating segments was adjusted to 5.7 wt % (filled symbols). For instance, the pure functionalized polymer Ac-Ala-Ala-NH—SBR—NH-Ala-Ala-Ac ($M_n$=33500) behaved as a thermoplastic elastomer that showed a plateau modulus G'≈1 MPa and a fairly broad softening transition, $T_s$, defined as the temperature where the loss factor finally becomes tan δ≥1, at approximately =98° C. Upon the addition of the corresponding aggregating additive acetyl-L-alanyl-L-alanine (2-butyloctyl)amide, the softening temperature increased monotonously towards higher temperatures as a function of the overall concentration of self-assembling segments in the material and asymptotically approached the melting temperature of the additive, at 183° C. For instance, adjusting the total concentration of self-assembling segments to 5.7 wt % resulted in a softening temperature $T_s$=157° C., while the plateau modulus G' of 1 MPa was maintained.

Example 27

Preparation of the Compositions. We prepared a composition based on the functionalized polymer Ac-Gly-Gly-NH-PDMS-NH-Gly-Gly-Ac ($M_n$=30000) described in Example 7 and the aggregating additive N-acetyl-glycyl-glycine (2-ethylhexyl)amide described in Example 19. To this end, both Ac-Gly-Gly-NH-PDMS-NH-Gly-Gly-Ac (1.10 g) and acetyl-glycyl-glycine (2-ethylhexyl)amide (55 mg) were dissolved in DCM (20 mL). The solvent solutions were allowed to equilibrate for 2 d without stirring. Then, MeOH (5 mL) was added, and the solvents were removed. The resulting composition was annealed at 120° C. in high vacuum.

Thermal Properties. The dissociation temperature $T_d$ of aggregates of the aggregating segments Ac-Gly-Gly-NH in the composition has been determined from the second heating curve obtained by differential scanning calorimetry at a heating rate of 10 K/min and is listed in Table 2, along with the corresponding melting transition of Ac-Gly-Gly-NH-PDMS-NH-Gly-Gly-Ac ($M_n$=30000) and acetyl-glycyl-glycine (2-ethylhexyl)amide.

TABLE 2

Thermal properties of a composition of the functionalized polymer Ac-Gly-Gly-NH-PDMS-NH-Gly-Gly-Ac ($M_n$ = 30000) and the aggregating additive acetyl-glycyl-glycine (2-ethylhexyl)amide obtained by differential scanning calorimetry. Heating rate: 10° C./min.

| m(functionalized polymer) [wt %] | m(aggregating additive) [wt %] | c(Ac-Gly-Gly-NH) [wt %] | Dissociation temperature $T_d$ [° C.] |
|---|---|---|---|
| 100 | 0 | 1.1 | 118 |
| 95.2 | 4.8 | 4.0 | 183 |
| 0 | 100 | 60 | 187 |

For instance, the pure functionalized polymer Ac-Gly-Gly-NH-PDMS-NH-Gly-Gly-Ac ($M_n$=30000) behaved as a thermoplastic elastomer up to the dissociation temperature $T_d$=118° C. Upon the addition of the corresponding aggregating additive acetyl-glycyl-glycine (2-ethylhexyl)amide, the dissociation temperature increased monotonously towards higher temperatures as a function of the overall concentration of self-assembling segments. For instance, at an overall concentration of the aggregating segment of 4.0 wt % the dissociation temperature was $T_d$=183° C.

Example 28

Preparation of the Compositions. We prepared a composition based on the functionalized polymer BTA-PDMS-BTA ($M_n$=30000) described in Example 10 and the aggregating additive $N^1,N^3,N^5$-tris(2-ethylhexyl) benzene-1,3,5-tricarboxamide described in Example 21. To this end, both BTA-PDMS-BTA ($M_n$=30000) (1.00 g) and $N^1,N^3,N^5$-tris(2-ethylhexyl) benzene-1,3,5-tricarboxamide (21 mg) were dissolved in TCE. The solution was stirred at 100° C. for one hour. Then, the solvent was removed in vacuum.

Thermomechanical Behavior. We characterized the thermomechanical behavior of the as-prepared composition by determining the dissociation temperature $T_d$ of aggregates of the aggregating BTA segments in the composition from the second heating curve obtained by differential scanning calorimetry at a heating rate of 10 K/min (Table 3). Moreover, the temperature-dependent mechanical properties were determined by oscillatory shear-rheological temperature sweeps carried out from 150° C. to −25° C. at a cooling rate of 10° C./min. The specimen was loaded in the rheometer at 100° C.

TABLE 3

Thermal properties of a composition of the functionalized polymer BTA-PDMS-BTA ($M_n$ = 30000) and the aggregating additive $N^1,N^3,N^5$-tris(2-ethylhexyl) benzene-1,3,5-tricarboxamide obtained by differential scanning calorimetry. Heating rate: 10° C./min.

| m(functionalized polymer] [wt %] | m(aggregating additive] [wt %] | c(BTA) [wt %][a] | Dissociation temperature $T_d$ [° C.] |
|---|---|---|---|
| 100 | 0 | 1.3 | 208 |
| 98.2 | 1.8 | 2.0 | 219 |
| 0 | 100 | 38 | 289 |

[a]For the total concentration c(BTA), only the benzentricarboxamide core, $C_6H_3(C(=O)NH)_3$—, without the 2-ethylhexyl alkyl chains was employed.

FIG. 3 shows graphs of rheology measurements conducted as described in the section thermomechanical behavior of Example 28. In FIG. 3, the storage modulus (G' is depicted as squares and the loss modulus (G") is depicted as circles for the pure functionalized polymer BTA-PDMS-BTA ($M_n$=30000) described in Example 10 (empty symbols) and for a composition additionally containing the aggregating additive $N^1,N^3,N^5$-tris(2-ethylhexyl) benzene-1,3,5-tricarboxamide at an aggregating additive content of 1.8 wt % (filled symbols). For instance, the pure functionalized polymer BTA-PDMS-BTA ($M_n$=30000) behaved as a thermoplastic elastomer that showed a plateau modulus G'≈0.3 MPa and a fairly broad softening transition associated with a dissociation temperature, $T_d$, centered at around 208° C. Upon the addition of the corresponding aggregating additive $N^1,N^3,N^5$-tris(2-ethylhexyl) benzene-1,3,5-tricarboxamide, the dissociation temperature increased towards higher temperatures as a function of the overall concentration of self-assembling segments. For instance, at an aggregating additive content as low as 1.8 wt % the dissociation temperature was $T_d$=219° C., while the plateau modulus G' was slightly increased to 0.4 MPa.

Example 29

Preparation of the Composition. We prepared a composition based on the functionalized polymer BTA-PDMS-BTA ($M_n$=50000) described in Example 13 and the aggregating additive $N^1,N^3,N^5$-tris(2-ethylhexyl) benzene-1,3,5-tricarboxamide described in Example 21. To this end, both BTA-PDMS-BTA ($M_n$=50000) (1 g) and $N^1,N^3,N^5$-tris(2-ethylhexyl) benzene-1,3,5-tricarboxamide (21 mg) were dissolved in TCE (50 mL). The solution was stirred at 100° C. for one hour. Then, the solvent was removed in vacuum.

Thermal Properties. The dissociation temperature $T_d$ of aggregates of the aggregating BTA segments in the composition has been determined from the second heating curve obtained by differential scanning calorimetry at a heating rate of 10 K/min and is listed in Table 4, along with the corresponding melting transition of BTA-PDMS-BTA ($M_n$=50000) and $N^1,N^3,N^5$-tris(2-ethylhexyl) benzene-1,3,5-tricarboxamide.

TABLE 4

Thermal properties of a composition of the functionalized polymer BTA-PDMS-BTA ($M_n$ = 50000) and the aggregating additive $N^1,N^3,N^5$-tris(2-ethylhexyl) benzene-1,3,5-tricarboxamide obtained by differential scanning calorimetry. Heating rate: 10° C./min.

| m(functionalized polymer) [wt %] | m(aggregating additive) [wt %] | c(BTA) [wt %] | Dissociation temperature $T_d$ [° C.] |
|---|---|---|---|
| 100 | 0 | 0.8 | 205 |
| 98 | 2.0 | 1.5 | 220 |
| 0 | 100 | 38 | 289 |

For instance, the pure functionalized polymer BTA-PDMS-BTA ($M_n$=50000) behaved as a thermoplastic elastomer at room temperature and showed a dissociation temperature $T_d$=205° C. Upon the addition of the corresponding aggregating additive $N^1,N^3,N^5$-tris(2-ethylhexyl) benzene-1,3,5-tricarboxamide, the dissociation temperature increased monotonously towards higher temperatures as a function of the overall concentration of self-assembling segments. For instance, at an overall concentration of the aggregating segment of 1.5 wt % the dissociation temperature was $T_d$=220° C.

Example 30

Preparation of the Composition. We prepared a composition based on the functionalized polymer Ac-Ala-Ala-NH—PDMS—NH-Ala-Ala-Ac ($M_n$=50000) described in Example 11 and the aggregating additive N-acetyl-L-alanyl-L-alanine (2-ethylhexyl)amide described in Example 16. To this end, both Ac-Ala-Ala-NH-PDMS—NH-Ala-Ala-Ac ($M_n$=50000) (1 g) and N-acetyl-L-alanyl-L-alanine (2-ethylhexyl)amide (13 mg) were dissolved in TCE (50 mL). The solution was stirred at 100° C. for one hour. Then, the solvent was removed in vacuum.

Thermomechanical Behavior. The dissociation temperature $T_d$ of aggregates of the aggregating segments Ac-Ala-Ala-NH in the as-prepared composition has been determined from the second heating curve obtained by differential scanning calorimetry at a heating rate of 10 K/min and is listed in Table 5, along with the corresponding melting transition of Ac-Ala-Ala-NH-PDMS—NH-Ala-Ala-Ac ($M_n$=50000) and N-acetyl-L-alanyl-L-alanine (2-ethylhexyl)amide. We further characterized the temperature-dependent mechanical behavior of the as-prepared composition by oscillatory shear-rheological temperature sweeps carried out from 200° C. to 25° C. at a cooling rate of 10° C./min.

TABLE 5

Thermal properties of a composition of the functionalized polymer Ac-Ala-Ala-NH-PDMS-NH-Ala-Ala-Ac ($M_n$ = 50000) and the aggregating additive N-acetyl-L-alanyl-L-alanine (2-ethylhexyl)amide obtained by differential scanning calorimetry. Heating rate: 10° C./min.

| m(functionalized polymer) [wt %] | m(aggregating additive) [wt %] | c(Ac-Ala-Ala-NH) [wt %] | Dissociation temperature $T_d$ [° C.] |
|---|---|---|---|
| 100 | 0 | 0.8 | 152 |
| 98 | 2.0 | 2.1 | 211 |
| 0 | 100 | 64 | 223 |

FIG. 4 shows graphs of rheology measurements conducted as described in the section thermomechanical behavior of Example 30. In FIG. 4, the storage modulus (G' is depicted as squares and the loss modulus (G") is depicted as circles for the pure functionalized polymer Ac-Ala-Ala-NH-PDMS—NH-Ala-Ala-Ac ($M_n$=50000) (empty symbols) and for a composition additionally containing the aggregating additive N-acetyl-L-alanyl-L-alanine (2-ethylhexyl)amide, wherein the total concentration of the aggregating segments was adjusted to 2.1 wt % (filled symbols). For instance, the pure functionalized polymer Ac-Ala-Ala-NH-PDMS—NH-Ala-Ala-Ac ($M_n$=50000) behaved as a thermoplastic elastomer that showed a plateau modulus G' ≈0.6 MPa and a fairly broad dissociation transition associated with a dissociation temperature, $T_d$, centered at around 152° C. Upon the addition of the corresponding aggregating additive N-acetyl-L-alanyl-L-alanine (2-ethylhexyl)amide, the dissociation temperature increased monotonously towards higher temperatures as a function of the overall concentration of self-assembling segments. For instance, at an overall concentration of the aggregating segment of 2.1 wt % the dissociation temperature was $T_d$=211° C., while the plateau modulus increased (G'≈1 MPa). This is further reflected by a shift of the softening transition, $T_s$, defined as the temperature where the loss factor finally becomes tan δ≥1, from 147° C. for the pure functionalized polymer Ac-Ala-Ala-NH-PDMS-NH-Ala-Ala-Ac ($M_n$=50000) to 165° C. for the composition.

Example 31

Preparation of the Composition. We prepared a composition based on the functionalized polymer Ac-Ala-Ala-NH-PDMS—NH-Ala-Ala-Ac ($M_n$=50000) described in Example 11 and the aggregating additive N-acetyl-L-alanyl-L-alanine (2-octyldodecyl)amide described in Example 18. To this end, both Ac-Ala-Ala-NH-PDMS—NH-Ala-Ala-Ac ($M_n$=50000) (1 g) and N-acetyl-L-alanyl-L-alanine (2-octyldodecyl)amide (18 mg) were dissolved in TCE (50 mL). The solution was stirred at 100° C. for one hour. Then, the solvent was removed in vacuum.

Thermomechanical Behavior. The dissociation temperature $T_d$ of aggregates of the aggregating segments Ac-Ala-Ala-NH in the as-prepared composition has been determined from the second heating curve obtained by differential scanning calorimetry at a heating rate of 10 K/min and is listed in Table 6, along with the corresponding melting transition of Ac-Ala-Ala-NH-PDMS—NH-Ala-Ala-Ac ($M_n$=50000) and N-acetyl-L-alanyl-L-alanine (2-octyldodecyl)amide. We further characterized the temperature-dependent mechanical behavior of the as-prepared composition by oscillatory shear-rheological temperature sweeps carried out from 200° C. to 40° C. at a cooling rate of 10° C./min.

TABLE 6

Thermal properties of a composition of the functionalized polymer Ac-Ala-Ala-NH-PDMS-NH-Ala-Ala-Ac ($M_n$ = 50000) and the aggregating additive N-acetyl-L-alanyl-L-alanine (2-octyldodecyl)amide obtained by differential scanning calorimetry. Heating rate: 10° C./min.

| m(functionalized polymer) [wt %] | m(aggregating additive) [wt %] | c(Ac-Ala-Ala-NH) [wt %] | Dissociation temperature $T_d$ [° C.] |
|---|---|---|---|
| 100 | 0 | 0.8 | 152 |
| 98 | 2.0 | 1.6 | 175 |
| 0 | 100 | 42 | 186 |

FIG. 5 shows graphs of rheology measurements conducted as described in the section thermomechanical behavior of Example 31. In FIG. 5, the storage modulus (G') is depicted as squares and the loss modulus (G") is depicted as circles for the pure functionalized polymer Ac-Ala-Ala-NH-PDMS—NH-Ala-Ala-Ac ($M_n$=50000) (empty symbols) and for a composition additionally containing the aggregating additive N-acetyl-L-alanyl-L-alanine (2-octyldodecyl)amide, wherein the total concentration of the aggregating segments was adjusted to 1.6 wt % (filled symbols). For instance, the pure functionalized polymer Ac-Ala-Ala-NH-PDMS—NH-Ala-Ala-Ac ($M_n$=50000) behaved as a thermoplastic elastomer that showed a plateau modulus G'≈0.6 MPa and a fairly broad dissociation transition associated with a dissociation temperature, $T_d$, centered at around 152° C. Upon the addition of the corresponding aggregating additive N-acetyl-L-alanyl-L-alanine (2-octyldodecyl)amide, the dissociation temperature increased monotonously towards higher temperatures as a function of the overall concentration of self-assembling segments. For instance, at an overall concentration of the aggregating segment of 1.6 wt % the dissociation temperature was $T_d$=175° C., while the plateau modulus, G', exceeded 1 MPa. This is further reflected by a shift of the softening transition, $T_s$, defined as the temperature where the loss factor finally becomes tan δ≥1, from 147° C. for the pure functionalized polymer Ac-Ala-Ala-NH-PDMS—NH-Ala-Ala-Ac ($M_n$=50000) to 176° C. for the composition.

Example 32

Preparation of the Compositions. We prepared a series of compositions based on the functionalized polymer Ac-Ala-Ala-NH-PDMS—NH-Ala-Ala-Ac ($M_n$=30000) described in Example 6 and varying amounts of the aggregating additive N-acetyl-L-alanyl-L-alanine (2-octyldodecyl)amide described in Example 18. To this end, both Ac-Ala-Ala-NH-PDMS—NH-Ala-Ala-Ac ($M_n$=30000) and N-acetyl-L-alanyl-L-alanine (2-octyldodecyl)amide were dissolved in TCE. The respective solutions were stirred at 100° C. for one hour. Then, the solvent was removed in vacuum.

Thermomechanical Behavior. We characterized the thermomechanical behavior of the as-prepared compositions by oscillatory shear-rheological temperature sweeps carried out from 200° C. to 0° C. at a cooling rate of 3° C./min. Prior to the measurement, the dissociation temperature $T_d$ of the aggregating segments Ac-Ala-Ala-NH in the material was determined by DSC (Table 7), and the specimens were annealed in the molten state in the rheometer at a temperature chosen to be above the melting transition.

TABLE 7

Thermal properties of a composition of the functionalized polymer Ac-Ala-Ala-NH-PDMS-NH-Ala-Ala-Ac ($M_n$ = 30000) and the aggregating additive N-acetyl-L-alanyl-L-alanine (2-octyldodecyl)amide obtained by differential scanning calorimetry. Heating rate: 10° C./min.

| m(functionalized polymer) [wt %] | m(aggregating additive) [wt %] | c(Ac-Ala-Ala-NH) [wt %] | Dissociation temperature $T_d$ [° C.] |
|---|---|---|---|
| 100 | 0 | 1.3 | 140 |
| 99.75 | 0.25 | 1.4 | 161 |
| 99.5 | 0.5 | 1.5 | 166 |
| 99.0 | 1.0 | 1.7 | 169 |
| 98.3 | 1.7 | 2.0 | 174 |
| 96.6 | 3.4 | 2.7 | 177 |
| 95.0 | 5.0 | 3.3 | 181 |
| 0 | 100 | 42 | 186 |

FIG. 6 shows graphs of rheology measurements conducted as described in the section thermomechanical behavior of Example 32. In FIG. 6, the storage modulus (G') is depicted as squares and the loss modulus (G") is depicted as circles for the pure functionalized polymer Ac-Ala-Ala-NH-PDMS—NH-Ala-Ala-Ac ($M_n$=30000) (empty symbols) and for a composition additionally containing the aggregating additive N-acetyl-L-alanyl-L-alanine (2-ethylhexyl)amide, wherein the total concentration of the aggregating segments was adjusted to 3.3 wt % (filled symbols). For instance, the pure functionalized polymer Ac-Ala-Ala-NH-PDMS—NH-Ala-Ala-Ac ($M_n$=30000) behaved as a thermoplastic elastomer that showed a plateau modulus G'≈0.1 MPa and a fairly broad dissociation transition associated with a dissociation temperature, $T_d$, centered at around 140° C. Upon the addition of the corresponding aggregating additive N-acetyl-L-alanyl-L-alanine (2-octyldodecyl)amide, the dissociation temperature increased monotonously towards higher temperatures as a function of the overall concentration of self-assembling segments and approached the melting temperature of the aggregating additive ($T_d$=186° C.). For instance, at an overall concentration of the aggregating segment of 3.3 wt % the dissociation temperature was $T_d$=181° C., while the plateau modulus increased by an order of magnitude (G'≈1 MPa). This is further reflected by a shift of the softening transition, $T_s$, defined as the temperature where the loss factor finally becomes tan δ≥1, from 126° C. for the pure functionalized polymer Ac-Ala-Ala-NH-PDMS—NH-Ala-Ala-Ac ($M_n$=30000) to 159° C. for this composition.

Example 33

Preparation of the Composition. We prepared a composition based on the functionalized polymer Ac-Ala-Ala-NH-PE-NH-Ala-Ala-Ac ($M_n$=29000) described in Example 15 and the aggregating additive N-acetyl-L-alanyl-L-alanine (2-ethylhexyl)amide described in Example 16. To this end, both Ac-Ala-Ala-NH-PE-NH-Ala-Ala-Ac ($M_n$=29000) (285 mg) and N-acetyl-L-alanyl-L-alanine (2-ethylhexyl)amide (15 mg) were dissolved in TCE (15 mL). The solution was stirred at 100° C. for one hour. Then, the solvent was removed in vacuum.

Thermal Properties. The dissociation temperature $T_d$ of aggregates of the aggregating Ac-Ala-Ala-NH segments in the composition has been determined from the second heating curve obtained by differential scanning calorimetry at a heating rate of 10 K/min and is listed in Table 8, along with the corresponding melting transition of Ac-Ala-Ala-NH-PE-NH-Ala-Ala-Ac ($M_n$=29000) and N-acetyl-L-alanyl-L-alanine (2-ethylhexyl)amide.

TABLE 8

Thermal properties of a composition of the functionalized polymer Ac-Ala-Ala-NH-PE-NH-Ala-Ala-Ac ($M_n$ = 29000) and the aggregating additive N-acetyl-L-alanyl-L-alanine (2-ethylhexyl)amide obtained by differential scanning calorimetry. Heating rate: 10° C./min.

| m(functionalized polymer) [wt %] | m(aggregating additive) [wt %] | c(Ac-Ala-Ala-NH) [wt %] | Dissociation temperature $T_d$ [° C.] |
|---|---|---|---|
| 100 | 0 | 0.1 | 155 |
| 95 | 5.0 | 4.0 | 229 |
| 0 | 100 | 64 | 223 |

For instance, the pure functionalized polymer Ac-Ala-Ala-NH-PE-NH-Ala-Ala-Ac ($M_n$=29000) behaved as a thermoplastic polymer at room temperature and showed a dissociation temperature $T_d$=155° C. above the melting temperature of the PE segment. Upon the addition of the corresponding aggregating additive N-acetyl-L-alanyl-L-alanine (2-ethylhexyl)amide, the dissociation temperature increased significantly towards higher temperatures as a function of the overall concentration of self-assembling segments. For instance, at an overall concentration of the aggregating segment of 4.0 wt % the dissociation temperature was $T_d$=229° C.

The invention claimed is:

1. A composition comprising:
    a) a functionalized polymer that comprises at least one polymer segment and at least two polymer aggregating segments capable of forming non-covalent bonds based on a supramolecular interaction,
    b) an aggregating additive that comprises at least one additive aggregating segment capable of forming non-covalent bonds based on the same supramolecular interaction as the polymer aggregating segments,
    wherein the polymer aggregating segments and the additive aggregating segment are ditopic,
    wherein the polymer aggregating segments and the additive aggregating segment are designed such that they can form aggregates that contain polymer aggregating segments and additive aggregating segments, and
    wherein the aggregating additive has a number average molecular weight of from 50 g/mol to 2000 g/mol, and the aggregating additive is monodisperse.

2. The composition according to claim 1, wherein the functionalized polymer is a linear polymer and/or comprises two polymer aggregating segments as terminal groups.

3. The composition according to claim 1, wherein the polymer segment has a number average molecular weight of from 1000 g/mol to 1000000 g/mol.

4. The composition according to claim 1, wherein the polymer segment is selected from the group consisting of polyolefins, poly(isoprene) (PI), hydrogenated poly(isoprene) (HPI), poly(butadiene) (PB), hydrogenated poly(butadiene) (HBP), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), amorphous poly(styrene) (PS), semicrystalline syndiotactic poly(styrene) (sPS), semicrystalline isotactic poly(styrene) (iPS), poly(styrene-co-acrylonitrile) (SAN), poly(ethylene) (PE), poly(propylene) (PP), polysiloxanes, poly(dimethylsiloxane) (PDMS), polyesters, poly(glycolide) (PGA), amorphous poly(lactide) (PLA), semicrystalline poly(lactide) (PLA), poly(3-hydroxybutyrate) (P3HB), poly(ethylene adipate), poly(ethylene succinate), polyethers, poly(ethylene oxide) (PEO), poly(propylene oxide) (PPO), poly(tetrahydrofuran) (PTHF), polyacrylates, polymethacrylates, poly(butyl acrylate) (PBuA), poly(methyl methacrylate) (PMMA), and poly(ethylene-co-acrylate).

5. The composition according to claim 1, wherein the polymer segment is selected from the group consisting of poly(isoprene) (PI), hydrogenated poly(isoprene) (HPI), poly(butadiene) (PB), hydrogenated poly(butadiene) (HBP), poly(ethylene-co-butylene) (ethylene-butylene rubber, EB), poly(styrene-co-isoprene), poly(styrene-co-butadiene) (styrene-butadiene rubber, SBR), poly(isobutylene) (PIB), polysiloxanes, poly(dimethylsiloxane) (PDMS), soft polyesters, poly(glycolide) (PGA), poly(ethylene adipate), poly(ethylene succinate), polyethers, poly(ethylene oxide) (PEO), poly(propylene oxide) (PPO), poly(tetrahydrofuran) (PTHF), polyacrylates, poly(butyl acrylate) (PBuA), and poly(ethylene-co-acrylate).

6. The composition according to claim 1, wherein the polymer segment is selected from the group consisting of amorphous poly(styrene) (PS), poly(styrene-co-acrylonitrile) (SAN), polymethacrylates, poly(methyl methacrylate) (PMMA), amorphous polyesters,-amorphous poly(lactide) (PLA), and poly(L-lactide) (PLLA) with high contents of D-lactide.

7. The composition according to claim 1, wherein the polymer segment is selected from the group consisting of semicrystalline syndiotactic poly(styrene) (sPS), semicrystalline isotactic poly(styrene) (iPS), poly(ethylene) (PE), poly(propylene) (PP), semicrystalline polyesters, poly(3-hydroxybutyrate) (P3HB), semicrystalline poly(lactide) (PLA), poly(L-lactide) (PLLA), and semicrystalline polyethers.

8. The composition according to claim 1, wherein the aggregating additive comprises at least one additional group as a terminal group.

9. The composition according to claim 8, wherein the at least one additional group is monodisperse and/or has a molecular weight of less than 500 g/mol.

10. The composition according to claim 8, wherein each of the at least one additional group of the aggregating additive is miscible with the polymer segment and is independently selected from the group consisting of a hydrocarbon group with 1 to 30 carbon atoms, a $C_1$ to $C_{30}$ alkyl group, methyl group, ethyl group, propyl group, butyl group, pentyl group, hexyl group, heptyl group, octyl group, nonyl group, decyl group, undecyl group, dodecyl group, a $C_4$ to $C_{20}$ aromatic moiety, phenyl group, diisopropylphenyl group, di-tert.-butylphenyl group, benzyl group, diisopropylbenzyl group, di-tert-butylbenzyl group, a branched hydrocarbon group with 1 to 26 carbon atoms, 2-ethylhexyl group, 2-butyloctyl group, 2-hexyldecyl group, 2-octyldodecyl group, 2-decyltetradecyl group, 2-hexyloctanyl group, 2-octyldecyl group, 1-methylethyl group, 1-ethylpropyl group, 1-propylbutyl group, 1-butylpentyl group, 1-pentylhexyl group, 1-hexylheptyl group, 1-heptyloctyl group, 1-octylnonyl group, 1-nonyldocyl group, 1-docylundecyl group, 1-undecyldodecyl group, and 1-dodecyltridecyl group.

11. The composition according to claim 1, wherein the aggregating additive has a molecular weight of from 50 g/mol to 1900 g/mol.

12. The composition according to claim 1, wherein the melting temperature of the aggregating additive is at least 30° C. higher than the operating temperature at which materials from the composition will be used.

13. The composition according to claim 1, wherein the non-covalent bonds are selected from the group consisting of hydrogen bonds, bonds between ions and dipoles, bonds

14. The composition according to claim 1, wherein the polymer aggregating segments and the additive aggregating segment each contain at least one chemical functional group that provides a donor site and an acceptor site as interaction sites from which non-covalent bonds are formed, wherein the donor site and the acceptor site are electronically conjugated.

15. The composition according to claim 14, wherein the donor and acceptor site of the chemical functional group are capable of forming hydrogen bonds wherein the chemical functional group is selected from the group consisting of peptide (—C(=O)—NH—), amide (—C(=O)—NH—), urethane (—O—C(=O)—NH—), urea (—NH—C(=O)—NH—), thiopeptide (—C(=S)—NH—), thioamide (—C(=S)—NH—), thiourethane (—O—C(=S)—NH—), thiourea (—NH—C(=S)—NH—), —C(=NH)—NH—, —C(=NH)—NH—, —O—C(=NH)—NH—, and —NH—C(=NH)—NH—.

16. The composition according to claim 1, wherein the polymer aggregating segments and the additive aggregating segment each comprise an oligopeptide, an oligoamide, an oligourethane, an oligourea, a multifunctional cyclic or polycyclic, and/or a branched moiety comprising at least two chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—.

17. The composition according to claim 16, wherein the oligopeptide contains from 1 to 10 peptide units, the oligoamide contains from 1 to 10 amide units, the oligourethane contains from 1 to 10 urethane units, the oligourea contains from 1 to 10 urea units, and/or the multifunctional cyclic or polycyclic and/or branched moiety contains from 2 to 6 chemical functional groups independently selected from the group consisting of —C(=O)—NH—, —C(=S)—NH—, —C(=NH)—NH—, —NH—C(=O)—, —NH—C(=S)—, —NH—C(=NH)—, —NH—C(=O)—O—, —NH—C(=S)—O—, —NH—C(=NH)—O—, —NH—C(=O)—S—, —NH—C(=S)—S—, —NH—C(=NH)—S—, —NH—C(=O)—NH—, —NH—C(=S)—NH—, —NH—C(=NH)—NH—, —O—C(=O)—NH—, —O—C(=S)—NH—, —O—C(=NH)—NH—, —S—C(=O)—NH—, —S—C(=S)—NH—, and —S—C(=NH)—NH—.

* * * * *